United States Patent

Jin et al.

[11] Patent Number: 6,153,628
[45] Date of Patent: Nov. 28, 2000

[54] 1,3,4-THIADIAZOLES AND 1,3,4-OXADIAZOLES AS $\alpha_V\beta_3$ ANTAGONISTS

[75] Inventors: Fuqiang Jin, Wilmington; Pasquale N. Confalone, Greenville, both of Del.

[73] Assignee: DuPont Pharmaceuticals Company, Wilmington, Del.

[21] Appl. No.: 09/200,059

[22] Filed: Nov. 25, 1998

Related U.S. Application Data

[60] Provisional application No. 60/066,561, Nov. 26, 1997.

[51] Int. Cl.⁷ .................................................. C07D 417/00
[52] U.S. Cl. .................. 514/340; 546/268.7; 546/269.1; 514/342
[58] Field of Search .............................. 548/136; 514/363, 514/340, 342; 546/269.1, 268.7

[56] References Cited

U.S. PATENT DOCUMENTS

| | | | |
|---|---|---|---|
| 5,463,071 | 10/1995 | Himmelsbach et al. | 514/456 |
| 5,668,159 | 9/1997 | Jin et al. | 514/363 |

FOREIGN PATENT DOCUMENTS

| | | |
|---|---|---|
| 2074685 | 1/1993 | Canada . |
| 478363 | 4/1992 | European Pat. Off. . |
| 4512831 | 11/1992 | European Pat. Off. . |
| 478328 | 4/1993 | European Pat. Off. . |
| 9307867 | 4/1993 | WIPO . |
| 9408577 | 4/1994 | WIPO . |

OTHER PUBLICATIONS

Folkman & Shing, J. Biol. Chem. 1992, 267, p 10931–10934.
D'Amore and Thompson, Ann. Rev. Physiol. 1987, 49, p 453–464.
Blood and Zetter, Biochim. Biophys. Acta, 1990, 1032, p 89–118.
Brooks et al., Cell, 194, 79, P 1157–1164.
Brooks et al., Science, 1994, 264, p 569–571.
Enenstein and Kramer, J. Invest. Dermatol, 1994, 103, p 381–386.
Hynes, Cell, 1992, 69, p 11–25.
Leavesley et al. J. Cell Biol. 1993, 121, P 163–170.
VanDinther–Janssen et al., J. Immunol., 1991, 147, p 4207–4210.
Walsh et al., J. Immunol., 1991, 146, p 3419.
Bochner et al., J. Exp. Med., 1991, 173, p 1553.
Yednock et al, Nature, 1992, 356, p 63–66.
Issedutz et al., J. Immunol., 1991, 147, p 4178–4184.
Horton and Davies, J. Bone Min. Res. 1989, 4, p 803–808.
Davies et al., J. Cell. Biol. 1989, 109, p 1817–1826.
Horton, Int. J. Exp. Pathol., 1990, 71, p 741–759.
Horton et al. J. Bone Miner. Res. 1993, 8, p 239–247.
Helfrich et al., J. Bone Miner. Res. 1992, 7, p 335–343.

*Primary Examiner*—Zinna Northington Davis
*Attorney, Agent, or Firm*—Norbert F. Reinert

[57] ABSTRACT

This invention relates to 1,3,4-thiadiazoles and 1,3,4-Oxadiazoles of Formula (I) which are useful as antagonists of $\alpha_V\beta_3$ and related integrin receptors, to pharmaceutical compositions containing such compounds, alone or in combination with other therapeutic agents, for the inhibition of cell adhesion and the tretment of angioginic disorders, inflammation, bone degradation, tumors, metastases, thrombosis, and other cell aggregation-related conditions.

8 Claims, No Drawings

1,3,4-THIADIAZOLES AND 1,3,4-OXADIAZOLES AS $\alpha_v\beta_3$ ANTAGONISTS

This application claims the benefit of U.S. Provisional Application No. 60/066,561, filed Nov. 26, 1997.

FIELD OF THE INVENTION

The present invention relates generally to 1,3,4-thiadiazoles and 1,3,4-Oxadiazoles which are useful as antagonists of the $\alpha_v\beta_3$ and related integrin receptors, to pharmaceutical compositions containing such compounds, processes for preparing such compounds, and to methods of using these compounds, alone or in combination with other therapeutic agents, for the inhibition of cell adhesion and the treatment of angiogenic disorders, inflammation, bone degradation, tumors, metastases, thrombosis, and other cell aggregation-related conditions.

BACKGROUND OF THE INVENTION

Discloses angiogenesis or neovascularization is critical for normal physiological processes such as embryonic development and wound repair (Folkman and Shing, J. Biol. Chem. 1992, 267:10931–10934; D'Amore and Thompson, Ann. Rev. Physiol. 1987, 49:453–464). However, angiogenesis occurs pathologically, for example, in ocular neovascularization (leading to diabetic retinopathy, neovascular glaucoma, retinal vein occlusion and blindness), in rheumatoid arthitis and in solid tumors (Folkman and Shing, J. Biol. Chem., 1992, 267:10931–10934; Blood and Zetter, Biochim. Biophys. Acta., 1990, 1032:89–118).

Tumor dissemination, or metastasis, involves several distinct and complementary components, including the penetration and transversion of tumor cells through basement membranes and the establishment of self-sustaining tumor foci in diverse organ systems. To this end, the development and proliferation of new blood vessels, or angiogenesis, is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth. Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$ is preferentially expressed on angiogenic blood vessels in chick and man (Brooks et al., Science, 1994, 264:569–571; Enenstein and Kramer, J. Invest. Dermatol., 1994, 103:381–386). Integrin $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell, smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis. Based on this property, therapeutic utility of such agents is expected in human diseases such as cancer, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing $\alpha$- and $\beta$-subunits. Integrin subfamilies contain a common $\beta$-subunit combined with different $\alpha$-subunits to form adhesion receptors with unique specificity. The genes for eight distinct $\beta$-subunits have been cloned and sequenced to date.

Two members of the $\beta 1$ subfamily, $\alpha 4/\beta 1$ and $\alpha 5/\beta 1$ have been implicated in various inflammatory processes. Antibodies to $\alpha 4$ prevent adhesion of lymphocytes to synovial endothelial cells in vitro, a process which may be of importance in rheumatoid arthritis (VanDinther-Janssen et al., J. Immunol., 1991, 147:4207–4210). Additional studies with monoclonal anti-$\alpha 4$ antibodies provide evidence that $\alpha 4/\beta 1$ may additionally have a role in allergy, asthma, and autoimmune disorders (Walsh et al., J. Immunol., 1991, 146:3419; Bochner et al., J. Exp. Med., 1991 173:1553; Yednock et al., Nature, 1992, 356:63–66). Anti-$\alpha 4$ antibodies also block the migration of leukocytes to the site of inflammation (Issedutz et al., J. Immunol., 1991, 147:4178–4184).

The $\alpha_v/\beta_3$ heterodimer is a member of the 3 integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombosponden in a manner mediated by the RGD sequence. A key event in bone resorption is the adhesion of osteoclasts to the matrix of bone. Studies with monoclonal antibodies have implicated the $\alpha_v/\beta_3$ receptor in this process and suggest that a selective $\alpha_v/\beta_3$ antagonist would have utility in blocking bone resorption (Horton et al., J. Bone Miner. Res., 1993, 8:239–247; Helfrich et al., J. Bone Miner. Res., 1992, 7:335–343).

European Patent Application Publication Number 525629 (corresponds to Canadian Patent Application Publication Number 2,074,685) discloses compounds having the general formula:

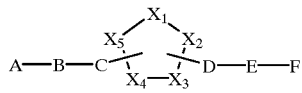

Copending, commonly assigned U.S. patent application Ser. No. 08/337,920 filed Nov. 10, 1994 discloses integrin inhibitors of the general formula shown below:

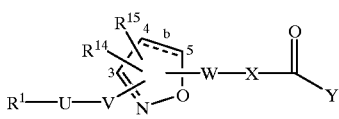

PCT Patent Application WO 94/08577 published Apr. 28, 1994 discloses fibrinogen antagonists, including the isoxazole-containing compound below:

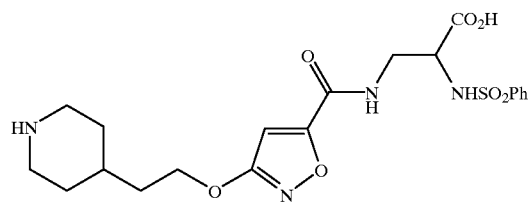

Several RGD-peptidomimetic compounds have been reported which block fibrinogen binding and prevent the formation of platelet thrombi.

European Patent Application Publication Number 478363 relates to compounds having the general formula:

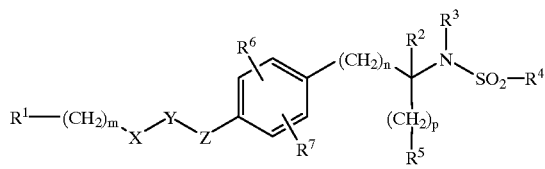

European Patent Application Publication Number 478328 relates to compounds having the general formula:

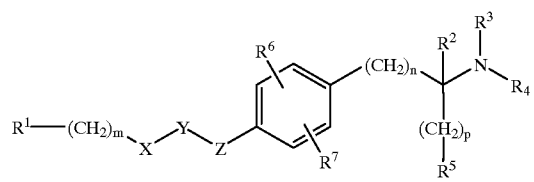

PCT Patent Application 9307867 relates to compounds having the general formula:

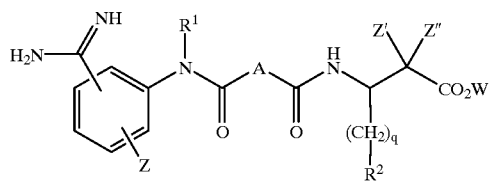

European Patent Application Publication Number 512831 relates to compounds having the general formula:

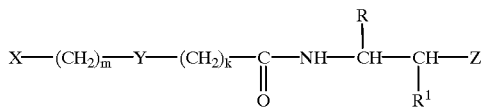

Copending commonly assigned U.S. patent application U.S. Ser. No. 08/455,768) (filed May 31, 1995, Voss et al.) discloses compounds having the general formula:

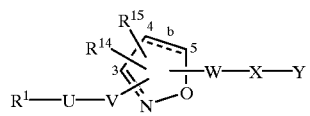

which are useful as $\alpha_v\beta_3$ antagonists.

None of the above references teaches or suggests the compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the treatment of angiogenic disorders, inflammation, bone degradation, tumors, metastases, thrombosis, and other cell aggregation-related conditions in a mammal.

One aspect of this invention provides novel compounds of Formula I (described below) which are useful as antagonists of the $\alpha_v/\beta_3$ or vitronectin receptor. The compounds of the present invention inhibit the binding of vironectin to $\alpha_v/\beta_3$ and inhibit cell adhesion. The present invention also includes pharmaceutical compositions containing such compounds of Formula I, and methods of using such compounds for the inhibition of angiogenesis, and/or for the treatment of angiogenic disorders.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, thrombosis, inflammatory bowel disease and other autoimmune diseases.

Also included in the present invention are pharmaceutical kits comprising one or more containers containing pharmaceutical dosage units comprising a compound of Formula I, for the treatment of cell adhesion related disorders, including, but not limited to, angiogenic disorders.

DETAILED DESCRIPTION OF THE INVENTION

This invention relates to novel compounds of the Formula I:

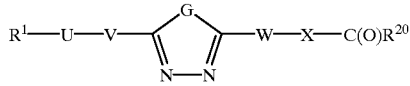
(I)

including their enantiomeric, diastereomeric, pharmaceutically acceptable salt or prodrug forms thereof wherein:

$R^1$ is:

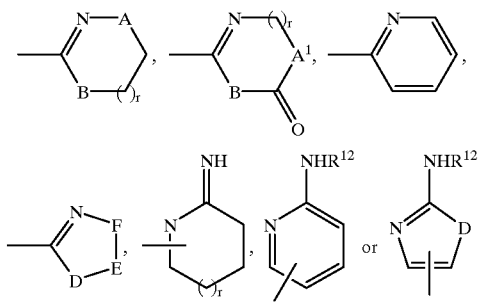

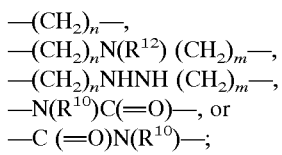

A and B are independently $CH_2$, O or $—N(R^{12})—$;
$A^1$ and $B^1$ are independently $CH_2$ or $—N(R^{10})—$;
D is NH, O, or S;
E–F is $—C(R^2)=C(R^3)—$, $—N=C(R^2)—$, $—C(R^2)=N—$, $—N=N—$, or $—CH(R^2)CH(R^3)—$;
G is selected from O or S;
$R^2$ and $R^3$ are independently selected from: H, $C_1$–$C_4$ alkoxy, $NR^{11}R^{12}$, $=NR^{12}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, or $C_7$–$C_{11}$ arylcarbonyl;
alternatively, $R^2$ and $R^3$ can be taken together to be a 5–7 membered carbocyclic or 5–7 membered heterocyclic ring system, said carbocyclic or heterocyclic ring being substituted with 0–2 $R^7$;
U is selected from:
  $—(CH_2)_n—$,
  $—(CH_2)_nN(R^{12})(CH_2)_m—$,
  $—(CH_2)_nNHNH(CH_2)_m—$,
  $—N(R^{10})C(=O)—$, or
  $—C(=O)N(R^{10})—$;
V is selected from:
  $—(CH_2)_n—$,
  $—(C_1$–$C_6$ alkylene)$—Q—$, substituted with 0–3 groups independently selected from $R^{13}$,
  $—(C_2$–$C_7$ alkenylene)$—Q—$, substituted with 0–3 groups independently selected from $R^{13}$,
  $—(C_2$–$C_7$ alkynylene)$—Q—$, substituted with 0–3 groups independently selected from $R^{13}$,
  $—$(phenyl)$—Q—$, said phenyl substituted with 0–2 groups independently selected from $R^{13}$,
  $—$(piperidinyl)$—Q—$, said piperidinyl substituted with 0–2 groups independently selected from $R^{13}$,
  $—$(pyridyl)$—Q—$, said pyridyl substituted with 0–2 groups independently selected from $R^{13}$, or
  $—$(pyridazinyl)$—Q—$, said pyridazinyl substituted with 0–2 groups independently selected from $R^{13}$ or $R^7$;

Q is selected from:
  $—(CH_2)_n—$,
  $—(CH_2)_nO(CH_2)_m—$,
  $—(CH_2)_nN(R^{12})(CH_2)_m—$,
  $—N(R^{10})C(=O)—$, or
  $—C(=O)N(R^{10})—$;
W is selected from:
  $—(CH_2)_qC(=O)N(R^{10})—$, $—SCH_2C(=O)N(R^{10})—$, or
  $—C(=O)—N (R^{10})—(CH_2)_q—$;
X is selected from:
  $—(CH_2)_q—CH(R^8)—CH(R^9)—$, $—(CH_2)_q—CH(CH_2R^9)—$ or $—CH_2—$
$R^5$ is selected from: H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, $—N(R^{11})R^{12}$; halo, $CF_3$, CN, $C_1$–$C_6$ alkoxycarbonyl, carboxy, piperidinyl, morpholinyl or pyridinyl;
$R^6$ is selected from:
  H, $C_1$–$C_4$ alkyl, hydroxy, $C_1$–$C_4$ alkoxy, nitro, $C_1$–$C_6$ alkylcarbonyl, $—N(R^{11})R^{12}$, cyano, halo, $—S(O)_mR^{10}$, $CO_2R^{10}$, $OR^{10}$,
  $C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or $—NMe_2$;
  methylenedioxy when $R^6$ is a substituent on aryl, or
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl, or morpholinyl;
$R^7$ is selected from:
  H, $C_1$–$C_{10}$ alkyl, hydroxy, $C_1$–$C_{10}$ alkoxy, nitro, $C_1$–$C_{10}$ alkylcarbonyl, $—N(R^{11})R^{12}$, cyano, halo, $CO_2R^{10}$, $OR^{10}$;
$R^8$ is selected from:
  $CONR^{10}R^{11}$, $—CO_2R^{10}$,
  $C_1$–$C_{10}$ alkyl, substituted with 0–3 $R^6$,
  $C_2$–$C_{10}$ alkenyl, substituted with 0–3 $R^6$,
  $C_2$–$C_{10}$ alkynyl, substituted with 0–3 $R^6$,
  $C_3$–$C_8$ cycloalkyl, substituted with 0–3 $R^6$,
  $C_5$–$C_6$ cycloalkenyl, substituted with 0–3 $R^6$,
  aryl, substituted with 0–3 $R^6$,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl;
$R^9$ is selected from: H, hydroxy, $C_1$–$C_{10}$ alkoxy, nitro, $N(R^{10})R^{10}$, $—N(R^{16})R^{17}$, $C_1$–$C_{10}$ alkyl substituted with 0–3 $R^6$, aryl substituted with 0–3 $R^6$, heteroaryl substituted with 0–3 $R^6$ or $C_1$–$C_{10}$ alkylcarbonyl;
$R^{10}$ is selected from H or $C_1$–$C_{10}$ alkyl substituted with 0–2 $R^5$;
$R^{11}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^5$;

alternatively, $R^{10}$ and $R^{11}$ when both are substituents on the same nitrogen atom (as in —$NR^{10}R^{11}$) can be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 1–3 groups selected from: $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{12}$ is selected from:
H, $C_1$–$C_6$ alkyl, $C_1$–$C_4$ alkoxycarbonyl, $C_1$–$C_6$ alkylcarbonyl, $C_1$–$C_6$ alkylsulfonyl, aryl($C_1$–$C_4$ alkyl) sulfonyl, arylsulfonyl, aryl, heteroarylcarbonyl, or heteroarylalkylcarbonyl, wherein said aryl groups are substituted with 0–3 substituents selected from the group consisting of: $C_1$–$C_4$ alkyl, $C_1$–$C_4$ alkoxy, halo, $CF_3$, and $NO_2$;

$R^{13}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^{10}$ or —C(=O)N($R^{10}$)$R^{11}$;

$R^{16}$ is selected from:
—C(=O)—O—$R^{18a}$,
—C(=O)—$R^{18b}$,
—$SO_2$—$R^{18a}$,
—$SO_2$—N($18^b$)$_2$;

$R^{17}$ is selected from H or $C_1$–$C_4$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)- substituted with 0–4 $R^{19}$,
a heterocyclic ring system selected from
pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, isoxazolyl, benzimidazolyl, piperidinyl, tetrahydrofuranyl, pyranyl, pyrimidinyl, 3H-indolyl, carbazolyl, pyrrolidinyl, piperidinyl, indolinyl, or morpholinyl, said heterocyclic ring being substituted with 0–4 $R^{19}$;
$C_1$–$C_6$ alkyl substituted with a heterocyclic ring system selected from pyridinyl, furanyl, thiazolyl, thienyl, pyrrolyl, pyrazolyl, imidazolyl, isoxazolinyl, isoxazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from: H, halogen, $CF_3$, CN, $NO_2$, $NR^{11}R^{12}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)—, $C_1$–$C_6$ alkoxy, or $C_1$–$C_4$ alkoxycarbonyl;

$R^{20}$ is selected from:
hydroxy;
$C_1$ to $C_{10}$ alkoxy;

methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl) methoxy-,
(1,3-dioxa-5-phenyl-cyclopenten-2-on-4-yl)methoxy-,
1-(2-(2-methoxypropyl)carbonyloxy)ethoxy-, $R^{21}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^5$;

m is 0–2;
n is 0–2;
p is 0–2;
q is 0–1; and
r is 0–2;

with the following provisos:
(1) n, m and q are chosen such that the number of atoms connecting $R^1$ and Y is in the range of 8–14; and
(2) when V is -(phenyl)—Q—, then either: U is not a direct bond (i.e., U is not —$(CH_2)_n$— where n=0) or Q is not a direct bond (i.e., Q is not —$(CH_2)_n$— where n=0).

A preferred embodiment of the invention are compounds of formula (I) as defined above wherein
$R^1$

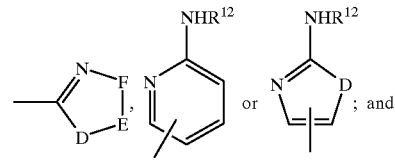

V is selected from:
—$(CH_2)_n$—,
—($C_1$–$C_6$ alkylene)—Q—, substituted with 0–3 groups independently selected from $R^{13}$,
—($C_2$–$C_7$ alkenylene)—Q—, substituted with 0–3 groups independently selected from $R^{13}$,
—($C_2$–$C_7$ alkynylene)—Q—, substituted with 0–3 groups independently selected from $R^{13}$,
—(phenyl)—Q—, said phenyl substituted with 0–2 groups independently selected from $R^{13}$,
—(pyridyl)—Q—, said pyridyl substituted with 0–2 groups independently selected from $R^{13}$, or
—(pyridazinyl)—Q—, said pyridazinyl substituted with 0–2 groups independently selected from $R^{13}$ or $R^7$;

The most preferred compounds of the invention are:

2(S)-Phenylsulfonylamino-3-[2-[2-[3-[(N-imidazolin-2-yl)amino]propyl]-1,3,4-thiadiazol-5-yl]acetyl]aminopropionic acid
2(S)-(3-methylphenylsulfonyl)amino-3-[2-[2-[3-[(N-imidazolin-2-yl)amino]propyl]-1,3,4-thiadiazol-5-yl]acetyl]aminopropionic acid
2(S)-Benzyloxycarbonylamino-3-[[2-[4-[N-(pyridin-2-yl)amino]butyl]-1,3,4-thiadiazol-5-yl]carbonyl]aminopropionic acid TFA salt
2(S)-(2,4,6-Trimethylphenylsulfonyl)amino-3-[[2-[4-[N-(pyridin-2-yl)amino]butyl]-1,3,4-thiadiazol-5-yl]carbonyl]aminopropionic acid TFA salt
2(S)-(1-Naphthalenesulfonyl)amino-3-[[2-[4-[N-(pyridin-2-yl)amino]butyl]-1,3,4-thiadiazol-5-yl]carbonyl]aminopropionic acid TFA salt
2(S)-Benzyloxycarbonylamino-3-[[2-[4-[(N-imidazolin-2-yl)amino]butyl]-1,3,4-thiadiazol-5-yl]carbonyl]aminopropionic acid TFA salt
2(S)-(2,4,6-Trimethylphenylsulfonyl)amino-3-[[2-[4-[(N-imidazolin-2-yl)amino]butyl]-1,3,4-thiadiazol-5-yl]carbonyl]aminopropionic acid TFA salt
2(S)-(1-Naphthalenesulfonyl)amino-3-[[2-[4-[(N-imidazolin-2-yl)amino]butyl]-1,3,4-thiadiazol-5-yl]carbonyl]aminopropionic acid TFA salt In the present invention it has been discovered that the compounds of Formula I above are useful as inhibitors of cell-matrix and cell-cell adhesion processes. The present invention includes novel compounds of Formula I and methods for using such compounds for the prevention or treatment of diseases resulting from abnormal cell adhesion to the extracellular matrix which comprises administering to a host in need of such treatment a therapeutically effective amount of such compound of Formula I. In the present invention it has also been discovered that the compounds of Formula I above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formula I and a pharmaceutically acceptable carrier.

The compounds of Formula I of the present invention are useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion, comprising administering to a mammal in need of such treatment a therapeutically effective amount of a compound of Formula I described above.

The compounds of Formula I of the present invention may be useful for the treatment or prevention of other diseases which involve cell adhesion processes, including, but not limited to, inflammation, bone degradation, thromboembolic disorders, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula I of the present invention may also be useful for wound healing.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin and other inhibitors of thrombin synthesis such as Factor XA. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of nitronection or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperazinyl or piperidinyl unless specified otherwise, said piperazinyl or piperidinyl group may be bonded to the rest of the compound of Formula I via any atom in such piperazinyl or piperidinyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "alkoxy" represents an alkyl group of indicated number of carbon atoms attached through an oxygen bridge; "cycloalkyl" is intended to include saturated ring groups, including mono-, bi-, or poly-cyclic ring systems, such as cyclopropyl, and cyclobutyl; cyclohexyl, cycloheptyl, cyclooctyl, and adamantyl; and "bicycloalkyl" is intended to include saturated bicyclic ring groups such as [3.3.0] bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl optionally substituted with 0–3 groups independently selected from methyl, methoxy, amino, hydroxy, halogen, $C_1$–$C_6$ alkoxy, $C_1$–$C_6$ alkyl, $CF_3$, $S(O)_m CH_3$, $—N(CH_3)_2$, $C_1$–$C_4$ haloalkyl, methylenedioxydiyl, ethylenedioxydiyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, the term "chiral amine" refers to any amine containing compound that also contains a chiral center. Such compounds include, by way of example and without limitation, either enantiomer of cinchonidine, ephedrine, 2-phenylglycinol, 2-amino-3-methoxy-1-propanol, quinidine and pseudoephedrine.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of the prodrug forms of the compounds of the present invention include the following esters:

methyl, ethyl, isopropyl,
methylcarbonyloxymethyl-, ethylcarbonyloxymethyl-,
t-butylcarbonyloxymethyl-,
cyclohexylcarbonyloxymethyl-,
1-(methylcarbonyloxy)ethyl-,
1-(ethylcarbonyloxy)ethyl-,
1-(t-butylcarbonyloxy)ethyl-,
1-(cyclohexylcarbonyloxy)ethyl-, i-propyloxycarbonyloxymethyl-,
cyclohexylcarbonyloxymethyl-,
t-butyloxycarbonyloxymethyl-,
1-(i-propyloxycarbonyloxy)ethyl-,
1-(cyclohexyloxycarbonyloxy)ethyl-,
1-(t-butyloxycarbonyloxy)ethyl-,
dimethylaminoethyl-, diethylaminoethyl-,
(5-methyl-1,3-dioxacyclopenten-2-on-4-yl)methyl-,
(5-(t-butyl)-1,3-dioxacyclopenten-2-on-4-yl)methyl-,
(1,3-dioxa-5-phenyl-cyclopenten-2-on-4-yl)methyl-,
1-(2-(2-methoxypropyl)-carbonyloxy)ethyl-.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| Boc | tert-butyloxycarbonyl |
| Boc$_2$O | di-tert-butyl dicarbonate |
| Cbz | benzyloxycarbonyl |
| DEC | 1-(3-dimethylaminopropyl)-3-ethylcarbodiimide hydrochloride |
| DIEA | diisopropylethylamine |
| DMAP | 4-dimethylaminopyridine |
| DMF | N,N-dimethylformamide |
| EtOAc | ethyl acetate |
| EtOH | ethyl alcohol |
| PLE | Pig liver esterase |
| pyr | pyridine |
| TBTU | 2-(1H-Benzotriazol-1-yl)-1,1,3,3-tetramethyluronium tetrafluoroborate |
| TFA | trifluoroacetic acid |
| THF | tetrahydrofuran |

Compounds of Formula I wherein the central heterocycle is a 1,3,4-thiadiazole ring can be conveniently prepared by cyclization of N,N'-diacylhydrazine in the presence of Lawessen reagent(M. P. Cava, et al, *Tetrahedron Lett.* 1985, 41, 5061) or P$_2$S$_5$(stelle, et al, *J. Prakt. Chem* 1904, 69, 145).

Scheme I illustrates one synthetic sequence which will provide the 1,3,4-thiadiazoles of this invention. An appropriately substituted ester is treated with hydrazine monohydrate to afford the hydrazide which is then converted to N,N'-diacylhydrazine on reaction with an acid chloride in aqueous THF using NaHCO3 as base. The N,N'-diacylhydrazine thus obtained is then cyclized to afford the 1,3,4-thiadiazole.

Subsequent hydrolysis of the ester using conventional methods known to one skilled in the art of organic synthesis gives the desired acid. Coupling of the resulting acid to appropriately substituted α- or β-amino esters affords an intermediate which can be deprotected to give compounds of Formula I. The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole.

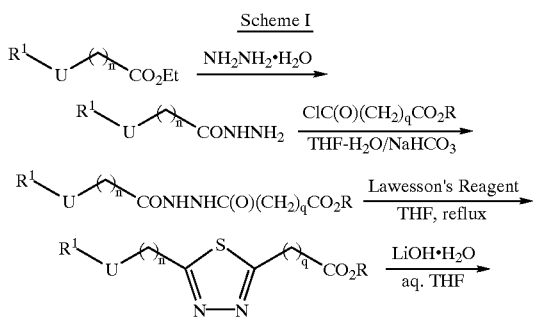

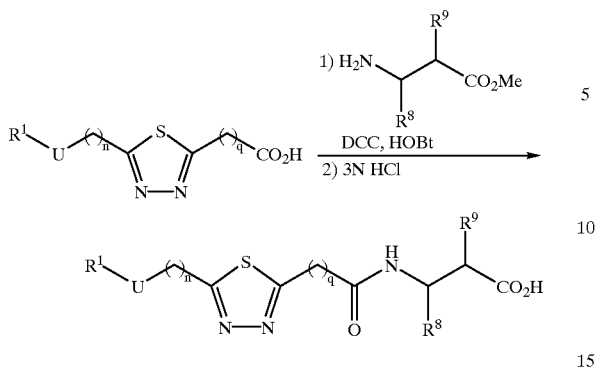
Alternately, as depicted in Scheme Ia and Ib, the above sequence can be carried out on an ester bearing a suitable functional group or protected functional group which can be converted into $R^1$ at a suitable stage of the synthesis of the target molecules.
Scheme Ia
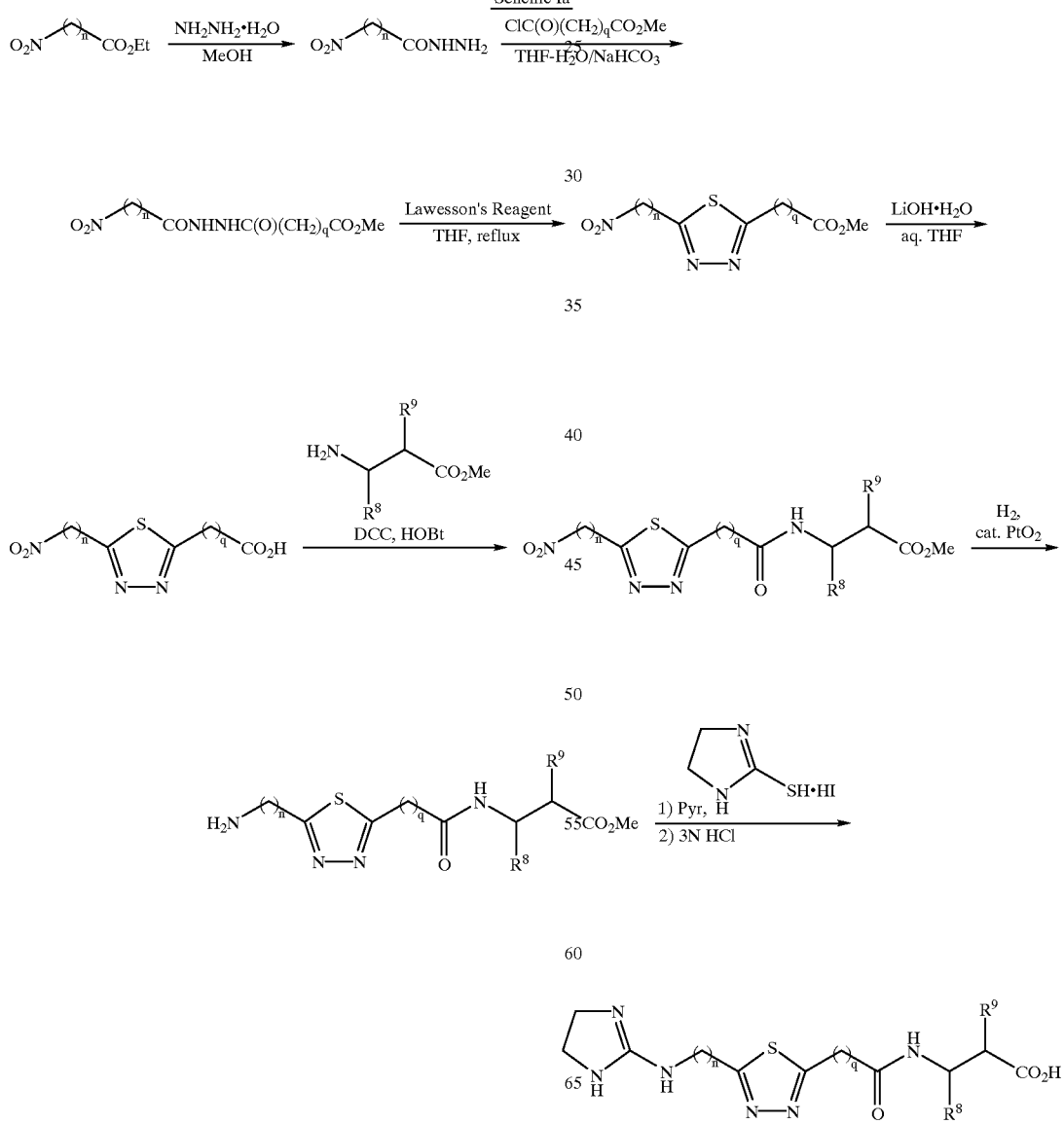

Scheme Ib

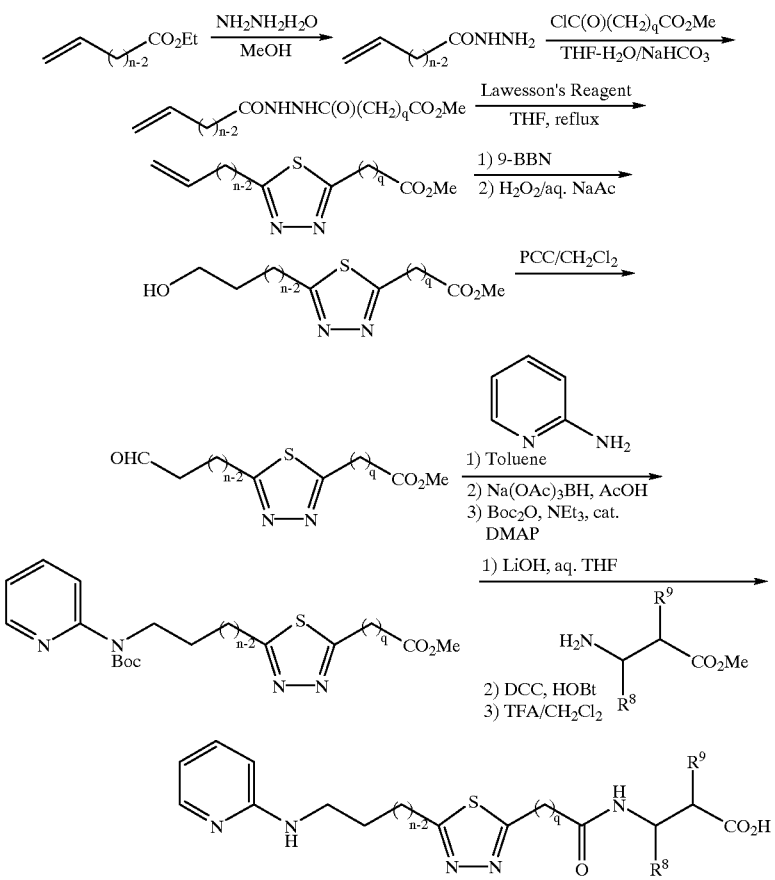

Additional 1,3,4-thiadiazolyl acids useful as starting materials for the preparation of compounds of Formula I, wherein W is —SCH$_2$C(=O)N(R$^{10}$)— can be prepared by substitution of a suitably substituted 1,3,4-thiadiazolyl sulfone with an acid thiol as shown in Scheme Ic using literature methods or modifications thereof. (Fujii et al, J. Pharm. Soc. Japan 1954, 74, 1056; Young et al, J. Am. Chem. Soc. 1955, 77, 400).

Scheme Ic

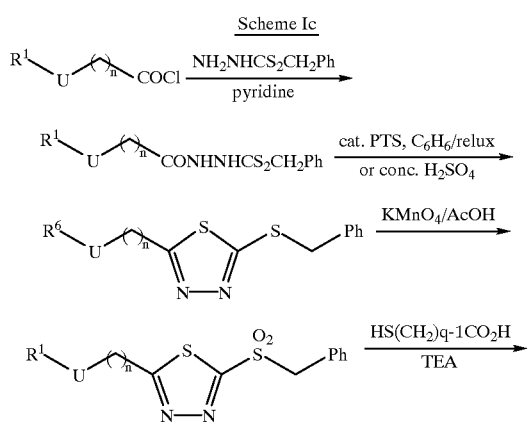

-continued

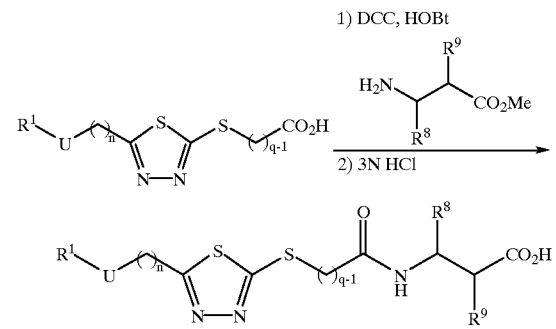

The appropriately substituted racemic b-amino acids may be purchased commercially or, as is shown in Scheme II, Method 1, prepared from the appropriate aldehyde, malonic acid and ammonium acetate according to the procedure of Johnson and Livak (J. Am. Chem. Soc. 1936, 58, 299). Racemic b-substituted-b-amino esters may be prepared through the reaction of dialkylcuprates or alkyllithiums with 4-benzoyloxy-2-azetidinone followed by treatment with anhydrous ethanol (Scheme I, Method 2) or by reductive amination of b-keto esters as is described in WO9316038. (Also see Rico et al., J. Org. Chem. 1993, 58, 7948–51.) Enantiomerically pure b-substituted-b-amino acids can be obtained through the optical resolution of the racemic mixture or can be prepared using numerous methods, including: Arndt-Eistert homologation of the corresponding a-amino acids as shown in Scheme II, Method 3 (see Meier, and Zeller, *Angew, Chem. Int. Ed. Engl.* 1975, 14, 32; Rodriguez, et al. Tetrahedron Lett. 1990, 31, 5153; Greenlee, *J. Med. Chem.* 1985, 28, 434 and references cited within); and through an enantioselective hydrogenation of a dehydroamino acid as is shown in Scheme II, Method 4 (see Asymmetric Synthesis, Vol. 5, (Morrison, ed.) Academic Press, New York, 1985). A comprehensive treatise on the preparation of b-amino acid derivatives may be found in patent application WO 9307867, the disclosure of which is hereby incorporated by reference.

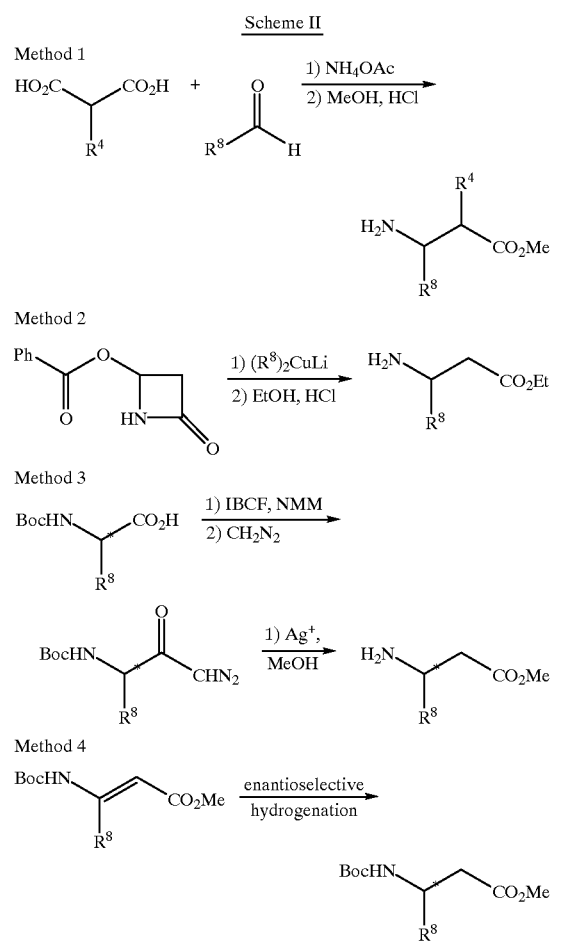

The synthesis of $N^2$-substituted diaminopropionic acid derivatives can be carried out via Hoffman rearrangement of a wide variety of asparagine derivatives as described in Synthesis, 266–267, (1981).

Synthesis of compounds of Formula I wherein the central heterocycle is a 1,3,4-oxadiazole ring, e.g. G=O, is shown in Scheme III. Cyclization of an appropriately substituted N,N'-diacylhydrazine in the presence of POCl₃ according to the method of Klingsberg (*J. Am. Chem. Soc.* 1958, 80, 5788) gives the intermediate 1,3,4-oxadiazolyl ester. This ester can be converted to compounds of Formula I using the methods described herein.

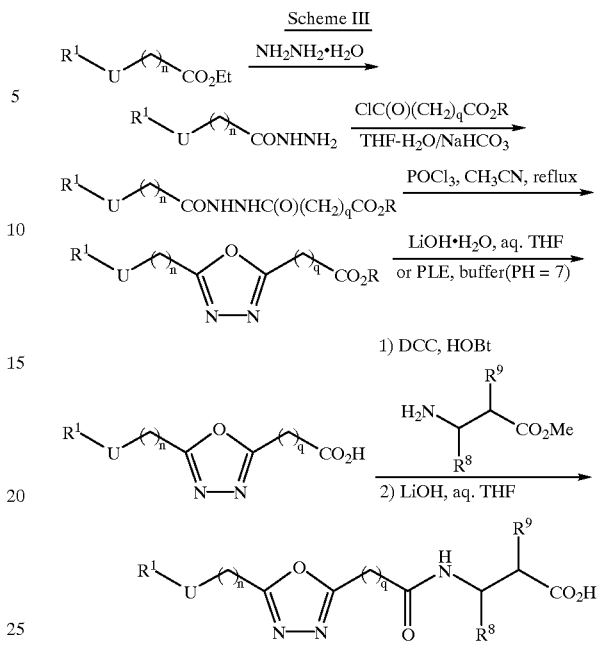

Alternately, the 1,3,4-oxadiazoles may be prepared from an ester bearing an appropriate functional group such as nitro or vinyl group which can be converted into $R^1$ at an appropriate stage of the synthesis of the target molecules.

Componds of formula I wherein G=O and W is —SCH₂C(=O)N(R¹⁰)— may be prepared from an appropriately substituted acylhydrazine adopting the method described by Confalone (*J. Am. Che. Soc.* 1983, 105, 902), as depicted in Scheme IV.

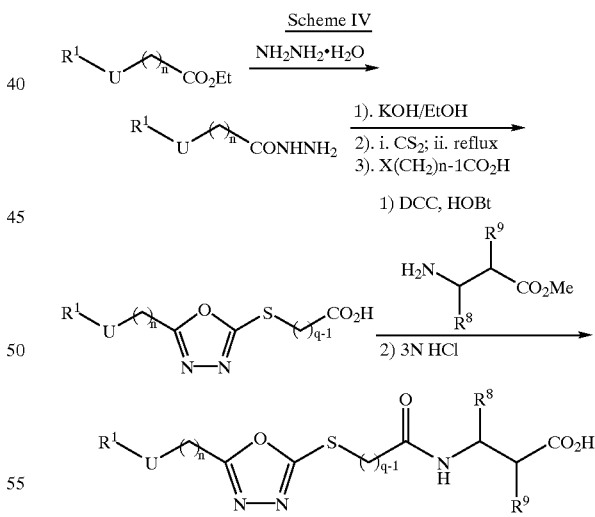

The detailed processes for preparing the compounds of Formula I are illustrated by the following Examples. It is, however, understood that this invention is not limited to the specific details of these examples. Melting points are uncorrected. Proton nuclear magnetic resonance spectra (¹H NMR) were measured in chloroform-d (CDCl₃) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multiplet.

EXAMPLE 43

2(S)-Phenylsulfonylamino-3-[2-[2-[3-[(N-imidazolin-2-yl)amino]propyl]-1,3,4-thiadiazol-5-yl]acetyl]aminopropionic acid Part A. 4-nitrobutyrylhydrazine Methyl 4-nitrobutyrate (5.5 g, 37.5 mmol) and hydrazine monohydrate (1.88 g, 37.5 mmol) were mixed in methanol (30ml). The resulting solution was stirred at rt for 50 hrs, and then evaporated under reduced pressure. The oily residue was pure enough for next reaction. $^1$H NMR(300 MHz) $\delta$2.08(qt, 2H), 2.20(t, 2H), 4.50(t, 2H); MS(HH$_3$-CI) Calc. for (M+1)$^+$:148. Found: 148.

Part B.N-(4—Nitrobutyryl)—N'(methoxycarbonylacetyl)hydrazine

To a suspesion of 4-nitrobutyrylhydrazine (5.5 g, 37.5 mmol) in aqueous THF (80 ml, 1:1 v/v) containing sodium bicarbonate (4.1 g, 48.8 mmol), cooled with ice-water, was added methyl malonyl chloride (6.1 g, 44.8 mmol) dropwise. After addition, the ice-water bath was removed and the mixture was stirred at rt for 2 hrs. The THF was evaporated under reduced pressure and the product as a solid powder was then collected by filtration and dried. (7.9 g, 85% yield). $^1$H NMR(300 MHz) $\delta$2.10(qt, 2H), 2.25(t, 2H), 3.34(s, 2H), 3.62(s,3H), 4.79(t, 2H), 10.02(s, 1H), 10.10(s, 1H); MS(NH$_3$-DCI) Calc. for (M+NH$_4$)$^+$: 265. Found: 265.

Part C. Methyl 2-[2-(3-nitropropyl)-1,3,4-thiadiazol-5-yl]acetate

A mixture of N-(4-nitrobutyryl)-N'-(methoxycarbonylacetyl)hydrazine (2.0 g, 8.1 mmol) and Lawesson's reagent (1.8 g, 4.4 mmol) in anhydrous THF (30 ml) was gently refluxed for 1 hr. The solution was then evaporated to dryness and the residue was dissolved in ethyl acetate and washed with saturated NaHCO3, brine, then dried. Evaporation followed by chromatography using a mixture of ethyl acetate and hexane (1:1. v:v) as eluent gave the product as an oil (1.1 g, 56% yield). $^1$H NMR(300 MHz) $\delta$2.60(qt, 2H), 3.24(t, 2H), 3.80(s, 3H), 4.10(s, 2H), 4.60(t, 2H); MS(NH$_3$-CI) Calc. for (M+1)$^+$: 246. Found: 246.

Part D. 2-[2-(3-nitropropyl)-1,3,4-thiadiazol-5-yl]acetic acid

Methyl 2-[2-(3-nitropropyl)-1,3,4-thiadiazol-5-yl]acetate (1.05 g, 4.3 mmol) was dissolved in aqueous THF (30 ml, 1:1, v:v) containing 450 mg (10.7 mmol) of LiOH.H2O. The solution was stirred at rt for 8 hrs, and then acidified with 6N HCl to a PH of around 2.0. The solution was evaporated to dryness and the residue was washed with acetone. After removal of acetone, the product was dried (800 mg, 81% yield). $^1$H NMR(300 MHz, DMSO) $\delta$2.34(qt, 2H), 3.16(t, 2H), 4.18(s, 2H), 4.68(t, 2H); MS(NH$_3$-CI) Calc. for (M+1)$^+$: 232. Found: 232.

Part E. Methyl N$^2$-Cbz-L-2,3-diaminopropionate HCl salt

N$^2$-Cbz-L-2,3-diaminopropionic acid (10 mmol, 2.39 g) was dissolved in 20 mL methanol and 20 mL 4 N HCl in dioxane and the solution was stirred for 4 hours and then concentrated to give a solid. The solid was washed with ether several times to give 2.50 g (87%) product. NMR (DMSO-d$_6$): d 8.38 (b, 3H); 7.96 (d, 1H); 7.38 (m, 5H); 5.05 (s, 2H); 4.44 (m, 1H); 3.66 (s, 3H); 3.14 (m, 2H).

Part F: Methyl N$^2$-Cbz—N$^3$-Boc-L-2,3-diaminopropionate

To a solution of methyl N$^2$-Cbz-(S)-2,3-diaminopropionate HCl salt (16.3 mmol, 4.7 g) and di-tert-butyl dicarbonate (16.3 mmol, 3.56 g) in 30 mL chloroform cooled in an ice bath was added triethylamine (34 mmol, 4.7 mL) and the solution was stirred in the ice bath for 1 hour and at room temperature for 3 hours and concentrated. The residue was taken up in ethyl acetate and the solution was washed with dilute citric acid, brine, NaHCO$_3$ and brine, dried (MgSO$_4$), and concentrated. Crystallization from ether/petroleum ether gave 5.2 g (92%) product. NMR (DMSO-d$_6$): d 7.60 (d, 1H); 7.35 (m, 5H); 6.88 (t, 1H); 5.02 (s, 2H); 4.14 (m, 1H); 3.60 (s, 3H); 3.28 (m, 2H); 1.37 (s, 9H).

Part G: Methyl N$^3$-Boc-(S)-2,3-diaminopropionate Formic acid salt

A mixture of methyl N$^2$-Cbz-N$^3$-Boc-(S)-2,3-diaminopropionate. (14 mmo, 5.0 g), formic acid (42 mmol, 1.6 mL) and 10% Pd/C (500 mg) in 40 mL methanol was stirred at room temperature for 1 hour and filtered through a celite. The filtrate was concentrated and the residue was triturated with ether-petroleum ether to give 3.7 g (100%) solid product. NMR (DMSO-d$_6$): $\delta$8.20(s, 1H); 6.90 (t, 1H); 5.36 (b, 3H); 3.61 9s, 3H); 3.51 (t, 1H); 3.18 (t, 2H); 1.38 (s, 9H).

Part H. Methyl N$^2$-phenylsulfonyl-N$^3$-Boc-(S)-2,3-diaminopropionate

To a mixture of methyl N$^3$-Boc-(S)-2,3-diaminopropionate HCO$_2$H salt (3.89, 14.7 mmol) and diisoproppylethylamine (3.3 g, 32.3mmol) in CH$_2$Cl$_2$ (60 ml), cooled with ice-water, was added phenylsulfonyl chloride (2.86 g, 16.22 mmol). After stirring at rt for 24 hrs, the resulting reaction mixture was diluted with ethyl acetate( 150 ml), washed with dilute citric acid, saturated NaHCO$_3$ and brine, and then dried. Concentration afforded the product as a foam(5.0 g, 95% yield). $^1$H NMR(300 MHz)$\delta$1.52(s, 9H), 3.46(m, 2H), 3.56(s, 3H), 4.00(m, 1H), 5.00(m, 1H), 5.74(d, 1H), 7.56(m, 3H), 7.82(m, 2H); MS(NH$_3$-CI) Calc. for (M+1)$^+$: 359. Found: 359.

Part I. Methyl N$^2$-phenylsulfonyl-3(S)-2,3-diaminopropionate HCl salt

Methyl N$^2$-phenylsulfonyl-N$^3$-Boc-(S)-2,3-diaminopropionate (4.5 g, 12.6 mmol) was dissolved in dioxane (8 ml) and then 4N HCl in dioxane (8 ml) was added. The resulting solution was stirred at rt for 5 hrs and then evaporated to give a foam (3.7 g, 100% yield). $^1$H NMR(300 MHz, DMSO-d$_6$)$\delta$2.78(m, 2H), 3.56(s, 3H), 3.68 (m, 1H), 5.70(d, 1H), 7.46(m, 3H), 7.68(m, 2H); MS(ESI) Calc. for (M+1)$^+$: 259. Found: 259(free base).

Part J. Methyl 2(S)-phenylsulfonyl-3-[2-[2-(3-nitropropyl)-1,3,4-thiadiazol-5-yl]acety]diaminopropionate To a mixture of 2-[2-(3-nitropropyl)-1,3,4-thiadiazol-5-yl]acetic acid (510 mg, 2.2 mmol), methyl N$^2$-phenylsulfonyl-(S)-2,3-diaminopropionate HCl salt (650 mg, 2.2 mmol) and triethylamine (1.35 ml, 8.8 mmol) in DMF (12 ml), cooled with ice-water, was added TBTU (700 g, 2.2 mmol). After stirring for 3 hrs, the reaction mixture was diluted with ethyl acetate and washed with dilute citric acid, dilute NaHCO$_3$ and brine successively, then dried. Concentration followed by chromatography using a mixture of ethyl acetate and hexane as the eluent gave the product as an amorphous solid (645 mg, 62% yield). $^1$H NMR(300 MHz)$\delta$2.58 (qt, 2H), 3.26(t, 2H), 3.54(m, 3H), 3.58(s, 3H), 3.70(m, 1H), 4.02(m, 1H), 4.08(s, 2H), 4.58(t, 2H), 5.76(d, 1H), 7.08(s, 7H), 7.549m, 3H), 7.80(m, 2H); MS(NH$_3$-CI) Calc. for (M+1)$^+$: 472. Found: 472.

Part K. Methyl 2(S)-phenylsulfonyl-3-[2-[2-(3-aminopropyl)-1,3,4-thiadiazol-5 yl]acety]diaminopropionate AcOH salt Methyl 2( S)-phenylsulfonyl-3-[2-[2-(3-nitropropyl)-1,3,4-thiadiazol-5-yl]acetyl]diaminopropionate (400 mg, 0.85 mmol) was dissolved in a mixed solvent of methanol and acetic acid (12 ml, 1:1, v:v) and PtO$_2$ (40 mg) was added. The resulting mixture was hydrogenated in a shaking bottle for 30 hrs, and then was filtered through a short column of Zeliot. The filtrate was concentrated and the residue dried to give an oily product (410 mg, 96% yield). $^1$H NMR(300 MHz, DMSO-d$_6$)δ2.76( qt, 2H), 3.08(t, 2H), 3.20(t, 2H), 3.34(s, 3H), 3.38(m, 2H), 3.90(m, 3H), 7.58(m, 3H), 7.749m, 2H), 8.749s, 1H); MS(NH$_3$-CI) Calc. for (M+1)$^+$: 442. Found: 442.

Part L. Methyl 2(S)-phenylsulfonyl-3-[2-[2-[3-[(N-imidazolin-2-yl)amino]propyl]-1,3,4-thiadiazol-5-yl]acetyl]diaminopropionate A solution of methyl 2(S)-phenylsulfonyl-3-[2-[2-(3-nitropropyl)-1,3,4-thiadiazol-5-yl]acetyl]diaminopropionate (425 mg, 0.85 mmol) and 2-methylthio-2-imidazoline hydriode (207 mg, 0.85 mmol) in pyridine (10 ml) was heated at 70° C. for 5 hrs. The solution was then concentrated and the residue was chromatographed using a mixture of methylene chloride and methanol as the eluent to afford an oily pruduct (250 mg, 58% yield).$^1$H NMR(300 MHz, CD$_3$OD)δ2.08(qt, 2H), 3.18(t, 2H), 3.30(m, 3H), 3.40(s, 3H), 3.54(dd, 1H), 3.66(s, 4H), 4.00(s, 2H)r 4.10(dd, 1H), 7.52(m, 3H), 7.80(m, 2H); MS(ESI) Calc. for (M+1)$^+$: 510. Found: 510.

Part M. 2(S)-phenylsulfonyl-3-[2-[2-[3-[(N-imidazolin-2-yl)amino]propyl]-1,3,4-thiadiazol-5-yl]acetyl]diaminopropionic acid HCl salt Methyl 2(S)-phenylsulfonyl-3-[2-[2-[3-[(N-imidazolin-2-yl)amino]propyl]-1,3,4-thiadiazol-5-yl]acetyl]diaminopropionate (230 mg, 0.45 mmol) was dissolved in 4N HCl (9 ml) and the solution was stirred at rt for 40 hrs, then concentrated under reduced pressure to dryness to afford the product as an amorphous solid (200 mg, 91% yield). Further puriofication via reverse phase HPLC using a mixture of acetonitrile and 0.1% TFA in water as the eluent gave the test sample. $^1$H NMR(300 MHz, DMSO-D$_6$)δ1.96 (qt, 2H), 3.08(t, 2H), 3.24(m, 3H), 3.40(m, 1H), 3.90(m, 3H), 7.56(m, 3H), 7.58(m, 2H), 8.22(d, 1H), 8.46(t, 1H), 8.56(t, 1H); MS(ESI) Calc. for (M+1)$^+$: 496. Found: 496.

EXAMPLE 44

2(S)-(3-methylphenylsulfonyl)amino-3-[2-[2-[3-[(N-imidazolin-2-yl)amino]propyl]-1,3,4-thiadiazol-5-yl]acetyl]aminopropionic acid Part A. Methyl N$^2$-3-methylphenylsulfonyl-N$^3$-Boc-(S)-2,3-diaminopropionate To a mixture of methyl N$^3$-Boc-(S)-2,3-diaminopropionate HCO$_2$H salt (3.8 g, 14.7 mmol) and diisoproppylethylamine (3.3 g, 32.3 mmol) in CH$_2$Cl$_2$ (60 ml), cooled with ice-water, was added 3-methylsulfonyl chloride (3.1 g, 16.2 mmol). After stirring at rt for 24 hrs, the resulting reaction mixture was diluted with ethyl acetate (150 ml), washed with dilute citric acid, saturated NaHCO$_3$ and brine, and then dried. Concentration afforded the product as a foam (5.1 g, 95% yield). $^1$H NMR(300 MHz, CDCl$_3$)δ1.58(s, 9H), 2.30(s, 3H), 2.72(m, 1H), 2.98(m, 1H), 4.10(m, 1H), 5,80(s, 1H), 7.40(d, J=5, 2H), 7.50(m, 1H), 7.56(s, 1H), 8.40(d, J=6, 1H); MS(NH$_3$-CI) Calc. for (M+1)$^+$: 373. Found: 373.

Part B. Methyl N$^2$-3-methylphenylsulfonyl-(S)-2,3-diaminopropionate HCl salt

Methyl N$^2$-3-methylphenylsulfonyl-N$^3$-Boc-(S)-2,3-diaminopropionate (4.5 g, 12.1 mmol) was dissolved in dioxane (8 ml) and then 4N HCl in dioxane (8 ml) was added. The resulting solution was stirred at rt for 5 hrs and then evaporated to give a foam (3.7 g, 100% yield). $^1$H NMR(300 MHz, DMSO-d$_6$)δ2.40(s, 3H), 2.86(m, 1H), 3.10 (m, 1H), 3.40(s, 3H), 4.28(m, 1H), 7.48(d,J=5 2H), 7.60(m, 1H), 7.62(s, 1H) 8.39(s, broad, 2H), 8.62(d, J=6, 1H); MS(ESI) Calc. for (M+1)$^+$: 273. Found: 273 (free base).

Part C. Methyl 2(S)-(3-methylphenyl)sulfonylamino-3-[2-[2-(3-nitropropyl)-1,3,4-thiadiazol-5 yl]acetyl]aminopropionate To a mixture of 2-[2-(3-nitropropyl)-1,3,4-thiadiazol-5-yl]acetic acid (430 mg, 1.86 mmol), methyl N$^2$-3-methylphenylsulfonyl-(S)-2,3-diaminopropionate HCl salt (630 mg, 2.0 mmol) and triethylamine (1.1 ml, 8.2 mmol) in DMF (10 ml), cooled with ice-water, was added TBTU (660 mg, 2.0 mmol). After stirring for 3 hrs, the reaction mixture was diluted with ethyl acetate and washed with dilute citric acid, dilute NaHCO$_3$ and brine successively, then dried. Concentration followed by chromatography using a mixture of ethyl acetate and hexane as the eluent gave the product as an amorphous solid (360 mg, 40% yield).$^1$H NMR(300 MHz)δ2.40(s, 3H), 2.58(qt, 2H), 3.269t, 2H), 3.52(s, 3H), 3.62(m, 2H), 4.06(m, 1H), 4.10(s, 2H), 4.59(t, 2H), 7.36(m, 2H), 7.60(m, 2H); MS(NH$_3$-CI) Calc. for (M+1)$^+$: 486. Found: 486.

Part D. Methyl 2(S)-(3-methylphenyl)sulfonylamino-3-[2-[2-(3-aminopropyl)-1,3,4-thiadiazol-5-yl]acety]aminopropionate AcOH salt Methyl 2(S)-(3-methylphenyl)sulfonylamino-3-[2-[2-(3-nitropropyl)-1,3,4-thiadiazol-5-yl]acetyl]aminopropionate (140 mg, 0.29 mmol) was dissolved in a mixed solvent of methanol and acetic acid (20 ml, 1:1, v:v) and PtO$_2$(30 mg) was added. The resulting mixture was hydrogenated in a shaking bottle for 24 hrs, and then was filtered through a short column of Zeliot. The filtrate was concentrated and the residue dried to give an oily product (120 mg, 91% yield). $^1$H NMR(300 MHz, DMSO-d$_6$)δ1.90(qt, 3H), 2.56(s, 3H), 2.78(t, 2H), 3.10(t, 2H), 3.28(s, 3H), 3.36(m, 2H), 3.84(m, 3H), 7.30(m, 2H), 7.42(m, 1H), 7.74(d, 1H), 8.58(s, 1H); MS(ESI) Calc. for (M+1)$^+$: 456. Found: 456.

Part E. Methyl 2(S)-(3-methylphenyl)sulfonylamino-3-[2-[2-[3-[(N-imidazolin-2-yl)amino]propyl]-1,3,4-thiadiazol-5-yl]acety]aminopropionate A solution of methyl 2(S)-(3-methylphenyl)sulfonylamino-3-[2-[2-(3-nitropropyl)-1,3,4-thiodiazol-5-yl]acetyl]aminopropionate (130 mg, 0.29 mmol) and 2-methylthio-2-imidazoline hydriode (78 mg, 0.32 mmol) in pyridine (5 ml) was heated at 70° C. for 5 hrs. The solution was then concentrated and the residue was chromatographed using a mixture of methylene chloride and methanol as the eluent to afford an oily pruduct (90 mg, 59% yield).$^1$H NMR(300 HMz, DMSO-d$_6$)δ1.90(qt, 3H), 2.56(s, 3H), 3.04 (t, 2H), 3.20(m, 2H), 3.28(s, 3H), 3.58(m, 2H), 3.56(m, 4H), 3.84(m, 3H), 7.30(m, 2H), 7.42(m, 1H), 7.74(d, 1H), 8.24(s, 1H), 8.46(s, 1H); MS(ESI) Calc. for (M+1)$^+$: 524. Found: 524.

Part F. 2(S)-(3-methylphenyl)sulfonylamino-3-[2-[2-[3-[(N-imidazolin-2-yl)amino]propyl]-1,3,4-thiadiazol-5-yl]acety]aminopropionic acid HCl salt Methyl 2(S)-(3-methylphenyl)sulfonylamino-3-[2-[2-[3-[(N-imidazolin-2-yl)amino]propyl]-1,3,4-thiadiazol-5-yl]acety]aminopropionate (80 mg, 0.15 mmol) was dissolved in 4N HCl (6 ml) and the solution was stirred at rt for 36 hrs, then concentrated under reduced pressure to dryness, affording the product as an amorphous solid (75 mg, 97% yield). Further puriofication via reverse phase HPLC using a mixture of acetonitrile and 0.1% TFA in water as the eluent gave the test sample. $^1$H NMR(300 MHz, DMSO-D$_6$)δ2.96(qt, 2H), 2.60(s, 3H), 3.08(t, 2H), 3.20(m, 3H), 3.40(m, 1H), 3.58(s, 4H), 3.94(m, 3H), 7.30(m, 3H), 7.42(m, 1H), 7.58(m, 2H), 8.20(d, 1H), 8.38(t, 1H), 8.50(m, 1H); MS(ESI) Calc. for (M+1)$^+$: 510. Found: 510.

EXAMPLE 176

2(S)-Benzyloxycarbonylamino-3-[[2-[4-[N-(pyridin-2-yl)amino]butyl]-1,3,4-thiadiazol-5-yl]carbonyl]aminopropionic acid TFA salt Part A. Pent-4-enoyl hydrazide A mixture of pent-4-enoic acid ethyl ester (12.1 g, 94.5 mmol) and hydrazine monohydrate (4.6 ml, 94.5 mmol) in methanol (75 ml) was stirred at rt for 48 hrs. The volatile portion of the reaction mixture was then removed. The product was obtained as an oil (9.5 g, 94% yield). $^1$H NMR(300 MHz)δ1.56(m, 2H), 2.30(t, 2H), 5.20(m, 2H), 5.80(m, 1H); MS(NH$_3$-CI) Calcd. for (M+1)$^+$: 115. Found: 115

Part B. N-(Pent-4-enoic)-N'-(methoxycarbonylcarbonyl)hydrazine

To a solution of pent-4-enoic hydrazine (10.8 g, 94.5 mmol) in aqueous THF (80 ml, 1:1, v:v) containing NaHCO$_3$ (11.9 g, 141.7 mmol) cooled in an ice-water bath was added methyl oxalyl chloride (13.0 ml, 141.7 mmol) dropwise. After addition, the mixture was stirred in the ice-water bath for additional 30 mins, and then at rt overnight. The THF was removed under reduced pressure and the aqueous residue was extracted with ethyl acetate. The ethyl acetate solution was washed with brine and then dried over Na$_2$SO$_4$. Concentration afforded the product as an oil (12.3 g, 65% yield). $^1$H NMR (300 MHz)δ1.60(qt, 2H), 2.44(t, 2H), 3.96(s, 3H), 5.10(m, 2H), 5.80(m, 1H); MS(NH$_3$-CI) Calcd. for (M+1)$^+$: 201. Found: 201.

Part C. Methyl [2-(but-3-enyl)-1,3,4-thiadiazol-5-yl]carboxylate

N-(Pent-4-enoic)-N'-(methoxycarbonylcarbonyl)hydrazine (2.13 g, 10.6 mmol) was dissolved in anhydrous THF (20 ml) and then was heated to gentle refluxing. Lawesson reagent (2.15 g, 5.3 mmol) was introduced and stirring was continued under such conditions for 3 hrs. The solvent was removed under reduced pressure and the residue was dissloved in ethyl acetate, washed with saturated NaHCO$_3$ and brine, then dried over Na$_2$SO$_4$. After removal of ethyl acetate, the residue was chromatographed using a mixture of ethyl acetate and hexane as the eluent to give the product as a white solid (1.5 g, 73% yield). $^1$H NMR(300 MHz)δ2.60(qt, 2H), 3.32(t, 2H), 4.06(s, 3H), 5.14(m, 2H), 5.84(m, 1H); MS(NH$_3$-CI) Calcd. for (M+1)$^+$: 199. Found: 199.

Part C. Methyl [2-(4-hydroxybutyl)-1,3,4-thiadiazol-5-yl]carboxylate

Methyl [2-(but-3-enyl)-1,3,4-thiadiazol-5-yl]carboxylate (420 mg, 2.13 mmol) was dissolved in anhydrous THF (5 ml) and then cooled with an ice-water bath to 0° C. 9-BBN (290 mg, 2.34 mmol) dissolved in THF (5 ml) was introduced and the resulting reaction mixture was kept stirring at 0° C. for 3 hrs, then at rt for 5 hrs. NaOAc (1 g) dissolved in water (5 ml) was added, followed by introduction of 1 ml of 30% H$_2$O$_2$. After stirred further at rt for 2 hrs, the mixture was extracted with ethyl acetate. The extract was washed with brine and then dried over Na$_2$SO$_4$. Concentration followed by chromatography using ethyl acetate as the eluent yielded the product as a white powder (420 mg, 92% yield). $^1$H NMR(300 MHz)δ1.64(m, 2H), 1.90(m, 2H), 3.24(t, 2H), 3.76(q, 2H), 3.82(t, 1H), 4.06(s, 1H); MS(NH$_3$-CI) Calcd. for (M+1)$^+$: 217. Found: 217.

Part D. Methyl [2-(4-oxobutyl)-1,3,4-thiadiazol-5-yl]carboxylate

Methyl [2-(4-hydroxybutyl)-1,3,4-thiadiazol-5-yl]carboxylate (210 mg, 0.97 mmol) was dissloved in CH$_2$Cl$_2$, followed by introduction of PCC (314 mg, 1.45 mmol). The mixture was stirred at rt for 5 hrs, and then was filtered through a short column of silica gel. The filtrate was concentrated and the residue was chromatographed using a mixture of ethyl acetate and hexane as the eluent to give 110 mg of the product (53% yield) as a white solid. $^1$H NMR(300 MHz)δ2.20(qt, 2H), 2.66(t, 2H), 3.26(t, 2H), 4.04(s, 3H), 9.72(s, 1H); MS(NH$_3$-CI) Calcd. for (M+1)$^+$: 215. Found: 215.

Part E. Methyl [2-4-[N-Boc—N-(pyridin-2-yl)amino]butyl]-1,3,4-thiadiazol-5-yl]carboxylate Methyl [2-(4-oxobutyl)-1,3,4-thiadiazol-5-yl]carboxylate (100 mg, 0.47 mmol) and 2-aminopyridine (48 mg, 0.52 mmol) were dissolved in anhydrous toluene (4 ml) and then were heated at 70° C. for 2 hrs, during which time a small amount of pulverised molecular sieve was added. HOAc (30 ul, 0.52 mmol) and NaB(OAc)$_3$H were added. Stirring was continued at rt for 18 hrs. NaOAc (300 mg) dissolved in 10 ml of water was added and the mixture was diluted with another 10 ml of water after being stirred for additional 2 hrs. The solution was extracted with CH$_2$Cl$_2$ and the extract was concentrated and dried.

The oily product obtained above was then dissolved in dry CHCl$_3$(5 ml), and cooled in an ice-water bath, followed by addition of triethylamine(0.13 ml, 0.94 mmol), Boc2O(153 mg, 0.71 mmol) and a catalytic amount of DMAP. The mixture was stirred at rt for 24 hrs, and then diluted with ethyl acetate. The solution was washed with dilute citric acid, saturated NaHCO$_3$ and brine successively, and then dried over Na$_2$SO$_4$. Concetration followed by chromatography using a mixture of ethyl acetate and hexane as the eluent afforded the product as an oil (85 mg, 46% yield in two steps). $^1$H NMR(300 MHz)δ1.50(s, 9H), 1.79(qt, 2H), 1.84(qt, 2H), 3.20(t, 2H), 4.00(t, 2H), 4.04(s, 3H), 7.00(m, 1H), 7.60(m, 2H), 8.38(m, 1H); MS(NH$_3$-CI) Calcd. for (M+1)$^+$: 393. Found: 393.

Part E. [2-[4-[N-Boc-N-(pyridin-2-yl)amino]butyl]-1,3,4-thiadiazol-5-yl]carboxylic acid Methyl [2-[4-[N-Boc-N-(pyridin-2-yl)amino]butyl]-1,3,4-thiadiazol-5-yl]carboxylate (80 mg, 0.20 mmol) dissolved in 0.2 ml of DMSO was mixed with PLE(50 mg) and buffer solution (PH=7.00, 4 ml) and the mixture was vigorously stirred at rt for 18 hrs, and then was evaporated under high vaccum. The resulting solid was extracted with ethyl acetate and the extract was concentrated to give an oil (60 mg, 78% yield). $^1$H NMR(300 MHz)δ1.52(s, 9H), 1.80(qt, 2H), 1.86 (qt, 2H), 3.22(t, 2H), 4.00(t, 2H), 7.10(m, 1H), 7.64(m, 2H), 8.30(m, 1H); MS(ESI) Calcd. for (M+1)$^+$: 379. Found: 379.

Part F. t-butyl 2(S)-benzyloxycarbonylamino-3-aminopropionate

Conc. H2SO4(8 ml) was added to dioxane(120 ml) in a Parr Bottle cooled with dry ice, followed by addition of 2(S)-benzyloxycarbonylamino-3-aminopropionic acid (6.88 g, 28.8 mmol) and pre-condensed isobutylene (130 ml, excess). The mixture in the Parr bottlle was then shaked at rt for 70 hrs. After removal of isobutylene under reduced pressure, the resulting solution was poured into a NaOH solution containing NaOH (17.4 g) and ether (400 ml) cooled in an ice water bath while stirred vigorously. The etheral layer was separated and the aqueous layer was extracted with ether. The combined etheral solution was washed with 1N HaOH twice and then dried over Na$_2$SO$_4$. Concetration gave the product as a solid (6.3 g, 75% yield). $^1$H NMR(300 MHz)δ1.44(s, 9H), 3.10(m,2H), 4.26(m, 1H), 5.12(s, 2H), 5.80(d, 1H), 7.36(m, 5H); MS(NH$_3$-CI) Calcd. for (M+1)$^+$: 293. Found: 293.

Part G. t-Butyl 2(S)-Benzyloxycarbonylamino-3-[[2-[4-[N-Boc-N-(pyridin-2-yl)amino]butyl]-1,3,4-thiadiazol-5-yl]carbonyl]aminopropionate To a mixture of [2-[4-[N-Boc-N-(pyridin-2-yl)amino]butyl]-1,3,4-thiadiazol-5-yl]carboxylic acid (50 mg, 0.13 mmol), t-butyl 2(S)-benzyloxycarbonylamino-3-aminopropionate (40 mg, 0,13 mmol) and triethylamine (40 ul, 0.29 mmol) in EtOAc(4 ml), was added PyBop (75 mg, 0.13 mmol). After stirring for 4 hrs at rt, the reaction mixture was diluted with ethyl acetate and washed with dilute citric acid, dilute NaHCO$_3$ and brine successively, then dried. Concentration followed by chromatography using a mixture of ethyl acetate and hexane as the eluent gave the product as an amorphous solid (30 mg, 35% yield).$^1$H NMR(300 MHz)δ1.46(s, 9H), 1.50(s, 9H), 1.80(m, 4H), 3.19(t, 2H), 3.87(m, 2H), 4.00(t, 2H), 4.44(m, 1H), 5.12(s, 2H), 5.68(d, 1H), 7.00(m, 1H), 7.36(m, 5H), 7.60(m, 2H), 8.40(m, 1H); MS(ESI) Calc. for (M+1)$^+$: 655. Found: 655.

Part H. 2(S)-Benzyloxycarbonylamino-3-[[2-[4-[N-(pyridin-2-yl)amino]butyl]-1,3,4-thiadiazol-5-yl]carbonyl]aminopropionic acid TFA salt t-Butyl 2(S)-Benzyloxycarbonylamino-3-[[2-[4-[N-Boc-N-(pyridin-2-yl)amino]butyl]-1,3,4-thiadiazol-5-yl]carbonyl]aminopropionate (30 mg, 0.046 mmol) was dissolved in CH$_2$Cl$_2$(5 ml) containing 0.25 ml of TFA. The solution was stirred at rt for 24 hrs and then conceatrated, affording an oily product (20 mg, 87% yield). Further purification by reverse HPLC using a mixture of acetonitrile and 0.1% TFA in water gave the sample for testing. $^1$H NMR(300 MHz)δ1.68(qt, 2H), 1.84(qt, 2H), 3.20(t, 2H), 3.36(m, 2H), 3.64(t, 2H), 4.25(m, 1H), 5.02(s, 2H), 6.84(t, 1H), 7.04(d, 1H), 7.54(m, 5H), 7.70(m, 1H), 7.90(m, 2H), 8.80(m, 1H), 9.20(t, 1H); MS(ESI) Calc. for (M+1)$^+$: 499. Found: 499.

EXAMPLE 178

2(S)-(2,4,6-Trimethylphenylsulfonyl)amino-3-[[2-[4-[N-(pyridin-2-yl)amino]butyl]-1,3,4-thiadiazol-5-yl]carbonyl]aminopropionic acid TFA salt Part A. 2-N-Mesitylenesufonyl-L-asparigine L-Asparagine (8.5 g, 56.8 mmol) was dissolved in water (23 ml) containing triethylamine (19.8 ml). Thi mixture was then diluted with dioxane (40 ml). To the resulting mixture was added slowly 2-mesitylenesulfonyl chloride (14.85 g) dissolved in dioxane (50 ml), causing a little exothermic. After addition, the mixure was stirred further at rt for 24 hrs. The reaction mixture was evaporated to remove most of the organic solvent, and then basified with 2N HaOH. The basic solution was extracted with CH2Cl2(50 ml×2) and filtered. The filtrate was acidified with concentrated HCl. The solid formed was collected by filtration (13.0 g, 73%yield). $^1$H NMR(300 MHz,CDCl$_3$)δ2.24(s, 3H), 2.30(dd, 1H), 2.43(dd, 1H), 2.54(s, 6H), 4.00(m, 1H), 6.86(s, 1H), 7.00(s, 2H), 7.32(s, 1H), 7.80(d, 1H); MS(ESI) Calc. for (M+1)$^+$: 315. Found: 315.

Part B. 2(S)-(2,4,6-Trimethylphenylsulfonyl)amino-3-aminopropionic acid

Bromine (1.04 ml, 20.1 ml) was added to a solution of 4N NaOH(34 ml) cooled in an ice-water bath. The orange solution was stirred in the ice bath for additional 15 mins and then 2-N-Mesitylenesufonyl-L-asparigine (5.3 g, 16.8 mmol) was added in portions. Stirring was continued in the ice bath for 15 mins and then at 85° C. for 1 hr. The resulting solution was cooled in an ice bath and acidified with conc. HCl to PH ~6. The solid was collected through filtration (4,7 g, 97% yield). $^1$H NMR(300 MHz, DMSO-d$_6$)δ2.20(s, 3H), 2.48(s, 6H), 2.76(t, 1H), 2.92(m, 1H), 3.04(m, 1H), 6.98(s, 1H), 7.00(s, 2H); MS(ESI) Calc. for (M+1)$^+$: 287. Found: 287.

Part C. t-Butyl 2(S)-(2,4,6 trimethylphenylsulfonyl) amino-3-aminopropionate

Conc. H2SO4 (7.7 ml) was added to dioxane (120 ml) in a Parr Bottle cooled with dry ice, followed by addition of 2(S)-(2,4,6-trimethylphenylsulfonyl)amino-3-aminopropionic acid(8,02 g, 28 mmol) and pre-condensed isobutylene (136 ml, excess). The mixture in the Parr bottlle was then shaked at rt for 70 hrs. After removal of isobutylene under reduced pressure, the resulting solution was poured into a NaOH solution containing NaOH(11.9 g) and ether (400 ml) cooled in an ice water bath while stirred vigorously. The etheral layer was separated and the aqueous layer was extracted with ether. The combined etheral solution was washed with 1N HaOH twice and then dried over Na$_2$SO$_4$. Concetration gave the product as a solid(7.7 g, 81% yield). $^1$H NMR(300 MHz)δ1.56(s, 9H), 2.20(s, 3H), 2.48(s, 6H), 2.76(t, 1H), 2.92(m, 1H), 3.04(m, 1H), 6.98(s, 1H), 7.00(s, 2H) ; MS(NH$_3$-Cl) Calcd. for (M+1)$^+$: 343. Found: 343.

Part D. t-Butyl 2(S)-(2,4,6-trimethylphenylsulfonyl) amino-3-[2-[4-[N-Boc—N-(pyridin-2-yl)amino]butyl]-1,3,4-thiadiazol-5-yl]carbonyl]aminopropionate To a mixture of [2-[4-[N-Boc-N-(pyridin-2-yl)amino]butyl]-1,3,4-thiadiazol-5-yl]carboxylic acid (135 mg, 0.36 mmol), t-butyl 2(S)-(2,4,6-trimethylphenylsulfonyl)amino-3-aminopropionate (120 mg, 0.36 mmol) and triethylamine (0.25 ml, 1.8 mmol) in DMF(8 ml), was added PyBop (210 mg, 0.36 mmol). After stirring for 4 hrs at rt, the reaction mixture was diluted with ethyl acetate and washed with dilute citric acid, dilute NaHCO$_3$ and brine successively, then dried. Concentration followed by chromatography using a mixture of ethyl acetate and hexane as the eluent gave the product as an amorphous solid (150 mg, 64% yield).$^1$H NMR(300 MHz, CDCl$_3$)δ1.32(s, 9H), 1.50(s, 9H), 1.82(m, 4H), 2.24(s, 3H), 2.64(s, 6H), 3.20(t, 2H), 3.66(m, 1H), 3.80(m, 1H), 4.00(m, 3H), 5.60(d, 1H), 6.90(s, 2H), 7.00(m, 1H), 7.60(m, 2H), 8.40(m, 1H); MS(ESI) Calc. for (M+1)$^+$: 703. Found: 703.

Part E. 2(S)-(2,4,6-Trimethylphenylsulfonyl)amino-3-[[2-[4-[N-(pyridin-2-yl)amino]butyl]-1,3,4-thiadiazol-5-yl]carbonyl]aminopropionic acid TFA salt t-Butyl 2(S)-(2,4,6 trimethylphenylsulfonyl) amino-3-[[2-[4-[N-Boc-N-(pyridin-2-yl)amino]butyl]-1,3,4-thiadiazol-5-yl]carbonyl]aminopropionate (60 mg, 0.091 mmol) was dissolved in CH$_2$Cl$_2$(5 ml) containing 0.25 ml of TFA. The solution was stirred at rt for 24 hrs and then concetrated, affording an oily product (42 mg, 90% yield). Further purification by reverse HPLC using a mixture of acetonitrile and 0.1% TFA in water gave the sample for testing. $^1$H NMR(300 MHz, DMSO-d$_6$)δ1.64(qt, 2H), 1.80(qt, 2H),2.12 (s, 3H), 2.46(s, 6H), 3.18(t, 2H), 3.30(m, 2H), 3.50(m, 2H), 3.98(m, 1H), 6.80(s, 2H), 6.84(t, 1H), 7.00(d, 1H), 7.86(m, 2H), 8.02(d, 1H), 8.76(s, 1H), 8.94(t, 1H); MS(ESI) Calc. for (M+1)$^+$: 547. Found: 547.

EXAMPLE 179

2(S)-(1-Naphthalenesulfonyl)amino-3-[[2-[4-[N-(pyridin-2-yl)amino]butyl]-1,3,4-thiadiazol-5-yl]carbonyl]aminopropionic acid TFA salt This compound was analogously prepared to Example 178. $^1$H NMR(300 MHz, DMSO-d$_6$)δ1.64(qt, 2H), 1.80(qt, 2H), 3.18(t, 2H), 3.34(m, 2H), 3.44(m, 2H), 3.90(m, 1H), 6.80(t, 1H), 7.00(d, 1H), 7.50(m, 3H), 7.88(m, 3H), 8.06(d, d, 2H), 8.56(d, 2H), 8.76(s, 1H), 8.84(t, 1H); MS(ESI) Calc. for (M+1)$^+$: 555. Found: 555.

EXAMPLE 321

2(S)-Benzyloxycarbonylamino-3-[[2-[4-[(N-imidazolin-2-yl)amino]butyl]-1,3,4-thiadiazol-5-yl]carbonyl]aminopropionic acid TFA salt Part A. Methyl [2-(4-triazobutyl)-1,3,4-thiadiazol-5-yl] carboxylate Mesyl chloride(0.26 mL, 3.34 mmol) was added slowly to a solution of methyl [2-(4-hydroxybutyl)-1,3,4-thiadiazol-5-yl]carboxylate (600 mg, 2.78 mmol) and triethylamine (0.77 ml, 5.56 mmol) in $CH_2Cl_2$ cooled in a ice-water bath. After addition, the resulting mixture was stirred for additional 30 mins. The reaction mixture was diluted with ethyl acetate and then washed with aqueous citric acid, saturated $NaHCO_3$ and brine. Concentration and chromatography with a mixture of ethyl acetate and hexane gave the mesylate as an oil (530 mg).

The mesylate was dissolved in DMF(10 ml). Sodium triazide(585 mg, 9.0 mmol) was added. The mixture was heated at 40° C. for 4 hrs. After dilution with ethyl acetate, the organic solution was washed with saturated $NaHCO_3$, brine and then dried over $Na_2SO_4$. Concetration and Chromatography with a mixture of ethyl aceate and hexane gave 450 mg of the product as an oil (67% yield). $^1$H NMR(300 MHz, $CDCl_3$)δ1.74(m, 2H), 1.96(m, 2H), 3.24(t, 2H), 3.38 (t, 2H),4.06(s, 1H); MS($NH_3$-CI) Calcd. for (M+1)$^+$: 242. Found: 242.

Part B. [2-(4-triazobutyl)-1,3,4-thiadiazol-5-yl]carboxylic acid

Methyl [2-[4-triazobutyl]-1,3,4-thiadiazol-5-yl] carboxylate (300 mg, 1.24 mmol) was mixed with PLE-A (200 mg) and buffer solution(PH=7.00, 10 ml). The mixture was vigorously stirred at rt for 36 hrs, and then evaporated under high vaccum to dryness. The residue was extracted with methanol and the extract was concentrated to give the aciod as an oil (190 mg, 70% yield). $^1$H NMR(300 MHz, DMSO-$d_6$)δ1.58(m, 2H), 1.76(m, 2H), 3.00(t, 2H), 3.40(t, 2H); MS(ESI) Calcd. for (M+1)$^+$: 228. Found: 228.

Part C. t-Butyl 2(S)-benzyloxycarbonylamino-3-[[2-(4-triazobutyl)-1,3,4-thiadiazol-5-yl]carbonyl]aminopropionate To a mixture of [2-(4-triazobutyl)-1,3,4-thiadiazol-5-yl] carboxylic acid(270 mg, 1.2 mmol), t-butyl 2(S)-benzyloxycarbonylamino-3-aminopropionate (350 mg, 0,13 mmol) and triethylamine (40 ul, 1.2 mmol) in DMF(10 ml), was added PyBop(700 mg, 1.2 mmol). After stirring for 4 hrs at rt, the reaction mixture was diluted with ethyl acetate and washed with dilute citric acid, dilute $NaHCO_3$ and brine successively, then dried. Concentration followed by chromatography using a mixture of ethyl acetate and hexane as the eluent gave the product as an amorphous solid(440 mg, 90% yield).$^1$H NMR(300 MHz, $CDCl_3$)δ1.40(s, 9H), 1.74 (m, 2H), 1.85(m, 2H), 3.20(t, 2H), 3.26(t, 2H), 3.88(m, 2H), 4.10(m, 1H), 5.12(S, 2H), 5.80(s, 1H), 7.38(m, 5H), 7.68(s, 1H); MS(ESI) Calc. for (M+1)$^+$: 604. Found: 604.

Part D. t-Butyl 2(S)-benzyloxycarbonylamino-3-[[2-(4-aminobutyl)-1,3,4-thiadiazol-5-yl]carbonyl]aminopropionate A solution of t-Butyl 2(S)-benzyloxycarbonylamino-3-[[2-(4-triazobutyl)-1,3,4-thiadiazol-5-yl]carbonyl] aminopropionate (240 mg, 0.48 mmol), triphenylphosphine (125 mg, 0.48 mmol) in THF(10 ml) was heated to reflux for 3 hrs and then stirred at rt overnight. Water(10 mg, 0.55 mmol) was injected and the reaction mixture was stirred at rt for additional 24 hrs. Concentration followed by chromatography with a mixture of $CH_2Cl_2$, methanol and ammonium hydroxide gave the product as an oil(150 mg, 66% yield). $^1$H NMR(300 MHz, DMSO-$d_6$)δ1.28(s, 9H), 1.40(m, 2H), 1.70(m, 2H), 2.54(t, 2H), 3.10(t, 2H), 3.72(m, 1H), 3.84(m, 1H), 4.20(m, 1H), 5.00(s, 2H), 7.30(m, 5H), 7.76(d, 1H); MS(ESI) Calc. for (M+1)$^+$: 478. Found: 478.

Part E. t-Butyl 2(S)-Benzyloxycarbonylamino-3-[[2-[4-[(N-imidazolin-2-yl)amino]butyl]-1,3,4-thiadiazol-5-yl] carbonyl]aminopropionate A mixture of t-Butyl 2(S)benzyloxycarbonylamino-3-[[2-(4-triazobutyl)-1,3,4-thiadiazol-5-yl]carbonyl] aminopropionate (100 mg, 0.21 mmol) and 2-imidazolidinethione hydrogen iodide (61 mg, 0.25 mmol) in pyridine (5 mL) was stirred at 70° C. for 3 hrs. Concentration and chromatography with a mixture of $CH_2Cl_2$ and methanol as the eluent gave the product as an amorphous solid (60 mg, 53% yield). $^1$H NMR(300 MHz, DMSO-$d_6$) δ1.28(s, 9H), 1.54(m, 2H), 1.76(m, 2H), 3.10(t, 2H), 3.42(m, 2H), 3.60(m, 2H), 4.20(m, 1H), 5.00(s, 2H), 7.30(m, 5H), 7.78(d, 1H), 8.20(t, 1H), 9.20(t, 1H); MS(ESI) Calc. for (M+1)$^+$: 546. Found: 546.

Part E, 2(S)-Benzyloxycarbonylamino-3-[[2-[4-[(N-imidazolin-2-yl)amino]butyl]-1,3,4-thiadiazol-5-yl] carbonyl]aminopropionic acid TFA salt t-Butyl 2(S)-benzyloxycarbonylamino-3-[[2-[4-[(N-imidazolin-2-yl)amino]butyl]-1,3,4-thiadiazol-5-yl] carbonyl]aminopropionate (100 mg, 0.18 mmol) was dissolved in $CH_2Cl_2$ containg 0.25 mL of TFA. The solution was stirred at rt for 24 hrs. Concentration gave the product (80 mg, 89% yield). $^1$H NMR(300 MHz, DMSO-$d_6$)δ1.56 (m, 2H), 1.86(m, 2H), 3.18(m, 4H), 3.54(m, 1H), 3.58(s, 4H), 3.66(m, 1H), 4.10(m, 1H), 5.00(s, 2H), 7.30(m, 5H), 7.76(d, 1H), 8.16(t, 1H), 9.10(t, 1H); MS(ESI) Calc. for (M+1)$^+$: 491. Found: 491.

EXAMPLE 327

2(S)-(2,4,6-Trimethylphenylsulfonyl)amino-3-[[2-[4-[(N-imidazolin-2-yl)amino]butyl]-1,3,4-thiadiazol-5-yl]carbonyl]aminopropionic acid TFA salt This compound was analogously synthesized to Example 321.

$^1$H NMR(300 MHz, DMSO-$d_6$)1.54(m, 2H), 1.76(m, 2H), 2.20(s, 3H), 2.60(s, 6H), 3.10(m, 4H), 3.42(m, 1H), 3.60(m, 1H) , 3.82(s, 4H), 4.20(m, 1H), 6.98(s, 2H), 7.40(d, 2H) 7.78(d, 1H), 8.20(t, 1H), 9.20(t, 1H); MS(ESI) Calc. for (M+1)$^+$: 538. Found: 538.

EXAMPLE 330

2(S)-(1-Naphthalenesulfonyl)amino-3-[[2-[4-[(N-imidazolin-2-yl)amino]butyl]-1,3,4-thiadiazol-5-yl] carbonyl]aminopropionic acid TFA salt This compound was analogously synthesized to Example 321.

$^1$H NMR(300 MHz, DMSO-$d_6$)δ1.56(m, 2H), 1.74(m, 2H), 3.14(m, 4H), 3.38(m, 1H), 3.48(m, 1H), 3.58(s, 4H), 4.08(m, 1H), 7.60(m, 4H), 7.98(d, 1H), 8.06(d, 1H), 8.16(m, 2H), 8.58(d, 1H), 8.70(d, 1H), 9.12(t, 1H); MS(ESI) Calc. for (M+1)$^+$: 546. Found: 546.

TABLE 1

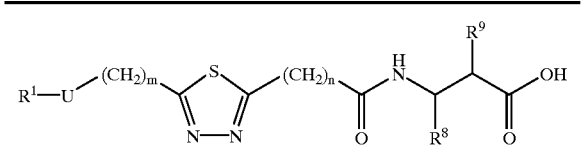

| Ex. No. | R¹-U | m | n | R⁸ | R⁹ | MS |
|---|---|---|---|---|---|---|
| 1 | tetrahydropyrimidin-2-ylamino | 3 | 1 | H | H | |
| 2 | tetrahydropyrimidin-2-ylamino | 3 | 1 | H | NHCbz | |
| 3 | tetrahydropyrimidin-2-ylamino | 3 | 1 | H | NHtBOC | |
| 4 | tetrahydropyrimidin-2-ylamino | 3 | 1 | H | NHCO$_2$-nBu | |
| 5 | tetrahydropyrimidin-2-ylamino | 3 | 1 | H | NHCO$_2$Et | |
| 6 | tetrahydropyrimidin-2-ylamino | 3 | 1 | H | NHCO$_2$Me | |
| 7 | tetrahydropyrimidin-2-ylamino | 3 | 1 | H | NHCO(CH$_2$)$_n$Ph | |
| 8 | tetrahydropyrimidin-2-ylamino | 3 | 1 | H | NHCOtBu | |
| 9 | tetrahydropyrimidin-2-ylamino | 3 | 1 | H | NHCO-n-C$_5$H$_{11}$ | |
| 10 | tetrahydropyrimidin-2-ylamino | 3 | 1 | H | NHCO-n-C$_4$H$_9$ | |
| 11 | tetrahydropyrimidin-2-ylamino | 3 | 1 | H | NHCOCH$_2$CH$_3$ | |
| 12 | tetrahydropyrimidin-2-ylamino | 3 | 1 | H | NHCOCH$_3$ | |
| 13 | tetrahydropyrimidin-2-ylamino | 3 | 1 | H | NHSO$_2$CH$_3$ | |
| 14 | tetrahydropyrimidin-2-ylamino | 3 | 1 | H | NHSO$_2$CH$_2$CH$_3$ | |
| 15 | tetrahydropyrimidin-2-ylamino | 3 | 1 | H | NHSO$_2$n-Bu | |
| 16 | tetrahydropyrimidin-2-ylamino | 3 | 1 | H | NHSO$_2$Ph | |
| 17 | tetrahydropyrimidin-2-ylamino | 3 | 1 | H | NHSO$_2$C$_6$H$_4$ (4-CH$_3$) | |
| 18 | tetrahydropyrimidin-2-ylamino | 3 | 1 | H | NHSO$_2$Bn | |
| 19 | tetrahydropyrimidin-2-ylamino | 3 | 1 | H | NHCO (2-pyridyl) | |
| 20 | tetrahydropyrimidin-2-ylamino | 3 | 1 | H | NHCO (3-pyridyl) | |
| 21 | tetrahydropyrimidin-2-ylamino | 3 | 1 | H | NHCO (4-pyridyl) | |
| 22 | tetrahydropyrimidin-2-ylamino | 3 | 1 | H | NHCOCH$_2$ (2-pyridyl) | |
| 23 | tetrahydropyrimidin-2-ylamino | 3 | 1 | H | NHCOCH$_2$ (3-pyridyl) | |
| 24 | tetrahydropyrimidin-2-ylamino | 3 | 1 | H | NHCOCH$_2$ (4-pyridyl) | |
| 25 | tetrahydropyrimidin-2-ylamino | 3 | 1 | H | NHCO$_2$CH$_2$ (2-pyridyl) | |
| 26 | tetrahydropyrimidin-2-ylamino | 3 | 1 | H | NHCO$_2$CH$_2$ (3-pyridyl) | |
| 27 | tetrahydropyrimidin-2-ylamino | 3 | 1 | H | NHCO$_2$CH$_2$ (4-pyridyl) | |
| 28 | imidazolin-2-ylamino | 3 | 1 | H | H | |
| 29 | imidazolin-2-ylamino | 3 | 1 | H | NHCbz | |
| 30 | imidazolin-2-ylamino | 3 | 1 | H | NHtBOC | |
| 31 | imidazolin-2-ylamino | 3 | 1 | H | NHCO$_2$-nBu | |
| 32 | imidazolin-2-ylamino | 3 | 1 | H | NHCO$_2$Et | |
| 33 | imidazolin-2-ylamino | 3 | 1 | H | NHCO$_2$Me | |
| 34 | imidazolin-2-ylamino | 3 | 1 | H | NHCO(CH$_2$)$_n$Ph | |
| 35 | imidazolin-2-ylamino | 3 | 1 | H | NHCOtBu | |
| 36 | imidazolin-2-ylamino | 3 | 1 | H | NHCO-n-C$_5$H$_{11}$ | |
| 37 | imidazolin-2-ylamino | 3 | 1 | H | NHCO-n-C$_4$H$_9$ | |
| 38 | imidazolin-2-ylamino | 3 | 1 | H | NHCOCH$_2$CH$_3$ | |
| 39 | imidazolin-2-ylamino | 3 | 1 | H | NHCOCH$_3$ | |
| 40 | imidazolin-2-ylamino | 3 | 1 | H | NHSO$_2$CH$_3$ | |
| 41 | imidazolin-2-ylamino | 3 | 1 | H | NHSO$_2$CH$_2$CH$_3$ | |
| 42 | imidazolin-2-ylamino | 3 | 1 | H | NHSO$_2$n-Bu | |
| 43 | imidazolin-2-ylamino | 3 | 1 | H | NHSO$_2$Ph | 496 |
| 44 | imidazolin-2-ylamino | 3 | 1 | H | NHSO$_2$C$_6$H$_4$ (3-CH$_3$) | 510 |
| 45 | imidazolin-2-ylamino | 3 | 1 | H | NHSO$_2$Bn | |
| 46 | imidazolin-2-ylamino | 3 | 1 | H | NHCO (2-pyridyl) | |
| 47 | imidazolin-2-ylamino | 3 | 1 | H | NHCO (3-pyridyl) | |
| 48 | imidazolin-2-ylamino | 3 | 1 | H | NHCO (4-pyridyl) | |
| 49 | imidazolin-2-ylamino | 3 | 1 | H | NHCOCH$_2$ (2-pyridyl) | |
| 50 | imidazolin-2-ylamino | 3 | 1 | H | NHCOCH$_2$ (3-pyridyl) | |
| 51 | imidazolin-2-ylamino | 3 | 1 | H | NHCOCH$_2$ (4-pyridyl) | |
| 52 | imidazolin-2-ylamino | 3 | 1 | H | NHCO$_2$CH$_2$ (2-pyridyl) | |
| 53 | imidazolin-2-ylamino | 3 | 1 | H | NHCO$_2$CH$_2$ (3-pyridyl) | |
| 54 | imidazolin-2-ylamino | 3 | 1 | H | NHCO$_2$CH$_2$ (4-pyridyl) | |
| 55 | tetrahydropyrimidin-2-ylamino | 4 | 0 | H | H | |
| 56 | tetrahydropyrimidin-2-ylamino | 4 | 0 | H | NHCbz | |
| 57 | tetrahydropyrimidin-2-ylamino | 4 | 0 | H | NHtBOC | |
| 58 | tetrahydropyrimidin-2-ylamino | 4 | 0 | H | NHCO$_2$-nBu | |
| 59 | tetrahydropyrimidin-2-ylamino | 4 | 0 | H | NHCO$_2$Et | |
| 60 | tetrahydropyrimidin-2-ylamino | 4 | 0 | H | NHCO$_2$Me | |
| 61 | tetrahydropyrimidin-2-ylamino | 4 | 0 | H | NHCO(CH$_2$)$_n$Ph | |
| 62 | tetrahydropyrimidin-2-ylamino | 4 | 0 | H | NHCOtBu | |
| 63 | tetrahydropyrimidin-2-ylamino | 4 | 0 | H | NHCO-n-C$_5$H$_{11}$ | |
| 64 | tetrahydropyrimidin-2-ylamino | 4 | 0 | H | NHCO-n-C$_4$H$_9$ | |
| 65 | tetrahydropyrimidin-2-ylamino | 4 | 0 | H | NHCOCH$_2$CH$_3$ | |
| 66 | tetrahydropyrimidin-2-ylamino | 4 | 0 | H | NHCOCH$_3$ | |
| 67 | tetrahydropyrimidin-2-ylamino | 4 | 0 | H | NHSO$_2$CH$_3$ | |
| 68 | tetrahydropyrimidin-2-ylamino | 4 | 0 | H | NHSO$_2$CH$_2$CH$_3$ | |

TABLE 1-continued

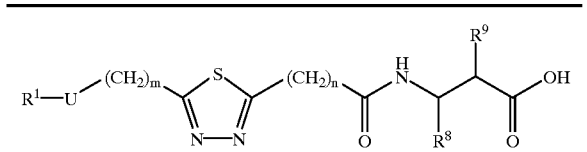

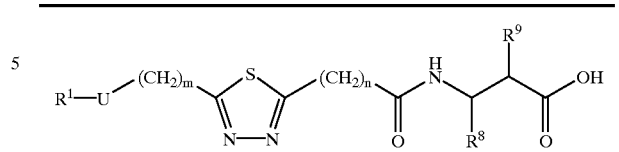

| Ex. No. | R¹-U | m | n | R⁸ | R⁹ | MS |
|---|---|---|---|---|---|---|
| 69 | tetrahydropyrimidin-2-ylamino | 4 | 0 | H | $NHSO_2$n-Bu | |
| 70 | tetrahydropyrimidin-2-ylamino | 4 | 0 | H | $NHSO_2$Ph | |
| 71 | tetrahydropyrimidin-2-ylamino | 4 | 0 | H | $NHSO_2C_6H_4$(4-$CH_3$) | |
| 72 | tetrahydropyrimidin-2-ylamino | 4 | 0 | H | $NHSO_2$Bn | |
| 73 | tetrahydropyrimidin-2-ylamino | 4 | 0 | H | NHCO (2-pyridyl) | |
| 74 | tetrahydropyrimidin-2-ylamino | 4 | 0 | H | NHCO (3-pyridyl) | |
| 75 | tetrahydropyrimidin-2-ylamino | 4 | 0 | H | NHCO (4-pyridyl) | |
| 76 | tetrahydropyrimidin-2-ylamino | 4 | 0 | H | $NHCOCH_2$(2-pyridyl) | |
| 77 | tetrahydropyrimidin-2-ylamino | 4 | 0 | H | $NHCOCH_2$(3-pyridyl) | |
| 78 | tetrahydropyrimidin-2-ylamino | 4 | 0 | H | $NHCOCH_2$(4-pyridyl) | |
| 79 | tetrahydropyrimidin-2-ylamino | 4 | 0 | H | $NHCO_2CH_2$(2-pyridyl) | |
| 80 | tetrahydropyrimidin-2-ylamino | 4 | 0 | H | $NHCO_2CH_2$(3-pyridyl) | |
| 81 | tetrahydropyrimidin-2-ylamino | 4 | 0 | H | $NHCO_2CH_2$(4-pyridyl) | |
| 82 | imidazolin-2-ylamino | 4 | 0 | H | H | |
| 83 | imidazolin-2-ylamino | 4 | 0 | H | NHCbz | |
| 84 | imidazolin-2-ylamino | 4 | 0 | H | NHtBOC | |
| 85 | imidazolin-2-ylamino | 4 | 0 | H | $NHCO_2$-nBu | |
| 86 | imidazolin-2-ylamino | 4 | 0 | H | $NHCO_2$Et | |
| 87 | imidazolin-2-ylamino | 4 | 0 | H | $NHCO_2$Me | |
| 88 | imidazolin-2-ylamino | 4 | 0 | H | $NHCO(CH_2)_n$Ph | |
| 89 | imidazolin-2-ylamino | 4 | 0 | H | NHCOtBu | |
| 90 | imidazolin-2-ylamino | 4 | 0 | H | NHCO-n-$C_5H_{11}$ | |
| 91 | imidazolin-2-ylamino | 4 | 0 | H | NHCO-n-$C_4H_9$ | |
| 92 | imidazolin-2-ylamino | 4 | 0 | H | $NHCOCH_2CH_3$ | |
| 93 | imidazolin-2-ylamino | 4 | 0 | H | $NHCOCH_3$ | |
| 94 | imidazolin-2-ylamino | 4 | 0 | H | $NHSO_2CH_3$ | |
| 95 | imidazolin-2-ylamino | 4 | 0 | H | $NHSO_2CH_2CH_3$ | |
| 96 | imidazolin-2-ylamino | 4 | 0 | H | $NHSO_2$n-Bu | |
| 97 | imidazolin-2-ylamino | 4 | 0 | H | $NHSO_2$Ph | |
| 98 | imidazolin-2-ylamino | 4 | 0 | H | $NHSO_2C_6H_4$(4-$CH_3$) | |
| 99 | imidazolin-2-ylamino | 4 | 0 | H | $NHSO_2$Bn | |
| 100 | imidazolin-2-ylamino | 4 | 0 | H | NHCO (2-pyridyl) | |
| 101 | imidazolin-2-ylamino | 4 | 0 | H | NHCO (3-pyridyl) | |
| 102 | imidazolin-2-ylamino | 4 | 0 | H | NHCO (4-pyridyl) | |
| 103 | imidazolin-2-ylamino | 4 | 0 | H | $NHCOCH_2$(2-pyridyl) | |
| 104 | imidazolin-2-ylamino | 4 | 0 | H | $NHCOCH_2$(3-pyridyl) | |
| 105 | imidazolin-2-ylamino | 4 | 0 | H | $NHCOCH_2$(4-pyridyl) | |
| 106 | imidazolin-2-ylamino | 4 | 0 | H | $NHCO_2CH_2$(2-pyridyl) | |
| 107 | imidazolin-2-ylamino | 4 | 0 | H | $NHCO_2CH_2$(3-pyridyl) | |
| 108 | imidazolin-2-ylamino | 4 | 0 | H | $NHCO_2CH_2$(4-pyridyl) | |
| 109 | tetrahydropyrimidin-2-ylamino | 3 | 0 | H | H | |
| 110 | tetrahydropyrimidin-2-ylamino | 3 | 0 | H | NHCbz | |
| 111 | tetrahydropyrimidin-2-ylamino | 3 | 0 | H | NHtBOC | |
| 112 | tetrahydropyrimidin-2-ylamino | 3 | 0 | H | $NHCO_2$-nBu | |
| 113 | tetrahydropyrimidin-2-ylamino | 3 | 0 | H | $NHCO_2$Et | |
| 114 | tetrahydropyrimidin-2-ylamino | 3 | 0 | H | $NHCO_2$Me | |
| 115 | tetrahydropyrimidin-2-ylamino | 3 | 0 | H | $NHCO(CH_2)_n$Ph | |
| 116 | tetrahydropyrimidin-2-ylamino | 3 | 0 | H | NHCOtBu | |
| 117 | tetrahydropyrimidin-2-ylamino | 3 | 0 | H | NHCO-n-$C_5H_{11}$ | |
| 118 | tetrahydropyrimidin-2-ylamino | 3 | 0 | H | NHCO-n-$C_4H_9$ | |
| 119 | tetrahydropyrimidin-2-ylamino | 3 | 0 | H | $NHCOCH_2CH_3$ | |
| 120 | tetrahydropyrimidin-2-ylamino | 3 | 0 | H | $NHCOCH_3$ | |
| 121 | tetrahydropyrimidin-2-ylamino | 3 | 0 | H | $NHSO_2CH_3$ | |
| 122 | tetrahydropyrimidin-2-ylamino | 3 | 0 | H | $NHSO_2CH_2CH_3$ | |
| 123 | tetrahydropyrimidin-2-ylamino | 3 | 0 | H | $NHSO_2$n-Bu | |
| 124 | tetrahydropyrimidin-2-ylamino | 3 | 0 | H | $NHSO_2$Ph | |
| 125 | tetrahydropyrimidin-2-ylamino | 3 | 0 | H | $NHSO_2C_6H_4$(4-$CH_3$) | |
| 126 | tetrahydropyrimidin-2-ylamino | 3 | 0 | H | $NHSO_2$Bn | |
| 127 | tetrahydropyrimidin-2-ylamino | 3 | 0 | H | NHCO (2-pyridyl) | |
| 128 | tetrahydropyrimidin-2-ylamino | 3 | 0 | H | NHCO (3-pyridyl) | |
| 129 | tetrahydropyrimidin-2-ylamino | 3 | 0 | H | NHCO (4-pyridyl) | |
| 130 | tetrahydropyrimidin-2-ylamino | 3 | 0 | H | $NHCOCH_2$(2-pyridyl) | |
| 131 | tetrahydropyrimidin-2-ylamino | 3 | 0 | H | $NHCOCH_2$(3-pyridyl) | |
| 132 | tetrahydropyrimidin-2-ylamino | 3 | 0 | H | $NHCOCH_2$(4-pyridyl) | |
| 133 | tetrahydropyrimidin-2-ylamino | 3 | 0 | H | $NHCO_2CH_2$(2-pyridyl) | |
| 134 | tetrahydropyrimidin-2-ylamino | 3 | 0 | H | $NHCO_2CH_2$(3-pyridyl) | |
| 135 | tetranydropyrimidin-2-ylamino | 3 | 0 | H | $NHCO_2CH_2$(4-pyridyl) | |
| 136 | imidazolin-2-ylamino | 3 | 0 | H | H | |

TABLE 1-continued

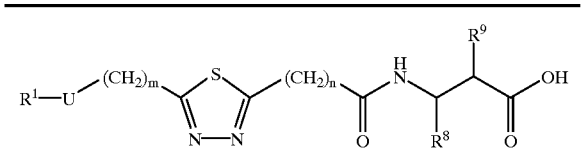 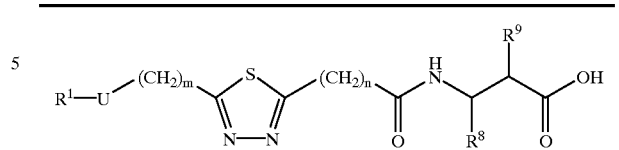

| Ex. No. | R¹-U | m | n | R⁸ | R⁹ | MS |
|---|---|---|---|---|---|---|
| 137 | imidazolin-2-ylamino | 3 | 0 | H | NHCbz | |
| 138 | imidazolin-2-ylamino | 3 | 0 | H | NHtBOC | |
| 139 | imidazolin-2-ylamino | 3 | 0 | H | NHCO$_2$-nBu | |
| 140 | imidazolin-2-ylamino | 3 | 0 | H | NHCO$_2$Et | |
| 141 | imidazolin-2-ylamino | 3 | 0 | H | NHCO$_2$Me | |
| 142 | imidazolin-2-ylamino | 3 | 0 | H | NHCO(CH$_2$)$_n$Ph | |
| 143 | imidazolin-2-ylamino | 3 | 0 | H | NHCOtBu | |
| 144 | imidazolin-2-ylamino | 3 | 0 | H | NHCO-n-C$_5$H$_{11}$ | |
| 145 | imidazolin-2-ylamino | 3 | 0 | H | NHCO-n-C$_4$H$_9$ | |
| 146 | imidazolin-2-ylamino | 3 | 0 | H | NHCOCH$_2$CH$_3$ | |
| 147 | imidazolin-2-ylamino | 3 | 0 | H | NHCOCH$_3$ | |
| 148 | imidazolin-2-ylamino | 3 | 0 | H | NHSO$_2$CH$_3$ | |
| 149 | imidazolin-2-ylamino | 3 | 0 | H | NHSO$_2$CH$_2$CH$_3$ | |
| 150 | imidazolin-2-ylamino | 3 | 0 | H | NHSO$_2$n-Bu | |
| 151 | imidazolin-2-ylamino | 3 | 0 | H | NHSO$_2$Ph | |
| 152 | imidazolin-2-ylamino | 3 | 0 | H | NHSO$_2$C$_6$H$_4$(4-CH$_3$) | |
| 153 | imidazolin-2-ylamino | 3 | 0 | H | NHSO$_2$Bn | |
| 154 | imidazolin-2-ylamino | 3 | 0 | H | NHCO (2-pyridyl) | |
| 155 | imidazolin-2-ylamino | 3 | 0 | H | NHCO (3-pyridyl) | |
| 156 | imidazolin-2-ylamino | 3 | 0 | H | NHCO (4-pyridyl) | |
| 157 | imidazolin-2-ylamino | 3 | 0 | H | NHCOCH$_2$ (2-pyridyl) | |
| 158 | imidazolin-2-ylamino | 3 | 0 | H | NHCOCH$_2$ (3-pyridyl) | |
| 159 | imidazolin-2-ylamino | 3 | 0 | H | NHCOCH$_2$ (4-pyridyl) | |
| 160 | imidazolin-2-ylamino | 3 | 0 | H | NHCO$_2$CH$_2$ (2-pyridyl) | |
| 161 | imidazolin-2-ylamino | 3 | 0 | H | NHCO$_2$CH$_2$ (3-pyridyl) | |
| 162 | imidazolin-2-ylamino | 3 | 0 | H | NHCO$_2$CH$_2$ (4-pyridyl) | |
| 163 | 4,1,3-oxadiazin-2-ylamino | 4 | 0 | H | NHCbz | |
| 164 | 4,1,3-oxadiazin-2-ylamino | 4 | 0 | H | NHCO$_2$-n-Bu | |
| 165 | 4,1,3-oxadiazin-2-ylamino | 4 | 0 | H | NHSO$_2$Ph | |
| 166 | 4,1,3-oxadiazin-2-ylamino | 4 | 0 | H | NHSO$_2$-n-Bu | |
| 167 | 4,1,3-oxadiazin-2-ylamino | 3 | 1 | H | NHCbz | |
| 168 | 4,1,3-oxadiazin-2-ylamino | 3 | 1 | H | NHCO$_2$-n-Bu | |
| 169 | 4,1,3-oxadiazin-2-ylamino | 3 | 1 | H | NHSO$_2$Ph | |
| 170 | 4,1,3-oxadiazin-2-ylamino | 3 | 1 | H | NHSO$_2$-n-Bu | |
| 172 | pyridin-2-ylamino | 3 | 1 | H | NHCbz | |
| 173 | pyridin-2-ylamino | 3 | 1 | H | NHCO$_2$-n-Bu | |
| 174 | pyridin-2-ylamino | 3 | 1 | H | NHSO$_2$Ph | |
| 175 | pyridin-2-ylamino | 3 | 1 | H | NHSO$_2$-nBu | |
| 176 | pyridin-2-ylamino | 4 | 0 | H | NHCbz | 499 |
| 177 | pyridin-2-ylamino | 4 | 0 | H | NHCO$_2$-n-Bu | |
| 178 | pyridin-2-ylamino | 4 | 0 | H | (2,4,6-trimethyl-phenylsulfonyl)-amino | 547 |
| 179 | pyridin-2-ylamino | 4 | 0 | H | (1-naphthalene-sulfonyl)amino | 555 |
| 180 | pyridin-2-ylamino | 3 | 0 | H | NHCbz | |
| 181 | pyridin-2-ylamino | 3 | 0 | H | NHCO$_2$-n-Bu | |
| 182 | pyridin-2-ylamino | 3 | 0 | H | NHSO$_2$Ph | |
| 183 | pyridin-2-ylamino | 3 | 0 | H | NHSO$_2$-nBu | |
| 184 | imidazol-2-ylamino | 3 | 1 | H | NHCbz | |
| 185 | imidazol-2-ylamino | 3 | 1 | H | NHCO$_2$-n-Bu | |
| 186 | imidazol-2-ylamino | 3 | 1 | H | NHSO$_2$Ph | |
| 187 | imidazol-2-ylamino | 3 | 1 | H | NHSO$_2$-nBu | |
| 188 | imidazol-2-ylamino | 4 | 0 | H | NHCbz | |
| 189 | imidazol-2-ylamino | 4 | 0 | H | NHCO$_2$-n-Bu | |
| 190 | imidazol-2-ylamino | 4 | 0 | H | NHSO$_2$Ph | |
| 191 | imidazol-2-ylamino | 4 | 0 | H | NHSO$_2$-nBu | |
| 192 | imidazol-2-ylamino | 3 | 0 | H | NHCbz | |
| 193 | imidazol-2-ylamino | 3 | 0 | H | NHCO$_2$-n-Bu | |
| 194 | imidazol-2-ylamino | 3 | 0 | H | NHSO$_2$Ph | |
| 195 | imidazol-2-ylamino | 3 | 0 | H | NHSO$_2$-nBu | |
| 196 | thiazol-2-ylamino | 3 | 1 | H | NHCbz | |
| 197 | 2-aminopyridin-6-yl | 3 | 1 | H | NHCO$_2$-n-Bu | |
| 198 | 2-aminopyridin-6-yl | 3 | 1 | H | NHSO$_2$Ph | |
| 199 | 2-aminopyridin-6-yl | 3 | 1 | H | NHSO$_2$-nBu | |
| 200 | 2-aminopyridin-6-yl | 4 | 0 | H | NHCbz | |
| 201 | 2-aminopyridin-6-yl | 4 | 0 | H | NHCO$_2$-n-Bu | |
| 202 | 2-aminopyridin-6-yl | 4 | 0 | H | NHSO$_2$Ph | |
| 203 | 2-aminopyridin-6-yl | 4 | 0 | H | NHSO$_2$-nBu | |
| 204 | 2-aminopyridin-6-yl | 3 | 0 | H | NHCbz | |
| 205 | 2-aminopyridin-6-yl | 3 | 0 | H | NHCO$_2$-n-Bu | |
| 206 | 2-aminopyridin-6-yl | 3 | 0 | H | NHSO$_2$Ph | |
| 207 | 2-aminopyridin-6-yl | 3 | 0 | H | NHSO$_2$-nBu | |
| 208 | 2-aminopyridin-3-yl | 2 | 0 | H | NHCbz | |
| 209 | 2-aminopyridin-3-yl | 2 | 0 | H | NHCO$_2$-n-Bu | |
| 210 | 2-aminopyridin-3-yl | 2 | 0 | H | NHSO$_2$Ph | |
| 211 | 2-aminopyridin-3-yl | 2 | 0 | H | NHSO$_2$-nBu | |
| 212 | 2-aminothiazol-4-yl | 3 | 1 | H | NHCbz | |
| 213 | 2-aminothiazol-4-yl | 3 | 1 | H | NHCO$_2$-n-Bu | |
| 214 | 2-aminothiazol-4-yl | 3 | 1 | H | NHSO$_2$Ph | |
| 215 | 2-aminothiazol-4-yl | 3 | 1 | H | NHSO$_2$-nBu | |
| 216 | 2-aminothiazol-4-yl | 4 | 0 | H | NHCbz | |
| 217 | 2-aminothiazol-4-yl | 4 | 0 | H | NHCO$_2$-n-Bu | |
| 218 | 2-aminothiazol-4-yl | 4 | 0 | H | NHSO$_2$Ph | |
| 219 | 2-aminopyridin-6-yl | 4 | 0 | H | NHSO$_2$-nBu | |
| 220 | 2-aminothiazol-4-yl | 3 | 0 | H | NHCbz | |
| 221 | 2-aminothiazol-4-yl | 3 | 0 | H | NHCO$_2$-n-Bu | |
| 222 | 2-aminothiazol-4-yl | 3 | 0 | H | NHSO$_2$Ph | |
| 223 | 2-aminothiazol-4-yl | 3 | 0 | H | NHSO$_2$-nBu | |
| 224 | 2-aminothiazol-4-yl | 3 | 1 | H | NHCbz | |
| 225 | 2-aminothiazol-4-yl | 3 | 1 | H | NHCO$_2$-n-Bu | |
| 226 | 1,3,4-thiadiazol-2-ylamino | 3 | 1 | H | NHSO$_2$Ph | |
| 227 | 1,3,4-thiadiazol-2-ylamino | 3 | 1 | H | NHSO$_2$-nBu | |
| 228 | 1,3,4-thiadiazol-2-ylamino | 4 | 0 | H | NHCbz | |
| 229 | 1,3,4-thiadiazol-2-ylamino | 4 | 0 | H | NHCO$_2$-n-Bu | |
| 230 | 1,3,4-thiadiazol-2-ylamino | 4 | 0 | H | NHSO$_2$Ph | |
| 231 | 1,3,4-thiadiazol-2-ylamino | 4 | 0 | H | NHSO$_2$-nBu | |

TABLE 1-continued

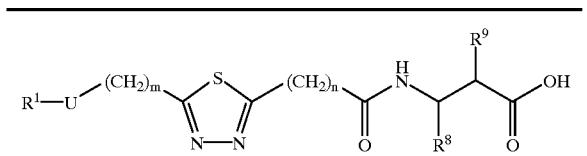

| Ex. No. | R¹-U | m | n | R⁸ | R⁹ | MS |
|---|---|---|---|---|---|---|
| 232 | 1,3,4-thiadiazol-2-ylamino | 3 | 0 | H | NHCbz | |
| 233 | 1,3,4-thiadiazol-2-ylamino | 3 | 0 | H | NHCO$_2$-n-Bu | |
| 234 | 1,3,4-thiadiazol-2-ylamino | 3 | 0 | H | NHSO$_2$Ph | |
| 235 | 1,2,4-thiadiazol-5-ylamino | 3 | 0 | H | NHSO$_2$-nBu | |
| 236 | 1,2,4-thiadiazol-5-ylamino | 3 | 1 | H | NHCbz | |
| 237 | 1,2,4-thiadiazol-5-ylamino | 3 | 1 | H | NHCO$_2$-n-Bu | |
| 238 | 1,2,4-thiadiazol-5-ylamino | 3 | 1 | H | NHSO$_2$Ph | |
| 239 | 1,2,4-thiadiazol-5-ylamino | 3 | 1 | H | NHSO$_2$-nBu | |
| 240 | 1,2,4-thiadiazol-5-ylamino | 4 | 0 | H | NHCbz | |
| 241 | 1,2,4-thiadiazol-5-ylamino | 4 | 0 | H | NHCO$_2$-n-Bu | |
| 242 | 1,2,4-thiadiazol-5-ylamino | 4 | 0 | H | NHSO$_2$Ph | |
| 243 | 1,2,4-thiadiazol-5-ylamino | 4 | 0 | H | NHSO$_2$-nBu | |
| 244 | 1,2,4-thiadiazol-5-ylamino | 3 | 0 | H | NHCbz | |
| 245 | 1,2,4-thiadiazol-5-ylamino | 3 | 0 | H | NHCO$_2$-n-Bu | |
| 246 | 1,2,4-thiadiazol-5-ylamino | 3 | 0 | H | NHSO$_2$Ph | |
| 247 | isoxazol-3-ylamino | 3 | 0 | H | NHSO$_2$-nBu | |
| 248 | isoxazol-3-ylamino | 3 | 1 | H | NHCbz | |
| 249 | isoxazol-3-ylamino | 3 | 1 | H | NHCO$_2$-n-Bu | |
| 250 | isoxazol-3-ylamino | 3 | 1 | H | NHSO$_2$Ph | |
| 251 | isoxazol-3-ylamino | 3 | 1 | H | NHSO$_2$-nBu | |
| 252 | isoxazol-3-ylamino | 4 | 0 | H | NHCbz | |
| 253 | isoxazol-3-ylamino | 4 | 0 | H | NHCO$_2$-n-Bu | |
| 254 | isoxazol-3-ylamino | 4 | 0 | H | NHSO$_2$Ph | |
| 255 | isoxazol-3-ylamino | 4 | 0 | H | NHSO$_2$-nBu | |
| 256 | isoxazol-3-ylamino | 3 | 0 | H | NHCbz | |
| 257 | isoxazol-3-ylamino | 3 | 0 | H | NHCO$_2$-n-Bu | |
| 258 | isoxazol-3-ylamino | 3 | 0 | H | NHSO$_2$Ph | |
| 259 | oxazol-2-ylamino | 3 | 0 | H | NHSO$_2$-nBu | |
| 260 | oxazol-2-ylamino | 3 | 1 | H | NHCbz | |
| 261 | oxazol-2-ylamino | 3 | 1 | H | NHCO$_2$-n-Bu | |
| 262 | oxazol-2-ylamino | 3 | 1 | H | NHSO$_2$Ph | |
| 263 | oxazol-2-ylamino | 3 | 1 | H | NHSO$_2$-nBu | |
| 264 | oxazol-2-ylamino | 4 | 0 | H | NHCbz | |
| 265 | oxazol-2-ylamino | 4 | 0 | H | NHCO$_2$-n-Bu | |
| 266 | oxazol-2-ylamino | 4 | 0 | H | NHSO$_2$Ph | |
| 267 | oxazol-2-ylamino | 4 | 0 | H | NHSO$_2$-nBu | |
| 268 | oxazol-2-ylamino | 3 | 0 | H | NHCbz | |
| 269 | oxazol-2-ylamino | 3 | 0 | H | NHCO$_2$-n-Bu | |
| 270 | oxazol-2-ylamino | 3 | 0 | H | NHSO$_2$Ph | |
| 271 | oxazol-2-ylamino | 3 | 0 | H | NHSO$_2$-nBu | |
| 272 | 1,2,5-thiadiazol-3-ylamino | 3 | 1 | H | NHCbz | |
| 273 | 1,2,5-thiadiazol-3-ylamino | 3 | 1 | H | NHCO$_2$-n-Bu | |
| 274 | 1,2,5-thiadiazol-3-ylamino | 3 | 1 | H | NHSO$_2$Ph | |
| 275 | 1,2,5-thiadiazol-3-ylamino | 3 | 1 | H | NHSO$_2$-nBu | |
| 276 | 1,2,5-thiadiazol-3-ylamino | 4 | 0 | H | NHCbz | |
| 277 | 1,2,5-thiadiazol-3-ylamino | 4 | 0 | H | NHCO$_2$-n-Bu | |
| 278 | 1,2,5-thiadiazol-3-ylamino | 4 | 0 | H | NHSO$_2$Ph | |
| 279 | 1,2,5-thiadiazol-3-ylamino | 4 | 0 | H | NHSO$_2$-nBu | |
| 280 | 1,2,5-thiadiazol-3-ylamino | 3 | 0 | H | NHCbz | |
| 281 | 1,2,5-thiadiazol-3-ylamino | 3 | 0 | H | NHCO$_2$-n-Bu | |
| 282 | 1,2,5-thiadiazol-3-ylamino | 3 | 0 | H | NHSO$_2$Ph | |
| 283 | 1,2,5-thiadiazol-3-ylamino | 3 | 0 | H | NHSO$_2$-nBu | |
| 284 | imidazolin-2-ylamino | 2 | 2 | H | NHCbz | |
| 285 | imidazolin-2-ylamino | 2 | 2 | H | NHCO$_2$-n-Bu | |
| 286 | imidazolin-2-ylamino | 2 | 2 | H | NHSO$_2$Ph | |
| 287 | imidazolin-2-ylamino | 2 | 2 | H | NHSO$_2$-nBu | |
| 288 | tetrahydropyrimidin-2-ylamino | 2 | 2 | H | NHCbz | |
| 289 | tetrahydropyrimidin-2-ylamino | 2 | 2 | H | NHCO$_2$-n-Bu | |
| 290 | tetrahydropyrimidin-2-ylamino | 2 | 2 | H | NHSO$_2$Ph | |
| 291 | tetrahydropyrimidin-2-ylamino | 2 | 2 | H | NHSO$_2$-nBu | |
| 292 | benzimidazol-2-ylamino | 4 | 0 | H | NHCbz | |
| 293 | benzthiazol-2-ylamino | 4 | 0 | H | NHCbz | |
| 294 | 1,2-pyrazol-3-ylamino | 4 | 0 | H | NHCbz | |
| 295 | 1,2,4-triazol-5-ylamino | 4 | 0 | H | NHCbz | |
| 296 | imidazol-4-ylamino | 4 | 0 | H | NHCbz | |
| 297 | 1,3,4-oxadiazol-2-ylamino | 4 | 0 | H | NHCbz | |
| 298 | 1,2,4-thiadiazol-5-ylamino | 4 | 0 | H | NHCbz | |
| 299 | 1,2,4-thiadiazol-3-ylamino | 4 | 0 | H | NHCbz | |
| 300 | 1,2,5-oxadiazol-3-ylamino | 4 | 0 | H | NHCbz | |
| 301 | 1,2,4-oxadiazol-5-ylamino | 4 | 0 | H | NHCbz | |
| 302 | 1,2,4-oxadiazol-3-ylamino | 4 | 0 | H | NHCbz | |
| 303 | 2-iminopyrrolidin-5-yl | 3 | 1 | H | NHCbz | |
| 304 | 2-iminopyrrolidin-5-yl | 3 | 1 | H | NHSO$_2$Ph | |
| 305 | 2-iminopyrrolidin-5-yl | 3 | 0 | H | NHCbz | |
| 306 | 2-iminopyrrolidin-5-yl | 3 | 0 | H | NHSO$_2$Ph | |
| 307 | 2-iminopyrrolidin-5-yl | 2 | 1 | H | NHCbz | |
| 308 | 2-iminopyrrolidin-5-yl | 2 | 1 | H | NHSO$_2$Ph | |
| 309 | 2-iminopiperidin-6-yl | 3 | 1 | H | NHCbz | |
| 310 | 2-iminopiperidin-6-yl | 3 | 1 | H | NHSO$_2$Ph | |
| 311 | 2-iminopiperidin-6-yl | 3 | 0 | H | NHCbz | |
| 312 | 2-iminopiperidin-6-yl | 3 | 0 | H | NHSO$_2$Ph | |

TABLE 1-continued $R^1-U-(CH_2)_m$-[thiadiazole]-$(CH_2)_n$-C(O)-NH-CHR$^8$-CHR$^9$-COOH (with thiadiazole S at top, two N at bottom)

| Ex. No. | R$^1$-U | m | n | R$^8$ | R$^9$ | MS |
|---|---|---|---|---|---|---|
| 313 | 2-iminopiperidin-6-yl | 2 | 1 | H | NHCbz | |
| 314 | 2-iminopiperidin-6-yl | 2 | 1 | H | NHSO$_2$Ph | |
| 315 | 2-iminoazepin-7-yl | 3 | 1 | H | NHCbz | |
| 316 | 2-iminoazepin-7-yl | 3 | 1 | H | NHSO$_2$Ph | |
| 317 | 2-iminoazepin-7-yl | 3 | 0 | H | NHCbz | |
| 318 | 2-iminoazepin-7-yl | 3 | 0 | H | NHSO$_2$Ph | |
| 319 | 2-iminoazepin-7-yl | 2 | 1 | H | NHCbz | |
| 320 | 2-iminoazepin-7-yl | 2 | 1 | H | NHSO$_2$Ph | |
| 321 | imidazolin-2-ylamino | 4 | 0 | H | NHCbz | 491 |
| 322 | benzthiazol-2-ylamino | 4 | 0 | n-Bu | H | |
| 323 | 1,2-pyrazol-3-ylamino | 4 | 0 | n-Bu | H | |
| 324 | 1,2,4-triazol-5-ylamino | 4 | 0 | n-Bu | H | |
| 325 | imidazol-4-ylamino | 4 | 0 | n-Bu | H | |
| 326 | 1,3,4-oxadiazol-2-ylamino | 4 | 0 | n-Bu | H | |
| 327 | imidazolin-2-ylamino | 4 | 0 | H | (2,4,6-trimethyl-phenylsulfonyl)-amino | 538 |
| 328 | 1,2,4-thiadiazol-3-ylamino | 4 | 0 | n-Bu | H | |
| 329 | 1,2,5-oxadiazol-3-ylamino | 4 | 0 | n-Bu | H | |
| 330 | imidazolin-2-ylamino | 4 | 0 | H | (1-naphthalene-sulphonylamino) | 546 |
| 331 | 1,2,4-oxadiazol-3-ylamino | 4 | 0 | n-Bu | H | |

TABLE 2

$R^1-U-(CH_2)_m$-[oxadiazole]-$(CH_2)_n$-C(O)-NH-CHR$^8$-CHR$^9$-COOH

| Ex. No. | R$^1$-U | m | n | R$^8$ | R$^{16}$ | MS |
|---|---|---|---|---|---|---|
| 501 | tetrahydropyrimidin-2-ylamino | 3 | 1 | H | H | |
| 502 | tetrahydropyrimidin-2-ylamino | 3 | 1 | H | NHCbz | |
| 503 | tetrahydropyrimidin-2-ylamino | 3 | 1 | H | NHtBOC | |
| 504 | tetrahydropyrimidin-2-ylamino | 3 | 1 | H | NHCO$_2$-nBu | |
| 505 | tetrahydropyrimidin-2-ylamino | 3 | 1 | H | NHCO$_2$Et | |
| 506 | tetrahydropyrimidin-2-ylamino | 3 | 1 | H | NHCO$_2$Me | |
| 507 | tetrahydropyrimidin-2-ylamino | 3 | 1 | H | NHCO(CH$_2$)$_n$Ph | |
| 508 | tetrahydropyrimidin-2-ylamino | 3 | 1 | H | NHCOtBu | |
| 509 | tetrahydropyrimidin-2-ylamino | 3 | 1 | H | NHCO-n-C$_5$H$_{11}$ | |
| 510 | tetrahydropyrimidin-2-ylamino | 3 | 1 | H | NHCO-n-C$_4$H$_9$ | |
| 511 | tetrahydropyrimidin-2-ylamino | 3 | 1 | H | NHCOCH$_2$CH$_3$ | |
| 512 | tetrahydropyrimidin-2-ylamino | 3 | 1 | H | NHCOCH$_3$ | |
| 513 | tetrahydropyrimidin-2-ylamino | 3 | 1 | H | NHSO$_2$CH$_3$ | |
| 514 | tetrahydropyrimidin-2-ylamino | 3 | 1 | H | NHSO$_2$CH$_2$CH$_3$ | |
| 515 | tetrahydropyrimidin-2-ylamino | 3 | 1 | H | NHSO$_2$n-Bu | |
| 516 | tetrahydropyrimidin-2-ylamino | 3 | 1 | H | NHSO$_2$Ph | |
| 517 | tetrahydropyrimidin-2-ylamino | 3 | 1 | H | NHSO$_2$C$_6$H$_4$(4-CH$_3$) | |
| 518 | tetrahydropyrimidin-2-ylamino | 3 | 1 | H | NHSO$_2$Bn | |
| 519 | tetrahydropyrimidin-2-ylamino | 3 | 1 | H | NHCO (2-pyridyl) | |
| 520 | tetrahydropyrimidin-2-ylamino | 3 | 1 | H | NHCO (3-pyridyl) | |
| 521 | tetrahydropyrimidin-2-ylamino | 3 | 1 | H | NHCO (4-pyridyl) | |
| 522 | tetrahydropyrimidin-2-ylamino | 3 | 1 | H | NHCOCH$_2$ (2-pyridyl) | |
| 523 | tetrahydropyrimidin-2-ylamino | 3 | 1 | H | NHCOCH$_2$ (3-pyridyl) | |
| 524 | tetrahydropyrimidin-2-ylamino | 3 | 1 | H | NHCOCH$_2$ (4-pyridyl) | |
| 525 | tetrahydropyrimidin-2-ylamino | 3 | 1 | H | NHCO$_2$CH$_2$ (2-pyridyl) | |
| 526 | tetrahydropyrimidin-2-ylamino | 3 | 1 | H | NHCO$_2$CH$_2$ (3-pyridyl) | |
| 527 | tetrahydropyrimidin-2-ylamino | 3 | 1 | H | NHCO$_2$CH$_2$ (4-pyridyl) | |
| 528 | imidazolin-2-ylamino | 3 | 1 | H | H | |
| 529 | imidazolin-2-ylamino | 3 | 1 | H | NHCbz | |
| 530 | imidazolin-2-ylamino | 3 | 1 | H | NHtBOC | |
| 531 | imidazolin-2-ylamino | 3 | 1 | H | NHCO$_2$-nBu | |
| 532 | imidazolin-2-ylamino | 3 | 1 | H | NHCO$_2$Et | |
| 533 | imidazolin-2-ylamino | 3 | 1 | H | NHCO$_2$Me | |
| 534 | imidazolin-2-ylamino | 3 | 1 | H | NHCO(CH$_2$)$_n$Ph | |
| 535 | imidazolin-2-ylamino | 3 | 1 | H | NHCOtBu | |
| 536 | imidazolin-2-ylamino | 3 | 1 | H | NHCO-n-C$_5$H$_{11}$ | |
| 537 | imidazolin-2-ylamino | 3 | 1 | H | NHCO-n-C$_4$H$_9$ | |
| 538 | imidazolin-2-ylamino | 3 | 1 | H | NHCOCH$_2$CH$_3$ | |
| 539 | imidazolin-2-ylamino | 3 | 1 | H | NHCOCH$_3$ | |
| 540 | imidazolin-2-ylamino | 3 | 1 | H | NHSO$_2$CH$_3$ | |
| 541 | imidazolin-2-ylamino | 3 | 1 | H | NHSO$_2$CH$_2$CH$_3$ | |
| 542 | imidazolin-2-ylamino | 3 | 1 | H | NHSO$_2$n-Bu | |
| 543 | imidazolin-2-ylamino | 3 | 1 | H | NHSO$_2$Ph | |

TABLE 2-continued

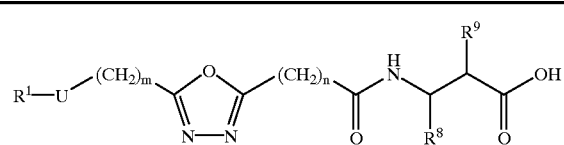

| Ex. No. | R¹-U | m | n | R⁸ | R¹⁶ | MS |
|---|---|---|---|---|---|---|
| 544 | imidazolin-2-ylamino | 3 | 1 | H | NHSO$_2$C$_6$H$_4$(4-CH$_3$) | |
| 545 | imidazolin-2-ylamino | 3 | 1 | H | NHSO$_2$Bn | |
| 546 | imidazolin-2-ylamino | 3 | 1 | H | NHCO (2-pyridyl) | |
| 547 | imidazolin-2-ylamino | 3 | 1 | H | NHCO (3-pyridyl) | |
| 548 | imidazolin-2-ylamino | 3 | 1 | H | NHCO (4-pyridyl) | |
| 549 | imidazolin-2-ylamino | 3 | 1 | H | NHCOCH$_2$(2-pyridyl) | |
| 550 | imidazolin-2-ylamino | 3 | 1 | H | NHCOCH$_2$(3-pyridyl) | |
| 551 | imidazolin-2-ylamino | 3 | 1 | H | NHCOCH$_2$(4-pyridyl) | |
| 552 | imidazolin-2-ylamino | 3 | 1 | H | NHCO$_2$CH$_2$(2-pyridyl) | |
| 553 | imidazolin-2-ylamino | 3 | 1 | H | NHCO$_2$CH$_2$(3-pyridyl) | |
| 554 | imidazolin-2-ylamino | 3 | 1 | H | NHCO$_2$CH$_2$(4-pyridyl) | |
| 555 | tetrahydropyrimidin-2-ylamino | 4 | 0 | H | H | |
| 556 | tetrahydropyrimidin-2-ylamino | 4 | 0 | H | NHCbz | |
| 557 | tetrahydropyrimidin-2-ylamino | 4 | 0 | H | NHtBOC | |
| 558 | tetrahydropyrimidin-2-ylamino | 4 | 0 | H | NHCO$_2$-nBu | |
| 559 | tetrahydropyrimidin-2-ylamino | 4 | 0 | H | NHCO$_2$Et | |
| 560 | tetrahydropyrimidin-2-ylamino | 4 | 0 | H | NHCO$_2$Me | |
| 561 | tetrahydropyrimidin-2-ylamino | 4 | 0 | H | NHCO(CH$_2$)$_n$Ph | |
| 562 | tetrahydropyrimidin-2-ylamino | 4 | 0 | H | NHCOtBu | |
| 563 | tetrahydropyrimidin-2-ylamino | 4 | 0 | H | NHCO-n-C$_5$H$_{11}$ | |
| 564 | tetrahydropyrimidin-2-ylamino | 4 | 0 | H | NHCO-n-C$_4$H$_9$ | |
| 565 | tetrahydropyrimidin-2-ylamino | 4 | 0 | H | NHCOCH$_2$CH$_3$ | |
| 566 | tetrahydropyrimidin-2-ylamino | 4 | 0 | H | NHCOCH$_3$ | |
| 567 | tetrahydropyrimidin-2-ylamino | 4 | 0 | H | NHSO$_2$CH$_3$ | |
| 568 | tetrahydropyrimidin-2-ylamino | 4 | 0 | H | NHSO$_2$CH$_2$CH$_3$ | |
| 569 | tetrahydropyrimidin-2-ylamino | 4 | 0 | H | NHSO$_2$n-Bu | |
| 570 | tetrahydropyrimidin-2-ylamino | 4 | 0 | H | NHSO$_2$Ph | |
| 571 | tetrahydropyrimidin-2-ylamino | 4 | 0 | H | NHSO$_2$C$_6$H$_4$(4-CH$_3$) | |
| 572 | tetrahydropyrimidin-2-ylamino | 4 | 0 | H | NHSO$_2$Bn | |
| 573 | tetrahydropyrimidin-2-ylamino | 4 | 0 | H | NHCO (2-pyridyl) | |
| 574 | tetrahydropyrimidin-2-ylamino | 4 | 0 | H | NHCO (3-pyridyl) | |
| 575 | tetrahydropyrimidin-2-ylamino | 4 | 0 | H | NHCO (4-pyridyl) | |
| 576 | tetrahydropyrimidin-2-ylamino | 4 | 0 | H | NHCOCH$_2$(2-pyridyl) | |
| 577 | tetrahydropyrimidin-2-ylamino | 4 | 0 | H | NHCOCH$_2$(3-pyridyl) | |
| 578 | tetrahydropyrimidin-2-ylamino | 4 | 0 | H | NHCOCH$_2$(4-pyridyl) | |
| 579 | tetrahydropyrimidin-2-ylamino | 4 | 0 | H | NHCO$_2$CH$_2$(2-pyridyl) | |
| 580 | tetrahydropyrimidin-2-ylamino | 4 | 0 | H | NHCO$_2$CH$_2$(3-pyridyl) | |
| 581 | tetrahydropyrimidin-2-ylamino | 4 | 0 | H | NHCO$_2$CH$_2$(4-pyridyl) | |
| 582 | imidazolin-2-ylamino | 4 | 0 | H | H | |
| 583 | imidazolin-2-ylamino | 4 | 0 | H | NHCbz | |
| 584 | imidazolin-2-ylamino | 4 | 0 | H | NHtBOC | |
| 585 | imidazolin-2-ylamino | 4 | 0 | H | NHCO$_2$-nBu | |
| 586 | imidazolin-2-ylamino | 4 | 0 | H | NHCO$_2$Et | |
| 587 | imidazolin-2-ylamino | 4 | 0 | H | NHCO$_2$Me | |
| 588 | imidazolin-2-ylamino | 4 | 0 | H | NHCO(CH$_2$)$_n$Ph | |
| 589 | imidazolin-2-ylamino | 4 | 0 | H | NHCOtBu | |
| 590 | imidazolin-2-ylamino | 4 | 0 | H | NHCO-n-C$_5$H$_{11}$ | |
| 591 | imidazolin-2-ylamino | 4 | 0 | H | NHCO-n-C$_4$H$_9$ | |
| 592 | imidazolin-2-ylamino | 4 | 0 | H | NHCOCH$_2$CH$_3$ | |
| 593 | imidazolin-2-ylamino | 4 | 0 | H | NHCOCH$_3$ | |
| 594 | imidazolin-2-ylamino | 4 | 0 | H | NHSO$_2$CH$_3$ | |
| 595 | imidazolin-2-ylamino | 4 | 0 | H | NHSO$_2$CH$_2$CH$_3$ | |
| 596 | imidazolin-2-ylamino | 4 | 0 | H | NHSO$_2$n-Bu | |
| 597 | imidazolin-2-ylamino | 4 | 0 | H | NHSO$_2$Ph | |
| 598 | imidazolin-2-ylamino | 4 | 0 | H | NHSO$_2$C$_6$H$_4$(4-CH$_3$) | |
| 599 | imidazolin-2-ylamino | 4 | 0 | H | NHSO$_2$Bn | |
| 600 | imidazolin-2-ylamino | 4 | 0 | H | NHCO (2-pyridyl) | |
| 601 | imidazolin-2-ylamino | 4 | 0 | H | NHCO (3-pyridyl) | |
| 602 | imidazolin-2-ylamino | 4 | 0 | H | NHCO (4-pyridyl) | |
| 603 | imidazolin-2-ylamino | 4 | 0 | H | NHCOCH$_2$(2-pyridyl) | |
| 604 | imidazolin-2-ylamino | 4 | 0 | H | NHCOCH$_2$(3-pyridyl) | |
| 605 | imidazolin-2-ylamino | 4 | 0 | H | NHCOCH$_2$(4-pyridyl) | |
| 606 | imidazolin-2-ylamino | 4 | 0 | H | NHCO$_2$CH$_2$(2-pyridyl) | |
| 607 | imidazolin-2-ylamino | 4 | 0 | H | NHCO$_2$CH$_2$(3-pyridyl) | |
| 608 | imidazolin-2-ylamino | 4 | 0 | H | NHCO$_2$CH$_2$(4-pyridyl) | |
| 609 | tetrahydropyrimidin-2-ylamino | 3 | 0 | H | H | |
| 610 | tetrahydropyrimidin-2-ylamino | 3 | 0 | H | NHCbz | |
| 611 | tetrahydropyrimidin-2-ylamino | 3 | 0 | H | NHtBOC | |

TABLE 2-continued

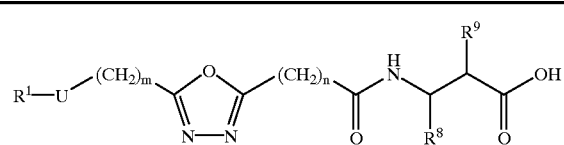

| Ex. No. | R¹-U | m | n | R⁸ | R¹⁶ | MS |
|---|---|---|---|---|---|---|
| 612 | tetrahydropyrimidin-2-ylamino | 3 | 0 | H | NHCO$_2$-nBu | |
| 613 | tetrahydropyrimidin-2-ylamino | 3 | 0 | H | NHCO$_2$Et | |
| 614 | tetrahydropyrimidin-2-ylamino | 3 | 0 | H | NHCO$_2$Me | |
| 615 | tetrahydropyrimidin-2-ylamino | 3 | 0 | H | NHCO(CH$_2$)$_n$Ph | |
| 616 | tetrahydropyrimidin-2-ylamino | 3 | 0 | H | NHCOtBu | |
| 617 | tetrahydropyrimidin-2-ylamino | 3 | 0 | H | NHCO-n-C$_5$H$_{11}$ | |
| 618 | tetrahydropyrimidin-2-ylamino | 3 | 0 | H | NHCO-n-C$_4$H$_9$ | |
| 619 | tetrahydropyrimidin-2-ylamino | 3 | 0 | H | NHCOCH$_2$CH$_3$ | |
| 620 | tetrahydropyrimidin-2-ylamino | 3 | 0 | H | NHCOCH$_3$ | |
| 621 | tetrahydropyrimidin-2-ylamino | 3 | 0 | H | NHSO$_2$CH$_3$ | |
| 622 | tetrahydropyrimidin-2-ylamino | 3 | 0 | H | NHSO$_2$CH$_2$CH$_3$ | |
| 623 | tetrahydropyrimidin-2-ylamino | 3 | 0 | H | NHSO$_2$n-Bu | |
| 624 | tetrahydropyrimidin-2-ylamino | 3 | 0 | H | NHSO$_2$Ph | |
| 625 | tetrahydropyrimidin-2-ylamino | 3 | 0 | H | NHSO$_2$C$_6$H$_4$ (4-CH$_3$) | |
| 626 | tetrahydropyrimidin-2-ylamino | 3 | 0 | H | NHSO$_2$Bn | |
| 627 | tetrahydropyrimidin-2-ylamino | 3 | 0 | H | NHCO (2-pyridyl) | |
| 628 | tetrahydropyrimidin-2-ylamino | 3 | 0 | H | NHCO (3-pyridyl) | |
| 629 | tetrahydropyrimidin-2-ylamino | 3 | 0 | H | NHCO (4-pyridyl) | |
| 630 | tetrahydropyrimidin-2-ylamino | 3 | 0 | H | NHCOCH$_2$ (2-pyridyl) | |
| 631 | tetrahydropyrimidin-2-ylamino | 3 | 0 | H | NHCOCH$_2$ (3-pyridyl) | |
| 632 | tetrahydropyrimidin-2-ylamino | 3 | 0 | H | NHCOCH$_2$ (4-pyridyl) | |
| 633 | tetrahydropyrimidin-2-ylamino | 3 | 0 | H | NHCO$_2$CH$_2$ (2-pyridyl) | |
| 634 | tetrahydropyrimidin-2-ylamino | 3 | 0 | H | NHCO$_2$CH$_2$ (3-pyridyl) | |
| 635 | tetrahydropyrimidin-2-ylamino | 3 | 0 | H | NHCO$_2$CH$_2$ (4-pyridyl) | |
| 636 | imidazolin-2-ylamino | 3 | 0 | H | H | |
| 637 | imidazolin-2-ylamino | 3 | 0 | H | NHCbz | |
| 638 | imidazolin-2-ylamino | 3 | 0 | H | NHtBOC | |
| 639 | imidazolin-2-ylamino | 3 | 0 | H | NHCO$_2$-nBu | |
| 640 | imidazolin-2-ylamino | 3 | 0 | H | NHCO$_2$Et | |
| 641 | imidazolin-2-ylamino | 3 | 0 | H | NHCO$_2$Me | |
| 642 | imidazolin-2-ylamino | 3 | 0 | H | NHCO(CH$_2$)$_n$Ph | |
| 643 | imidazolin-2-ylamino | 3 | 0 | H | NHCOtBu | |
| 644 | imidazolin-2-ylamino | 3 | 0 | H | NHCO-n-C$_5$H$_{11}$ | |
| 645 | imidazolin-2-ylamino | 3 | 0 | H | NHCO-n-C$_4$H$_9$ | |
| 646 | imidazolin-2-ylamino | 3 | 0 | H | NHCOCH$_2$CH$_3$ | |
| 647 | imidazolin-2-ylamino | 3 | 0 | H | NHCOCH$_3$ | |
| 648 | imidazolin-2-ylamino | 3 | 0 | H | NHSO$_2$CH$_3$ | |
| 649 | imidazolin-2-ylamino | 3 | 0 | H | NHSO$_2$CH$_2$CH$_3$ | |
| 650 | imidazolin-2-ylamino | 3 | 0 | H | NHSO$_2$n-Bu | |
| 651 | imidazolin-2-ylamino | 3 | 0 | H | NHSO$_2$Ph | |
| 652 | imidazolin-2-ylamino | 3 | 0 | H | NHSO$_2$C$_6$H$_4$ (4-CH$_3$) | |
| 653 | imidazolin-2-ylamino | 3 | 0 | H | NHSO$_2$Bn | |
| 654 | imidazolin-2-ylamino | 3 | 0 | H | NHCO (2-pyridyl) | |
| 655 | imidazolin-2-ylamino | 3 | 0 | H | NHCO (3-pyridyl) | |
| 656 | imidazolin-2-ylamino | 3 | 0 | H | NHCO (4-pyridyl) | |
| 657 | imidazolin-2-ylamino | 3 | 0 | H | NHCOCH$_2$ (2-pyridyl) | |
| 658 | imidazolin-2-ylamino | 3 | 0 | H | NHCOCH$_2$ (3-pyridyl) | |
| 659 | imidazolin-2-ylamino | 3 | 0 | H | NHCOCH$_2$ (4-pyridyl) | |
| 660 | imidazolin-2-ylamino | 3 | 0 | H | NHCO$_2$CH$_2$ (2-pyridyl) | |
| 661 | imidazolin-2-ylamino | 3 | 0 | H | NHCO$_2$CH$_2$ (3-pyridyl) | |
| 662 | imidazolin-2-ylamino | 3 | 0 | H | NHCO$_2$CH$_2$ (4-pyridyl) | |
| 663 | pyridin-2-ylamino | 3 | 1 | H | NHCbz | |
| 664 | pyridin-2-ylamino | 3 | 1 | H | NHCO$_2$-n-Bu | |
| 665 | pyridin-2-ylamino | 3 | 1 | H | NHSO$_2$Ph | |
| 666 | pyridin-2-ylamino | 3 | 1 | H | NHSO$_2$-nBu | |
| 667 | pyridin-2-ylamino | 4 | 0 | H | NHCbz | |
| 668 | pyridin-2-ylamino | 4 | 0 | H | NHCO$_2$-n-Bu | |
| 669 | pyridin-2-ylamino | 4 | 0 | H | NHSO$_2$Ph | |
| 670 | pyridin-2-ylamino | 4 | 0 | H | NHSO$_2$-nBu | |
| 671 | pyridin-2-ylamino | 3 | 0 | H | NHCbz | |
| 672 | pyridin-2-ylamino | 3 | 0 | H | NHCO$_2$-n-Bu | |
| 673 | pyridin-2-ylamino | 3 | 0 | H | NHSO$_2$Ph | |
| 674 | pyridin-2-ylamino | 3 | 0 | H | NHSO$_2$-nBu | |
| 675 | imidazol-2-ylamino | 3 | 1 | H | NHCbz | |
| 676 | imidazol-2-ylamino | 3 | 1 | H | NHCO$_2$-n-Bu | |
| 677 | imidazol-2-ylamino | 3 | 1 | H | NHSO$_2$Ph | |
| 678 | imidazol-2-ylamino | 3 | 1 | H | NHSO$_2$-nBu | |
| 679 | imidazol-2-ylamino | 4 | 0 | H | NHCbz | |
| 680 | imidazol-2-ylamino | 4 | 0 | H | NHCO$_2$-n-Bu | |
| 681 | imidazol-2-ylamino | 4 | 0 | H | NHSO$_2$Ph | |
| 682 | imidazol-2-ylamino | 4 | 0 | H | NHSO$_2$-nBu | |
| 683 | imidazol-2-ylamino | 3 | 0 | H | NHCbz | |
| 684 | imidazol-2-ylamino | 3 | 0 | H | NHCO$_2$-n-Bu | |
| 685 | imidazol-2-ylamino | 3 | 0 | H | NHSO$_2$Ph | |
| 686 | imidazol-2-ylamino | 3 | 0 | H | NHSO$_2$-nBu | |
| 687 | thiazol-2-ylamino | 3 | 1 | H | NHCbz | |
| 688 | 2-aminopyridin-6-yl | 3 | 1 | H | NHCO$_2$-n-Bu | |
| 689 | 2-aminopyridin-6-yl | 3 | 1 | H | NHSO$_2$Ph | |
| 690 | 2-aminopyridin-6-yl | 3 | 1 | H | NHSO$_2$-nBu | |
| 691 | 2-aminopyridin-6-yl | 4 | 0 | H | NHCbz | |
| 692 | 2-aminopyridin-6-yl | 4 | 0 | H | NHCO$_2$-n-Bu | |
| 693 | 2-aminopyridin-6-yl | 4 | 0 | H | NHSO$_2$Ph | |
| 694 | 2-aminopyridin-6-yl | 4 | 0 | H | NHSO$_2$-nBu | |
| 695 | 2-aminopyridin-6-yl | 3 | 0 | H | NHCbz | |
| 696 | 2-aminopyridin-6-yl | 3 | 0 | H | NHCO$_2$-n-Bu | |

TABLE 2-continued

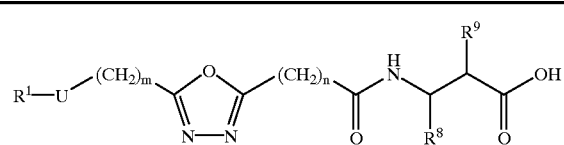

| Ex. No. | R¹-U | m | n | R⁸ | R¹⁶ | MS |
|---|---|---|---|---|---|---|
| 697 | 2-aminopyridin-6-yl | 3 | 0 | H | NHSO$_2$Ph | |
| 698 | 2-aminopyridin-6-yl | 3 | 0 | H | NHSO$_2$-nBu | |
| 699 | 2-aminopyridin-3-yl | 2 | 0 | H | NHCbz | |
| 700 | 2-aminopyridin-3-yl | 2 | 0 | H | NHCO$_2$-n-Bu | |
| 701 | 2-aminopyridin-3-yl | 2 | 0 | H | NHSO$_2$Ph | |
| 702 | 2-aminopyridin-3-yl | 2 | 0 | H | NHSO$_2$-nBu | |
| 703 | 2-aminothiazol-4-yl | 3 | 1 | H | NHCbz | |
| 704 | 2-aminothiazol-4-yl | 3 | 1 | H | NHCO$_2$-n-Bu | |
| 705 | 2-aminothiazol-4-yl | 3 | 1 | H | NHSO$_2$Ph | |
| 706 | 2-aminothiazol-4-yl | 3 | 1 | H | NHSO$_2$-nBu | |
| 707 | 2-aminothiazol-4-yl | 4 | 0 | H | NHCbz | |
| 708 | 2-aminothiazol-4-yl | 4 | 0 | H | NHCO$_2$-n-Bu | |
| 709 | 2-aminothiazol-4-yl | 4 | 0 | H | NHSO$_2$Ph | |
| 710 | 2-aminopyridin-6-yl | 4 | 0 | H | NHSO$_2$-nBu | |
| 711 | 2-aminothiazol-4-yl | 3 | 0 | H | NHCbz | |
| 712 | 2-aminothiazol-4-yl | 3 | 0 | H | NHCO$_2$-n-Bu | |
| 713 | 2-aminothiazol-4-yl | 3 | 0 | H | NHSO$_2$Ph | |
| 714 | 2-aminothiazol-4-yl | 3 | 0 | H | NHSO$_2$-nBu | |
| 715 | 2-aminothiazol-4-yl | 3 | 1 | H | NHCbz | |
| 716 | 2-aminothiazol-4-yl | 3 | 1 | H | NHCO$_2$-n-Bu | |
| 717 | 1,3,4-thiadiazol-2-ylamino | 3 | 1 | H | NHSO$_2$Ph | |
| 718 | 1,3,4-thiadiazol-2-ylamino | 3 | 1 | H | NHSO$_2$-nBu | |
| 719 | 1,3,4-thiadiazol-2-ylamino | 4 | 0 | H | NHCbz | |
| 720 | 1,3,4-thiadiazol-2-ylamino | 4 | 0 | H | NHCO$_2$-n-Bu | |
| 721 | 1,3,4-thiadiazol-2-ylamino | 4 | 0 | H | NHSO$_2$Ph | |
| 722 | 1,3,4-thiadiazol-2-ylamino | 4 | 0 | H | NHSO$_2$-nBu | |
| 723 | 1,3,4-thiadiazol-2-ylamino | 3 | 0 | H | NHCbz | |
| 724 | 1,3,4-thiadiazol-2-ylamino | 3 | 0 | H | NHCO$_2$-n-Bu | |
| 725 | 1,3,4-thiadiazol-2-ylamino | 3 | 0 | H | NHSO$_2$Ph | |
| 726 | 1,2,4-thiadiazol-5-ylamino | 3 | 0 | H | NHSO$_2$-nBu | |
| 727 | 1,2,4-thiadiazol-5-ylamino | 3 | 1 | H | NHCbz | |
| 728 | 1,2,4-thiadiazol-5-ylamino | 3 | 1 | H | NHCO$_2$-n-Bu | |
| 729 | 1,2,4-thiadiazol-5-ylamino | 3 | 1 | H | NHSO$_2$Ph | |
| 730 | 1,2,4-thiadiazol-5-ylamino | 3 | 1 | H | NHSO$_2$-nBu | |
| 731 | 1,2,4-thiadiazol-5-ylamino | 4 | 0 | H | NHCbz | |
| 732 | 1,2,4-thiadiazol-5-ylamino | 4 | 0 | H | NHCO$_2$-n-Bu | |
| 733 | 1,2,4-thiadiazol-5-ylamino | 4 | 0 | H | NHSO$_2$Ph | |
| 734 | 1,2,4-thiadiazol-5-ylamino | 4 | 0 | H | NHSO$_2$-nBu | |
| 735 | 1,2,4-thiadiazol-5-ylamino | 3 | 0 | H | NHCbz | |
| 736 | 1,2,4-thiadiazol-5-ylamino | 3 | 0 | H | NHCO$_2$-n-Bu | |
| 737 | 1,2,4-thiadiazol-5-ylamino | 3 | 0 | H | NHSO$_2$Ph | |
| 738 | isoxazol-3-ylamino | 3 | 0 | H | NHSO$_2$-nBu | |
| 739 | isoxazol-3-ylamino | 3 | 1 | H | NHCbz | |
| 740 | isoxazol-3-ylamino | 3 | 1 | H | NHCO$_2$-n-Bu | |
| 741 | isoxazol-3-ylamino | 3 | 1 | H | NHSO$_2$Ph | |
| 742 | isoxazol-3-ylamino | 3 | 1 | H | NHSO$_2$-nBu | |
| 743 | isoxazol-3-ylamino | 4 | 0 | H | NHCbz | |

TABLE 2-continued

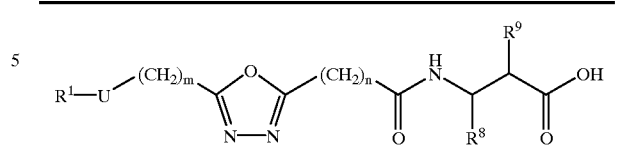

| Ex. No. | R¹-U | m | n | R⁸ | R¹⁶ | MS |
|---|---|---|---|---|---|---|
| 744 | isoxazol-3-ylamino | 4 | 0 | H | NHCO$_2$-n-Bu | |
| 745 | isoxazol-3-ylamino | 4 | 0 | H | NHSO$_2$Ph | |
| 746 | isoxazol-3-ylamino | 4 | 0 | H | NHSO$_2$-nBu | |
| 747 | isoxazol-3-ylamino | 3 | 0 | H | NHCbz | |
| 748 | isoxazol-3-ylamino | 3 | 0 | H | NHCO$_2$-n-Bu | |
| 749 | isoxazol-3-ylamino | 3 | 0 | H | NHSO$_2$Ph | |
| 750 | oxazol-2-ylamino | 3 | 0 | H | NHSO$_2$-nBu | |
| 751 | oxazol-2-ylamino | 3 | 1 | H | NHCbz | |
| 752 | oxazol-2-ylamino | 3 | 1 | H | NHCO$_2$-n-Bu | |
| 753 | oxazol-2-ylamino | 3 | 1 | H | NHSO$_2$Ph | |
| 754 | oxazol-2-ylamino | 3 | 1 | H | NHSO$_2$-nBu | |
| 755 | oxazol-2-ylamino | 4 | 0 | H | NHCbz | |
| 756 | oxazol-2-ylamino | 4 | 0 | H | NHCO$_2$-n-Bu | |
| 757 | oxazol-2-ylamino | 4 | 0 | H | NHSO$_2$Ph | |
| 758 | oxazol-2-ylamino | 4 | 0 | H | NHSO$_2$-nBu | |
| 759 | oxazol-2-ylamino | 3 | 0 | H | NHCbz | |
| 760 | oxazol-2-ylamino | 3 | 0 | H | NHCO$_2$-n-Bu | |
| 761 | oxazol-2-ylamino | 3 | 0 | H | NHSO$_2$Ph | |
| 762 | oxazol-2-ylamino | 3 | 0 | H | NHSO$_2$-nBu | |
| 763 | 1,2,5-thiadiazol-3-ylamino | 3 | 1 | H | NHCbz | |
| 764 | 1,2,5-thiadiazol-3-ylamino | 3 | 1 | H | NHCO$_2$-n-Bu | |
| 765 | 1,2,5-thiadiazol-3-ylamino | 3 | 1 | H | NHSO$_2$Ph | |
| 766 | 1,2,5-thiadiazol-3-ylamino | 3 | 1 | H | NHSO$_2$-nBu | |
| 767 | 1,2,5-thiadiazol-3-ylamino | 4 | 0 | H | NHCbz | |
| 768 | 1,2,5-thiadiazol-3-ylamino | 4 | 0 | H | NHCO$_2$-n-Bu | |
| 769 | 1,2,5-thiadiazol-3-ylamino | 4 | 0 | H | NHSO$_2$Ph | |
| 770 | 1,2,5-thiadiazol-3-ylamino | 4 | 0 | H | NHSO$_2$-nBu | |
| 771 | 1,2,5-thiadiazol-3-ylamino | 3 | 0 | H | NHCbz | |
| 772 | 1,2,5-thiadiazol-3-ylamino | 3 | 0 | H | NHCO$_2$-n-Bu | |
| 773 | 1,2,5-thiadiazol-3-ylamino | 3 | 0 | H | NHSO$_2$Ph | |
| 774 | 1,2,5-thiadiazol-3-ylamino | 3 | 0 | H | NHSO$_2$-nBu | |
| 775 | imidazolin-2-ylamino | 2 | 2 | H | NHCbz | |
| 776 | imidazolin-2-ylamino | 2 | 2 | H | NHCO$_2$-n-Bu | |
| 777 | imidazolin-2-ylamino | 2 | 2 | H | NHSO$_2$Ph | |
| 778 | imidazolin-2-ylamino | 2 | 2 | H | NHSO$_2$-nBu | |
| 779 | tetrahydropyrimidin-2-ylamino | 2 | 2 | H | NHCbz | |
| 780 | tetrahydropyrimidin-2-ylamino | 2 | 2 | H | NHCO$_2$-n-Bu | |
| 781 | tetrahydropyrimidin-2-ylamino | 2 | 2 | H | NHSO$_2$Ph | |
| 782 | tetrahydropyrimidin-2-ylamino | 2 | 2 | H | NHSO$_2$-nBu | |
| 783 | benzimidazol-2-ylamino | 4 | 0 | H | NHCbz | |
| 784 | benzthiazol-2-ylamino | 4 | 0 | H | NHCbz | |
| 785 | 1,2-pyrazol-3-ylamino | 4 | 0 | H | NHCbz | |
| 786 | 1,2,4-triazol-5-ylamino | 4 | 0 | H | NHCbz | |
| 787 | imidazol-4-ylamino | 4 | 0 | H | NHCbz | |

TABLE 2-continued $$R^1-U-(CH_2)_m-\underset{N-N}{\underset{|}{\text{oxadiazole}}}-(CH_2)_n-\overset{H}{N}-\overset{R^9}{\underset{R^8}{C}}-COOH$$

| Ex. No. | R¹-U | m | n | R⁸ | R¹⁶ | MS |
|---|---|---|---|---|---|---|
| 788 | 1,3,4-oxadiazol-2-ylamino | 4 | 0 | H | NHCbz | |
| 789 | 1,2,4-thiadiazol-5-ylamino | 4 | 0 | H | NHCbz | |
| 790 | 1,2,4-thiadiazol-3-ylamino | 4 | 0 | H | NHCbz | |
| 791 | 1,2,5-oxadiazol-3-ylamino | 4 | 0 | H | NHCbz | |
| 792 | 1,2,4-oxadiazol-5-ylamino | 4 | 0 | H | NHCbz | |
| 793 | 1,2,4-oxadiazol-3-ylamino | 4 | 0 | H | NHCbz | |
| 794 | 2-iminopyrrolidin-5-yl | 3 | 1 | H | NHCbz | |
| 795 | 2-iminopyrrolidin-5-yl | 3 | 1 | H | NHSO₂Ph | |
| 796 | 2-iminopyrrolidin-5-yl | 3 | 0 | H | NHCbz | |
| 797 | 2-iminopyrrolidin-5-yl | 3 | 0 | H | NHSO₂Ph | |
| 798 | 2-iminopyrrolidin-5-yl | 2 | 1 | H | NHCbz | |
| 799 | 2-iminopyrrolidin-5-yl | 2 | 1. | H | NHSO₂Ph | |
| 800 | 2-iminopiperidin-6-yl | 3 | 1 | H | NHCbz | |
| 801 | 2-iminopiperidin-6-yl | 3 | 1 | H | NHSO₂Ph | |
| 802 | 2-iminopiperidin-6-yl | 3 | 0 | H | NHCbz | |
| 803 | 2-iminopiperidin-6-yl | 3 | 0 | H | NHSO₂Ph | |
| 804 | 2-iminopiperidin-6-yl | 2 | 1 | H | NHCbz | |
| 805 | 2-iminopiperidin-6-yl | 2 | 1 | H | NHSO₂Ph | |
| 806 | 2-iminoazepin-7-yl | 3 | 1 | H | NHCbz | |
| 807 | 2-iminoazepin-7-yl | 3 | 1 | H | NHSO₂Ph | |
| 808 | 2-iminoazepin-7-yl | 3 | 0 | H | NHCbz | |
| 809 | 2-iminoazepin-7-yl | 3 | 0 | H | NHSO₂Ph | |
| 810 | 2-iminoazepin-7-yl | 2 | 1 | H | NHCbz | |
| 811 | 2-iminoazepin-7-yl | 2 | 1 | H | NHSO₂Ph | |
| 812 | benzimidazol-2-ylamino | 4 | 0 | n-Bu | H | |
| 813 | benzthiazol-2-ylamino | 4 | 0 | n-Bu | H | |
| 814 | 1,2-pyrazol-3-ylamino | 4 | 0 | n-Bu | H | |
| 815 | 1,2,4-triazol-5-ylamino | 4 | 0 | n-Bu | H | |
| 816 | imidazol-4-ylamino | 4 | 0 | n-Bu | H | |
| 817 | 1,3,4-oxadiazol-2-ylamino | 4 | 0 | n-Bu | H | |
| 818 | 1,2,4-thiadiazol-5-ylamino | 4 | 0 | n-Bu | H | |
| 819 | 1,2,4-thiadiazol-3-ylamino | 4 | 0 | n-Bu | H | |
| 820 | 1,2,5-oxadiazol-3-ylamino | 4 | 0 | n-Bu | H | |
| 821 | 1,2,4-oxadiazol-5-ylamino | 4 | 0 | n-Bu | H | |
| 822 | 1,2,4-oxadiazol-3-ylamino | 4 | 0 | n-Bu | H | |

TABLE 3

$$R^1-U-(CH_2)_m-\underset{N-N}{\underset{|}{\text{G}}}-S-(CH_2)_n-\overset{H}{N}-\overset{R^9}{\underset{R^8}{C}}-COOH$$

| Ex. No. | R¹-U | m | n | G | R⁸ | R⁹ |
|---|---|---|---|---|---|---|
| 1001 | imidazolin-2-ylamino | 3 | 0 | O | H | H |
| 1002 | imidazolin-2-ylamino | 2 | 0 | O | H | H |
| 1003 | imidazolin-2-ylamino | 2 | 0 | O | H | NHCbz |
| 1004 | imidazolin-2-ylamino | 3 | 0 | O | H | NHCbz |
| 1005 | imidazolin-2-ylamino | 2 | 0 | S | H | NHCbz |
| 1006 | imidazolin-2-ylamino | 3 | 0 | S | H | NHCbz |
| 1009 | tetrahydropyrimidin-2-ylamino | 2 | 0 | O | H | H |
| 1010 | tetrahydropyrimidin-2-ylamino | 2 | 0 | O | H | NHCbz |
| 1011 | tetrahydropyrimidin-2-ylamino | 3 | 0 | O | H | H |
| 1012 | tetrahydropyrimidin-2-ylamino | 3 | 0 | O | H | NHCbz |
| 1013 | tetrahydropyrimidin-2-ylamino | 2 | 0 | S | H | NHCbz |
| 1014 | tetrahydropyrimidin-2-ylamino | 3 | 0 | S | H | NHCbz |
| 1015 | tetrahydropyrimidin-2-ylamino | 2 | 0 | O | H | NHCbz |
| 1017 | imidazolin-2-ylamino | 2 | 0 | O | H | NH-n-Bu |
| 1018 | imidazolin-2-ylamino | 3 | 0 | O | H | NH-n-Bu |
| 1019 | imidazolin-2-ylamino | 2 | 0 | S | H | NH-n-Bu |
| 1020 | imidazolin-2-ylamino | 3 | 0 | S | H | NH-n-Bu |
| 1023 | tetrahydropyrimidin-2-ylamino | 2 | 0 | O | H | NH-n-Bu |
| 1024 | tetrahydropyrimidin-2-ylamino | 3 | 0 | O | H | NH-n-Bu |
| 1025 | tetrahydropyrimidin-2-ylamino | 2 | 0 | S | H | NH-n-Bu |
| 1026 | tetrahydropyrimidin-2-ylamino | 3 | 0 | S | H | NH-n-Bu |
| 1027 | tetrahydropyrimidin-2-ylamino | 2 | 0 | S | H | NH-n-Bu |
| 1028 | tetrahydropyrimidin-2-ylamino | 3 | 0 | O | H | NH-n-Bu |
| 1029 | imidazolin-2-ylamino | 2 | 0 | O | H | NHSO₂Ph (o-CH₃) |
| 1030 | imidazolin-2-ylamino | 3 | 0 | O | H | NHSO₂Ph (o-CH₃) |
| 1031 | imidazolin-2-ylamino | 2 | 0 | S | H | NHSO₂Ph (o-CH₃) |
| 1032 | imidazolin-2-ylamino | 3 | 0 | S | H | NHSO₂Ph (o-CH₃) |
| 1033 | imidazolin-2-ylamino | 2 | 0 | O | H | NHSO₂Ph (m-CH₃) |
| 1034 | imidazolin-2-ylamino | 3 | 0 | O | H | NHSO₂Ph (m-CH₃) |
| 1035 | imidazolin-2-ylamino | 2 | 0 | S | H | NHSO₂Ph (m-CH₃) |
| 1036 | imidazolin-2-ylamino | 3 | 0 | S | H | NHSO₂Ph (m-CH₃) |
| 1037 | imidazolin-2-ylamino | 2 | 0 | O | H | NHSO₂Ph (p-CH₃) |
| 1038 | imidazolin-2-ylamino | 3 | 0 | O | H | NHSO₂Ph (p-CH₃) |
| 1039 | imidazolin-2-ylamino | 2 | 0 | S | H | NHSO₂Ph (p-CH₃) |
| 1040 | imidazolin-2-ylamino | 3 | 0 | S | H | NHSO₂Ph (p-CH₃) |
| 1041 | imidazolin-2-ylamino | 2 | 0 | O | H | SO₂Ph (o-Cl) |
| 1042 | imidazolin-2-ylamino | 3 | 0 | O | H | SO₂Ph (o-Cl) |
| 1043 | imidazolin-2-ylamino | 2 | 0 | O | H | SO₂Ph (m-Cl) |
| 1044 | imidazolin-2-ylamino | 3 | 0 | O | H | SO₂Ph (m-Cl) |
| 1045 | imidazolin-2-ylamino | 2 | 0 | O | H | SO₂Ph (p-Cl) |
| 1046 | imidazolin-2-ylamino | 3 | 0 | O | H | SO₂Ph (p-Cl) |
| 1047 | tetrahydropyrimidin-2-ylamino | 2 | 0 | O | H | SO₂Ph (p-Cl) |

TABLE 3-continued

| Ex. No. | R¹-U | m | n | Q | R⁸ | R⁹ |
|---|---|---|---|---|---|---|
| 1048 | tetrahydropyrimidin-2-ylamino | 3 | 0 | O | H | SO₂Ph (p-Cl) |
| 1049 | imidazolin-2-ylamino | 2 | 0 | O | H | SO₂Ph (m-Cl) |
| 1050 | tetrahydropyrimidin-2-ylamino | 3 | 0 | O | H | SO₂Ph (m-Cl) |
| 1051 | tetrahydropyrimidin-2-ylamino | 2 | 0 | O | H | SO₂Ph (p-Cl) |
| 1052 | tetrahydropyrimidin-2-ylamino | 3 | 0 | O | H | SO₂Ph (p-Cl) |
| 1053 | imidazolin-2-ylamino | 2 | 0 | O | H | NHPh (m-F) |
| 1054 | imidazolin-2-ylamino | 3 | 0 | O | H | NHPh (m-F) |
| 1055 | tetrahydropyrimidin-2-ylamino | 2 | 0 | O | H | NHPh (m-F) |
| 1056 | tetrahydropyrimidin-2-ylamino | 3 | 0 | O | H | NHPh (m-F) |
| 1057 | imidazolin-2-ylamino | 2 | 0 | O | H | NHPh (p-F) |
| 1058 | imidazolin-2-ylamino | 3 | 0 | O | H | NHPh (p-F) |
| 1059 | tetrahydropyrimidin-2-ylamino | 2 | 0 | O | H | NHPh (p-F) |
| 1060 | tetrahydropyrimidin-2-ylamino | 3 | 0 | O | H | NHPh (p-F) |
| 1061 | imidazolin-2-ylamino | 2 | 0 | O | H | NHPh (m-Br) |
| 1062 | imidazolin-2-ylamino | 3 | 0 | O | H | NHPh (m-Br) |
| 1063 | tetrahydropyrimidin-2-ylamino | 2 | 0 | O | H | NHPh (m-Br) |
| 1064 | tetrahydropyrimidin-2-ylamino | 3 | 0 | O | H | NHPh (m-Br) |
| 1065 | imidazolin-2-ylamino | 2 | 0 | O | H | NHSO₂Ph (p-Br) |
| 1066 | imidazolin-2-ylamino | 3 | 0 | O | H | NHSO₂Ph (p-Br) |
| 1067 | tetrahydropyrimidin-2-ylamino | 2 | 0 | O | H | NHSO₂Ph (p-Br) |
| 1068 | tetrahydropyrimidin-2-ylamino | 3 | 0 | O | H | NHSO₂Ph (p-Br) |
| 1069 | imidazolin-2-ylamino | 2 | 0 | O | H | NHSO₂Ph (m-OCH₃) |
| 1070 | imidazolin-2-ylamino | 3 | 0 | O | H | NHSO₂Ph (m-OCH₃) |
| 1071 | tetrahydropyrimidin-2-ylamino | 2 | 0 | O | H | NHSO₂Ph (m-OCH₃) |
| 1072 | tetrahydropyrimidin-2-ylamino | 3 | 0 | O | H | NHSO₂Ph (m-OCH₃) |
| 1073 | imidazolin-2-ylamino | 2 | 0 | O | H | NHSO₂Ph (p-OCH₃) |
| 1074 | imidazolin-2-ylamino | 3 | 0 | O | H | NHSO₂Ph (p-OCH₃) |
| 1075 | tetrahydropyrimidin-2-ylamino | 2 | 0 | O | H | NHSO₂Ph (p-OCH₃) |
| 1076 | tetrahydropyrimidin-2-ylamino | 3 | 0 | O | H | NHSO₂Ph (p-OCH₃) |
| 1077 | imidazolin-2-ylamino | 2 | 0 | O | H | NHSO₂Bn |
| 1078 | imidazolin-2-ylamino | 3 | 0 | O | H | NHSO₂Bn |
| 1079 | tetrahydropyrimidin-2-ylamino | 2 | 0 | O | H | NHSO₂Bn |
| 1080 | tetrahydropyrimidin-2-ylamino | 3 | 0 | O | H | NHSO₂Bn |
| 1081 | imidazolin-2-ylamino | 2 | 0 | O | H | NHSO₂Et |
| 1082 | imidazolin-2-ylamino | 3 | 0 | O | H | NHSO₂Et |
| 1083 | tetrahydropyrimidin-2-ylamino | 2 | 0 | O | H | NHSO₂Et |
| 1084 | tetrahydropyrimidin-2-ylamino | 3 | 0 | O | H | NHSO₂Et |

| Ex. No. | R¹-U | m | n | Q | R⁸ | R⁹ |
|---|---|---|---|---|---|---|
| 1085 | imidazolin-2-ylamino | 2 | 0 | O | H | NHSO₂-n-Pr |
| 1086 | imidazolin-2-ylamino | 3 | 0 | O | H | NHSO₂-n-Pr |
| 1087 | tetrahydropyrimidin-2-ylamino | 2 | 0 | O | H | NHSO₂-n-Pr |
| 1088 | tetrahydropyrimidin-2-ylamino | 3 | 0 | O | H | NHSO₂-n-Pr |
| 1089 | imidazolin-2-ylamino | 2 | 0 | O | H | NHSO₂-n-(C₅H₁₁) |
| 1090 | imidazolin-2-ylamino | 3 | 0 | O | H | NHSO₂-n-(C₅H₁₁) |
| 1091 | tetrahydropyrimidin-2-ylamino | 2 | 0 | O | H | NHSO₂-n-(C₅H₁₁) |
| 1092 | tetrahydropyrimidin-2-ylamino | 3 | 0 | O | H | NHSO₂-n-(C₅H₁₁) |
| 1093 | imidazolin-2-ylamino | 2 | 0 | O | H | NHCO₂Et |
| 1094 | imidazolin-2-ylamino | 3 | 0 | O | H | NHCO₂Et |
| 1095 | tetrahydropyrimidin-2-ylamino | 2 | 0 | O | H | NHCO₂Et |
| 1096 | tetrahydropyrimidin-2-ylamino | 3 | 0 | O | H | NHCO₂Et |
| 1097 | imidazolin-2-ylamino | 2 | 0 | O | H | NHCO₂-n-C₅H₁₁ |
| 1098 | imidazolin-2-ylamino | 3 | 0 | O | H | NHCO₂-n-C₅H₁₁ |
| 1099 | tetrahydropyrimidin-2-ylamino | 2 | 0 | O | H | NHCO₂-n-C₅H₁₁ |
| 1100 | tetrahydropyrimidin-2-ylamino | 3 | 0 | O | H | NHCO₂-n-C₅H₁₁ |
| 1101 | imidazolin-2-ylamino | 4 | 0 | O | H | NHCbz |
| 1102 | tetrahydropyrimidin-2-ylamino | 4 | 0 | O | H | NHCbz |
| 1103 | imidazolin-2-ylamino | 4 | 0 | O | H | NHCO₂-n-Bu |
| 1104 | tetrahydropyrimidin-2-ylamino | 4 | 0 | O | H | NHCO₂-n-Bu |
| 1105 | imidazolin-2-ylamino | 4 | 0 | O | H | NHSO₂Ph |
| 1106 | tetrahydropyrimidin-2-ylamino | 4 | 0 | O | H | NHSO₂Ph |
| 1107 | imidazolin-2-ylamino | 4 | 0 | O | H | NHSO₂-n-Bu |
| 1108 | tetrahydropyrimidin-2-ylamino | 4 | 0 | O | H | NHSO₂-n-Bu |
| 1109 | imidazolin-2-ylamino | 4 | 0 | S | H | NHCbz |
| 1110 | tetrahydropyrimidin-2-ylamino | 4 | 0 | S | H | NHCbz |
| 1111 | imidazolin-2-ylamino | 4 | 0 | S | H | NHSO₂Bu |
| 1112 | tetrahydropyrimidin-2-ylamino | 4 | 0 | S | H | NHSO₂Bu |
| 1113 | imidazolin-2-ylamino | 2 | 0 | O | Me | H |
| 1114 | imidazolin-2-ylamino | 3 | 0 | O | Me | H |

| Ex. No. | R¹-U | m | n | G | R⁸ | R⁹ |
|---|---|---|---|---|---|---|
| 1115 | tetrahydropyrimidin-2-ylamino | 2 | 0 | O | Me | H |
| 1116 | tetrahydropyrimidin-2-ylamino | 3 | 0 | O | Me | H |
| 1117 | imidazolin-2-ylamino | 3 | 0 | S | Me | H |
| 1118 | tetrahydropyrimidin-2-ylamino | 3 | 0 | S | Me | H |
| 1119 | imidazolin-2-ylamino | 2 | 0 | O | Me | NHCbz |
| 1120 | imidazolin-2-ylamino | 3 | 0 | O | Me | NHCbz |
| 1121 | tetrahydropyrimidin-2-ylamino | 2 | 0 | O | Me | NHSO₂-n-Bu |
| 1122 | tetrahydropyrimidin-2-ylamino | 3 | 0 | O | Me | NHSO₂-n-Bu |
| 1123 | imidazolin-2-ylamino | 2 | 0 | O | Et | H |
| 1124 | imidazolin-2-ylamino | 3 | 0 | O | Et | H |
| 1125 | tetrahydropyrimidin-2-ylamino | 2 | 0 | O | Et | H |
| 1126 | tetrahydropyrimidin-2-ylamino | 3 | 0 | O | Et | H |
| 1127 | imidazolin-2-ylamino | 3 | 0 | S | Et | H |
| 1128 | tetrahydropyrimidin-2-ylamino | 3 | 0 | S | Et | H |
| 1129 | imidazolin-2-ylamino | 2 | 0 | O | Ph | H |
| 1130 | imidazolin-2-ylamino | 3 | 0 | O | Ph | H |
| 1131 | tetrahydropyrimidin-2-ylamino | 2 | 0 | O | Ph | H |
| 1132 | tetrahydropyrimidin-2-ylamino | 3 | 0 | O | Ph | H |
| 1133 | imidazolin-2-ylamino | 3 | 0 | S | Ph | H |
| 1134 | tetrahydropyrimidin-2-ylamino | 3 | 0 | S | Ph | H |
| 1135 | imidazolin-2-ylamino | 2 | 0 | O | Bn | H |
| 1136 | imidazolin-2-ylamino | 3 | 0 | O | Bn | H |
| 1137 | tetrahydropyrimidin-2-ylamino | 2 | 0 | O | Bn | H |
| 1138 | tetrahydropyrimidin-2-ylamino | 3 | 0 | O | Bn | H |
| 1139 | imidazolin-2-ylamino | 3 | 0 | S | Bn | H |
| 1140 | tetrahydropyrimidin-2-ylamino | 3 | 0 | S | Bn | H |
| 1141 | imidazolin-2-ylamino | 2 | 0 | O | H | NHCbz |

TABLE 3-continued

| Ex. No. | R¹-U | m | n | Q | R⁸ | R⁹ |
|---|---|---|---|---|---|---|
| 1142 | imidazolin-2-ylamino | 3 | 0 | O | H | NHCbz |
| 1143 | tetrahydropyrimidin-2-ylamino | 2 | 0 | O | H | NHCbz |
| 1144 | tetrahydropyrimidin-2-ylamino | 3 | 0 | O | H | NHCbz |
| 1145 | imidazolin-2-ylamino | 2 | 0 | O | H | NHSO$_2$-n-Bu |
| 1146 | imidazolin-2-ylamino | 3 | 0 | O | H | NHSO$_2$-n-Bu |
| 1147 | tetrahydropyrimidin-2-ylamino | 2 | 0 | O | H | NHSO$_2$-n-Bu |
| 1148 | tetrahydropyrimidin-2-ylamino | 3 | 0 | O | H | NHSO$_2$-n-Bu |
| 1149 | imidazolin-2-ylamino | 3 | 0 | S | H | NHCbz |
| 1150 | tetrahydropyrimidin-2-ylamino | 3 | 0 | S | H | NHCbz |
| 1151 | imidazolin-2-ylamino | 3 | 0 | S | H | NHSO$_2$-n-Bu |
| 1152 | tetrahydropyrimidin-2-ylamino | 3 | 0 | S | H | NHSO$_2$-n-Bu |
| 1153 | imidazolin-2-ylamino | 2 | 0 | O | H | NHCbz |
| 1154 | imidazolin-2-ylamino | 3 | 0 | O | H | NHCbz |
| 1155 | tetrahydropyrimidin-2-ylamino | 2 | 0 | O | H | NHCbz |
| 1156 | tetrahydropyrimidin-2-ylamino | 3 | 0 | O | H | NHCbz |
| 1157 | imidazolin-2-ylamino | 2 | 0 | O | H | NHSO$_2$-n-Bu |
| 1158 | imidazolin-2-ylamino | 3 | 0 | O | H | NHSO$_2$-n-Bu |
| 1159 | tetrahydropyrimidin-2-ylamino | 2 | 0 | O | H | NHSO$_2$-n-Bu |
| 1160 | tetrahydropyrimidin-2-ylamino | 3 | 0 | O | H | NHSO$_2$-n-Bu |
| 1161 | imidazolin-2-ylamino | 3 | 0 | S | H | NHCbz |
| 1162 | tetrahydropyrimidin-2-ylamino | 3 | 0 | S | H | NHCbz |
| 1163 | imidazolin-2-ylamino | 3 | 0 | S | H | NHSO$_2$-n-Bu |
| 1164 | tetrahydropyrimidin-2-ylamino | 3 | 0 | S | H | NHSO$_2$-n-Bu |
| 1165 | imidazolin-2-ylamino | 3 | 0 | O | Me | NHCbz |
| 1166 | tetrahydropyrimidin-2-ylamino | 3 | 0 | O | Me | NHSO$_2$Bu |
| 1167 | imidazolin-2-ylamino | 3 | 0 | O | Bn | NHCbz |
| 1168 | tetrahydropyrimidin-2-ylamino | 3 | 0 | O | Bn | NHCbz |
| 1169 | imidazolin-2-ylamino | 3 | 0 | O | Me | NHSO$_2$-n-Bu |
| 1170 | tetrahydropyrimidin-2-ylamino | 3 | 0 | O | Me | NHCbz |
| 1171 | imidazolin-2-ylamino | 3 | 0 | O | Bn | NHSO$_2$-n-Bu |
| 1172 | tetrahydropyrimidin-2-ylamino | 3 | 0 | O | Bn | NHCbz |
| 1173 | (4-oxoimidazolin-2-yl)amino | 2 | 0 | O | H | NHCBz |
| 1174 | (4-oxoimidazolin-2-yl)amino | 3 | 0 | O | H | NHCBz |
| 1175 | (4-oxoimidazolin-2-yl)amino | 2 | 0 | O | H | NHCO$_2$-n-Bu |
| 1176 | (4-oxoimidazolin-2-yl)amino | 3 | 0 | O | H | NHCO$_2$-n-Bu |
| 1177 | (4-oxoimidazolin-2-yl)amino | 2 | 0 | O | H | NHSO$_2$Ph |
| 1178 | (4-oxoimidazolin-2-yl)amino | 3 | 0 | O | H | NHSO$_2$Ph |
| 1179 | (4-oxoimidazolin-2-yl)amino | 2 | 0 | O | H | NHSO$_2$-n-Bu |
| 1180 | (4-oxoimidazolin-2-yl)amino | 3 | 0 | O | H | NHSO$_2$-n-Bu |
| 1181 | (4-oxotetrahydro-pyrimidin-2-yl)amino | 3 | 0 | O | H | NHCbz |
| 1182 | (4-oxotetrahydro-pyrimidin-2-yl)amino | 3 | 0 | O | H | NHCO$_2$-n-Bu |
| 1183 | (4-oxotetrahydro-pyrimidin-2-yl)amino | 3 | 0 | O | H | NHSO$_2$Ph |
| 1184 | (4-oxotetrahydro-pyrimidin-2-yl)amino | 3 | 0 | O | H | NHSO$_2$-n-Bu |
| 1185 | (4-oxoimidazolin-2-yl)amino | 3 | 0 | S | H | NHCbz |
| 1186 | (4-oxoimidazolin-2-yl)amino | 3 | 0 | S | H | NHSO$_2$-n-Bu |
| 1187 | (4-oxotetrahydro-pyrimidin-2-yl)amino | 3 | 0 | S | H | NHCbz |
| 1188 | (4-oxotetrahydro-pyrimidin-2-yl)amino | 3 | 0 | S | H | NHSO$_2$-n-Bu |
| 1189 | (4-oxoimidazolin-2-yl)amino | 3 | 0 | O | Me | H |
| 1190 | (4-oxotetrahydro-pyrimidin-2-yl)amino | 3 | 0 | O | Me | H |
| 1191 | (4-oxoimidazolin-2-yl)amino | 3 | 0 | O | Bn | H |

| Ex. No. | R¹-U | m | n | Q | R⁸ | R⁹ |
|---|---|---|---|---|---|---|
| 1192 | (4-oxotetrahydro-pyrimidin-2-yl)amino | 3 | 0 | O | Bn | H |
| 1193 | (4-oxoimidazolin-2-yl)amino | 3 | 0 | O | Me | NHCbz |
| 1194 | (4-oxotetrahydro-pyrimidin-2-yl)amino | 3 | 0 | O | Me | NHSO$_2$-n-Bu |
| 1195 | (4-oxoimidazolin-2-yl)amino | 3 | 0 | O | H | NHCbz |
| 1196 | (4-oxotetrahydro-pyrimidin-2-yl)amino | 3 | 0 | O | H | NHCbz |
| 1197 | imidazolin-2-ylaminocarbonyl | 1 | 0 | O | H | NHCbz |
| 1198 | imidazolin-2-ylaminocarbonyl | 2 | 0 | O | H | NHCbz |
| 1199 | tetrahydropyrimidin-2-ylaminocarbonyl | 1 | 0 | O | H | NHSO$_2$-n-Bu |
| 1200 | tetrahydropyrimidin-2-ylaminocarbonyl | 2 | 0 | O | H | NHSO$_2$-n-Bu |
| 1201 | imidazolin-2-ylaminocarbonyl | 2 | 0 | O | H | NHCbz |
| 1202 | tetrahydropyrimidin-2-ylaminocarbonyl | 2 | 0 | O | H | NHSO$_2$-n-Bu |
| 1203 | imidazolin-2-ylaminocarbonyl | 1 | 0 | O | H | NHCO$_2$-n-Bu |
| 1204 | imidazolin-2-ylaminocarbonyl | 2 | 0 | O | H | NHCO$_2$-n-Bu |
| 1205 | tetrahydropyrimidin-2-ylaminocarbonyl | 1 | 0 | O | H | NHSO$_2$Ph |
| 1206 | tetrahydropyrimidin-2-ylaminocarbonyl | 2 | 0 | O | H | NHSO$_2$Ph |
| 1207 | imidazolin-2-ylaminocarbonyl | 2 | 0 | O | Me | NHCbz |
| 1208 | tetrahydropyrimidin-2-ylaminocarbonyl | 2 | 0 | O | Me | NHSO$_2$-n-Bu |
| 1209 | imidazolin-2-ylaminocarbonyl | 2 | 0 | O | Bn | H |
| 1210 | tetrahydropyrimidin-2-ylaminocarbonyl | 2 | 0 | O | Bn | H |
| 1211 | imidazolin-2-ylaminocarbonyl | 2 | 0 | O | Me | H |

| Ex. No. | R¹-U | m | n | G | R⁸ | R⁹ |
|---|---|---|---|---|---|---|
| 1212 | tetrahydropyrimidin-2-ylaminocarbonyl | 2 | 0 | O | Me | H |
| 1213 | imidazolin-2-ylaminocarbonyl | 2 | 0 | O | H | NHCbz |
| 1214 | tetrahydropyrimidin-2-ylaminocarbonyl | 2 | 0 | O | H | NHCbz |
| 1215 | imidazolin-2-ylaminocarbonyl | 2 | 0 | O | H | NHSO$_2$-n-Bu |
| 1216 | tetrahydropyrimidin-2-ylaminocarbonyl | 2 | 0 | O | H | NHSO$_2$-n-Bu |
| 1217 | imidazolin-2-ylaminocarbonyl | 2 | 0 | S | Me | H |
| 1218 | tetrahydropyrimidin-2-ylaminocarbonyl | 2 | 0 | S | Bn | H |
| 1219 | imidazolin-2-ylaminocarbonyl | 2 | 0 | S | H | NHCbz |
| 1220 | tetrahydropyrimidin-2-ylaminocarbonyl | 2 | 0 | S | H | NHSO$_2$-n-Bu |
| 1221 | imidazolin-2-ylamino | 2 | 1 | O | H | NHCbz |
| 1222 | imidazolin-2-ylamino | 3 | 1 | O | H | NHCbz |
| 1223 | tetrahydropyrimidin-2-ylamino | 2 | 1 | O | H | NHCbz |
| 1224 | tetrahydropyrimidin-2-ylamino | 3 | 1 | O | H | NHCbz |
| 1225 | imidazolin-2-ylamino | 2 | 1 | O | H | NHSO$_2$-n-Bu |

TABLE 3-continued

| | | | | | |
|---|---|---|---|---|---|
| 1226 | imidazolin-2-ylamino | 3 | 1 | O | H | NHSO$_2$-n-Bu |
| 1227 | tetrahydropyrimidin-2-ylamino | 2 | 1 | O | H | NHSO$_2$-n-Bu |
| 1228 | tetrahydropyrimidin-2-ylamino | 3 | 1 | O | H | NHSO$_2$-n-Bu |
| 1229 | imidazolin-2-ylamino | 2 | 1 | S | H | NHCbz |
| 1230 | imidazolin-2-ylamino | 3 | 1 | S | H | NHCbz |
| 1231 | tetrahydropyrimidin-2-ylamino | 2 | 1 | S | H | NHCbz |
| 1232 | tetrahydropyrimidin-2-ylamino | 3 | 1 | S | H | NHCbz |
| 1233 | imidazolin-2-ylamino | 2 | 1 | O | Me | H |
| 1234 | imidazolin-2-ylamino | 3 | 1 | O | Me | H |
| 1235 | tetrahydropyrimidin-2-ylamino | 2 | 1 | O | Bn | H |
| 1236 | tetrahydropyrimidin-2-ylamino | 3 | 1 | O | Bn | H |
| 1237 | imidazolin-2-ylamino | 2 | 1 | S | Me | H |
| 1238 | tetrahydropyrimidin-2-ylamino | 2 | 1 | S | Bn | H |
| 1239 | imidazolin-2-ylamino | 2 | 1 | O | Me | NHCbz |
| 1240 | tetrahydropyrimidin-2-ylamino | 2 | 1 | O | Me | NHCbz |
| 1241 | imidazolin-2-ylamino | 2 | 1 | O | H | NHCbz |
| 1242 | tetrahydropyrimidin-2-ylamino | 2 | 1 | O | H | NHCbz |
| 1243 | imidazolin-2-ylamino | 3 | 1 | O | H | NHCbz |
| 1244 | tetrahydropyrimidin-2-ylamino | 3 | 1 | O | H | NHCbz |
| 1245 | pyridin-2-ylamino | 2 | 1 | O | H | NHCbz |
| 1246 | imidazol-2-ylamino | 2 | 1 | O | H | NHCbz |
| 1247 | 1,2,4-thiadiazol-5-ylamino | 2 | 1 | O | H | NHCbz |
| 1248 | isoxazol-3-ylamino | 2 | 1 | O | H | NHCbz |
| 1249 | oxazol-2-ylamino | 2 | 1 | O | H | NHCbz |
| 1250 | 1,2,5-thiadiazol-3-ylamino | 2 | 1 | O | H | NHCbz |
| 1251 | benzimidazol-2-ylamino | 2 | 1 | O | H | NHCbz |
| 1252 | benzthiazol-2-ylamino | 2 | 1 | O | H | NHCbz |
| 1253 | 1,2-pyrazol-3-ylamino | 2 | 1 | O | H | NHCbz |
| 1254 | 1,2,4-triazol-5-ylamino | 2 | 1 | O | H | NHCbz |
| 1255 | imidazol-4-ylamino | 2 | 1 | O | H | NHCbz |
| 1256 | 1,3,4-oxadiazol-2-ylamino | 2 | 1 | O | H | NHCbz |
| 1257 | 1,2,4-thiadiazol-5-ylamino | 2 | 1 | O | H | NHCbz |
| 1258 | 1,2,4-thiadiazol-3-ylamino | 2 | 1 | O | H | NHCbz |
| 1259 | 1,2,5-oxadiazol-3-ylamino | 2 | 1 | O | H | NHCbz |
| 1260 | 1,2,4-oxadiazol-5-ylamino | 2 | 1 | O | H | NHCbz |
| 1261 | 1,2,4-oxadiazol-3-ylamino | 2 | 1 | O | H | NHCbz |
| 1262 | pyridin-2-ylamino | 3 | 0 | O | H | NHCbz |
| 1263 | imidazol-2-ylamino | 3 | 0 | O | H | NHCbz |
| 1264 | 1,2,4-thiadiazol-5-ylamino | 3 | 0 | O | H | NHCbz |
| 1265 | isoxazol-3-ylamino | 3 | 0 | O | H | NHCbz |
| 1266 | oxazol-2-ylamino | 3 | 0 | O | H | NHCbz |
| 1267 | 1,2,5-thiadiazol-3-ylamino | 3 | 0 | O | H | NHCbz |
| 1268 | benzimidazol-2-ylamino | 3 | 0 | O | H | NHCbz |
| 1269 | benzthiazol-2-ylamino | 3 | 0 | O | H | NHCbz |
| 1270 | 1,2-pyrazol-3-ylamino | 3 | 0 | O | H | NHCbz |
| 1271 | 1,2,4-triazol-5-ylamino | 3 | 0 | O | H | NHCbz |
| 1272 | imidazol-4-ylamino | 3 | 0 | O | H | NHCbz |
| 1273 | 1,3,4-oxadiazol-2-ylamino | 3 | 0 | O | H | NHCbz |
| 1274 | 1,2,4-thiadiazol-5-ylamino | 3 | 0 | O | H | NHCbz |
| 1275 | 1,2,4-thiadiazol-3-ylamino | 3 | 0 | O | H | NHCbz |
| 1276 | 1,2,5-oxadiazol-3-ylamino | 3 | 0 | O | H | NHCbz |
| 1277 | 1,2,4-oxadiazol-5-ylamino | 3 | 0 | O | H | NHCbz |
| 1278 | 1,2,4-oxadiazol-3-ylamino | 3 | 0 | O | H | NHCbz |
| 1279 | pyridin-2-ylamino | 2 | 0 | O | H | NHCbz |
| 1280 | imidazol-2-ylamino | 2 | 0 | O | H | NHCbz |
| 1281 | 1,2,4-thiadiazol-5-ylamino | 2 | 0 | O | H | NHCbz |
| 1282 | isoxazol-3-ylamino | 2 | 0 | O | H | NHCbz |
| 1283 | oxazol-2-ylamino | 2 | 0 | O | H | NHCbz |
| 1284 | 1,2,5-thiadiazol-3-ylamino | 2 | 0 | O | H | NHCbz |
| 1285 | benzimidazol-2-ylamino | 2 | 0 | O | H | NHCbz |
| 1286 | benzthiazol-2-ylamino | 2 | 0 | O | H | NHCbz |
| 1287 | 1,2-pyrazol-3-ylamino | 2 | 0 | O | H | NHCbz |
| 1288 | 1,2,4-triazol-5-ylamino | 2 | 0 | O | H | NHCbz |
| 1289 | imidazol-4-ylamino | 2 | 0 | O | H | NHCbz |
| 1290 | 1,3,4-oxadiazol-2-ylamino | 2 | 0 | O | H | NHCbz |
| 1291 | 1,2,4-thiadiazol-5-ylamino | 2 | 0 | O | H | NHCbz |
| 1292 | 1,2,4-thiadiazol-3-ylamino | 2 | 0 | O | H | NHCbz |
| 1293 | 1,2,5-oxadiazol-3-ylamino | 2 | 0 | O | H | NHCbz |
| 1294 | 1,2,4-oxadiazol-5-ylamino | 2 | 0 | O | H | NHCbz |
| 1295 | 1,2,4-oxadiazol-3-ylamino | 2 | 0 | O | H | NHCbz |

UTILITY

The compounds of Formula I of the present invention possess activity as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their lack of activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula I of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula I have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta)—Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 $\mu M$ for the inhibition of $\alpha_v\beta_3$-Vitronectin Binding Assay, with compounds preferably having $K_i$ values of less than about 0.1 $\mu M$. Compounds of the present invention are active in the $\alpha_v\beta_3$-Vitronectin Binding Assay as well as in cell-based assays of integrin adhesion mediated by the $\alpha_v\beta_3$-receptor.

Purified $\alpha_v\beta_3$ (human placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\alpha_v\beta_3$ or $\alpha_v\beta_5$ in the ELISA.

A submaximal concentration of biotinylated vitronectin was selected based on conc. response curve with fixed receptor conc. and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 $\mu L$/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM CaCl$_2$,1.0 mM MgCl$_2$.6H$_2$O,1.0 mM MnCl$_2$.4H$_2$O). Receptor is then blocked (200 $\mu L$/well) with 3.5% BSA in B/B buffer for 2 hours at room temperature. After washing once with 1.0% BSA in B/B buffer, biotinylated vitronectin (100 $\mu L$) and either inhibitor (11 $\mu L$) or B/B buffer w/1.0% BSA (11 $\mu L$) is added to each well. The plates are incubated 2 hours at room temperature. The plates are washed twice with B/B buffer and incubated 1 hour at room temperature with anti-biotin alkaline phosphatase (100 $\mu L$/well) in B/B buffer containing 1.0% BSA. The plates are washed twice with B/B buffer and alkaline phosphatase substrate (100 $\mu L$) is added. Color is developed at room temperature. Color development is stopped by addition of 2N NaOH (25 $\mu L$/well) and absorbance is read at 405 nm. The $IC_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 $\mu L$ of PRP (5×10$^8$ platelets/mL) were added to each micro test tube, and transmittance was set to 0%. 20 $\mu L$ of ADP (10 $\mu M$) was added to each tube, and the aggregation profiles were plotted (% transmittance versus time). Test agent (20 $\mu L$) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67: 519–528

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient a cceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition , parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

What is claimed is:

1. A compound of the formula (I)

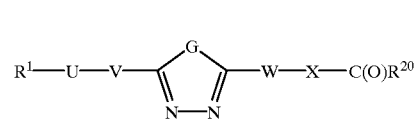

or pharmaceutically acceptable salts thereof, wherein:

$R^1$ is selected from:

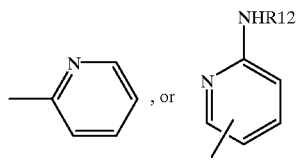

G is selected from O or S;

$R^2$ and $R^3$ are independently selected from: H, $C_1$–$C_4$ alkoxy, $NR^{11}R^{12}$, $=NR^{12}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, or $C_7$–$C_{11}$ arylcarbonyl;

U is selected from:
—$(CH_2)_n$—,
—$(CH_2)_nN(R^{12})(CH_2)_m$—, or
—$(CH_2)_nNHNH(CH_2)_m$—;

V is selected from:
—$(CH_2)_n$—,
—($C_1$–$C_6$ alkylene)—Q—, substituted with 0–3 groups independently selected from $R^{13}$,
—($C_2$–$C_7$ alkenylene)—Q—, substituted with 0–3 groups independently selected from $R^{13}$,
—($C_2$–$C_7$ alkynylene)—Q—, substituted with 0–3 groups independently selected from $R^{13}$, or
—(phenyl)—Q—, wherein said phenyl is substituted with 0–2 groups independently selected from $R^{13}$;

Q is selected from:
—$(CH_2)_n$—,
—$(CH_2)_nO(CH_2)_m$—, or
—$(CH_2)_nN(R^{12})(CH_2)_m$—;

W is selected from:
—$(CH_2)_qC(=O)N(R^{10})$—, —$SCH_2C(=O)N(R^{10})$—, or
—$C(=O)$—$N(R^{10})$—$(CH_2)_q$—;

X is selected from:
—$(CH_2)_q$—$CH(R^8)$—$CH(R^9)$—$(CH_2)_q$—$CH(CH_2R^9)$ or —$CH_2$—;

$R^5$ is selected from: H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —$N(R^{11})R^{12}$; halo, $CF_3$, CN, $C_1$–$C_6$ alkoxycarbonyl, carboxy, piperidinyl, morpholinyl or pyridinyl;

$R^6$ is selected from: H, $C_1$–$C_4$ alkyl, hydroxy, $C_1$–$C_4$ alkoxy, nitro, $C_1$–$C_6$ alkylcarbonyl, —$N(R^{11})R^{12}$, cyano, halo, —$S(O)mR^{10}$, $CO_2R^{10}$, $OR^{10}$,
$C_6$ to $C_{10}$ aryl optionally substituted with 1–3 groups selected from halogen, $C_1$–$C_6$ alkoxy, $C_1$–$C_6$ alkyl, $CF_3$, $S(O)_mMe$, or —$NMe_2$;
methylenedioxy when $R^6$ is a substituent on aryl, or a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl, or morpholinyl;

$R^8$ is selected from:
H,
$C_1$–$C_{10}$ alkyl, substituted with 0–3 $R^6$,
$C_2$–$C_{10}$ alkenyl, substituted with 0–3 $R^6$,
$C_2$–$C_{10}$ alkynyl, substituted with 0–3 $R^6$,
$C_3$–$C_8$ cycloalkyl, substituted with 0–3 $R^6$,
$C_5$–$C_6$ cycloalkenyl, substituted with 0–3 $R^6$,
aryl, substituted with 0–3 $R^6$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl;

$R^9$ is selected from: H, hydroxy, $C_1$–$C_{10}$ alkoxy, $N(R^{10})R^{11}$, or —$N(R^{16})R^{17}$;

$R^{10}$ is selected from H or $C_1$–$C_{10}$ alkyl substituted with 0–2 $R^5$;

$R^{11}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^5$;

alternatively, $R^{10}$ and $R^{11}$ when both are substituents on the same nitrogen atom (as in —$NR^{10}R^{11}$) can be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 1–3 groups selected from: $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{12}$ is selected from:
H, $C_1$–$C_6$ alkyl, $C_1$–$C_4$ alkoxycarbonyl, $C_1$–$C_6$ alkylcarbonyl, $C_1$–$C_6$ alkylsulfonyl, aryl($C_1$–$C_4$ alkyl)sulfonyl, arylsulfonyl, aryl, heteroarylcarbonyl, or heteroarylalkylcarbonyl, wherein said aryl groups are substituted with 0–3 substituents selected from the group consisting of: $C_1$–$C_4$ alkyl, $C_1$–$C_4$ alkoxy, halo, $CF_3$, and $NO_2$;

$R^{13}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^{10}$ or —$C(=O)N(R^{10})R^{11}$;

$R^{16}$ is selected from:
—$C(=O)$—$O$—$R^{18a}$,
—$C(=O)$—$R^{18b}$,
—$SO_2$—$R^{18a}$,
—$SO_2$—$N(18^b)_2$;

$R^{17}$ is selected from H or $C_1$–$C_4$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, isoxazolyl, benzimidazolyl, piperidinyl, tetrahydrofuranyl, pyranyl, pyrimidinyl, 3H-indolyl, carbazolyl, pyrrolidinyl, piperidinyl, indolinyl, or morpholinyl, said heterocyclic ring being substituted with 0–4 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolinyl, isoxazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from: H, halogen, $CF_3$, CN, $NO_2$, $NR^{11}R^{12}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl ($C_1$–$C_6$ alkyl)—, $C_1$–$C_6$ alkoxy, or $C_1$–$C_4$ alkoxycarbonyl;

$R^{20}$ is selected from:
hydroxy;
$C_1$ to $C_{10}$ alkoxy;
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-, $R^{21}$ is selected from $C_1$–$C_8$ alkyl, $C_2$–$C_6$ alkenyl, $C_3$–$C_{11}$, cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^5$;

m is 0–2;
n is 0–2;
p is 0–2;
q is 0–1; and
r is 0–2;
with the proviso that when V is -(phenyl)—Q—, then either: U is not a direct bond or Q is not a direct bond.

2. A compound of claim 1 selected from the group consisting of:
2(S)-Benzyloxycarbonylamino-3-[[2-[4-[N-(pyridin-2-yl)amino]butyl]-1,3,4-thiadiazol-5-yl]carbonyl]aminopropionic acid TFA salt
2(S)-(2,4,6-Trimethylphenylsulfonyl)amino-3-[[2-[4-[N-(pyridin-2-yl)amino]butyl]-1,3,4-thiadiazol-5-yl]carbonyl]aminopropionic acid TFA salt
2(S)-(1-Naphthalenesulfonyl)amino-3-[[2-[4-[N-(pyridin-2-yl)amino]butyl]-1,3,4-thiadiazol-5-yl]carbonyl]aminopropionic acid TFA salt.

3. A pharmaceutical composition comprising a pharmaceutical carrier and a therapeutically effective amount of a compound of claim 1 or a pharmaceutically acceptable salt from thereof.

4. A pharmaceutical composition comprising a pharmaceutical carrier and a therapeutically effective amount of a compound of claim 2 or a pharmaceutically acceptable salt form thereof.

5. A method in inhibiting the aggregation of blood platelets which comprises administering to a host in need of such inhibition a therapeutically effective amount of a compound of claim 1.

6. A method of inhibiting the aggregation of blood platelets which comprises administering to a host in need of such inhibition a therapeutically effective amount of a compound of claim 2.

7. A method of treating thromboembolic disorders selected from thrombus or embolus formation, harmful platelet aggrgation, reocclusion following thrombolysis, reperfusion injury, restenosis, atherosclerosis, stroke, myocardial infarction, and unstable angina, which comprises administering to a host in need of such treatment a therapeutically effective amount of a compound of claim 1.

8. A method of treating thromboembolic disorders selected from thrombus or embolus formation, harmful platelet aggregaion, reocclusion following thrombolysis, reperfusion injury, restenosis, atherosclerosis, stroke myocardial infarction, and unstable angina, which comprises administering to a host in need of such treatment a therapeutically effective amount of a compound of claim 2.

* * * * *